United States Patent
Kadoch et al.

(10) Patent No.: US 9,410,943 B2
(45) Date of Patent: Aug. 9, 2016

(54) METHODS, COMPOSITIONS AND SCREENS FOR THERAPEUTICS FOR THE TREATMENT OF SYNOVIAL SARCOMA

(71) Applicant: The Board of Trustees of the Leland Stanford Junior University, Palo Alto, CA (US)

(72) Inventors: Cigall Kadoch, Stanford, CA (US); Gerald R. Crabtree, Woodside, CA (US)

(73) Assignee: The Board of Trustees of the Leland Stanford Junior University, Stanford, CA (US)

(*) Notice: Subject to any disclaimer, the term of this patent is extended or adjusted under 35 U.S.C. 154(b) by 0 days.

(21) Appl. No.: 14/210,087

(22) Filed: Mar. 13, 2014

(65) Prior Publication Data

US 2014/0288162 A1  Sep. 25, 2014

Related U.S. Application Data

(60) Provisional application No. 61/783,895, filed on Mar. 14, 2013.

(51) Int. Cl.
*A61K 31/661* (2006.01)
*G01N 33/50* (2006.01)
*G01N 33/574* (2006.01)
*A61K 31/7105* (2006.01)

(52) U.S. Cl.
CPC .......... *G01N 33/5011* (2013.01); *A61K 31/661* (2013.01); *A61K 31/7105* (2013.01); *G01N 33/57407* (2013.01)

(58) Field of Classification Search
CPC .................................................. A61K 31/661
See application file for complete search history.

(56) References Cited

U.S. PATENT DOCUMENTS 7,056,883 B2* 6/2006 Ito et al. .................. 514/19.3
2011/0061116 A1* 3/2011 Haldar et al. ................ 800/10

OTHER PUBLICATIONS

Eilber et al. 2007; Chemotherapy is associated with improved survival in adult patients with primary extremity synovial sarcoma. Annals of Surgery. 246(1): 105113.*
Kadoch et al. 2013a; Reversible disruption of mSWI/SNF (BAF) complexes by the SS18-SSx oncogenic fusion in synovial sarcoma. Cell 153: 71-85.*
Kadoch et al. 2013b; Proteomic and bioinformatic analysis of mammalian SWI/SNF complexes identifies extensive roles in human malignancy. Nature Geneticds. 45(6): 592-602.*
Conger. 2013. Protein complex may play role in preventing many forms of cancer, study shows. At: med.stanford.edu/news/all-news/2013/05/protein-complex-may-play-role-in-preventing-many-forms-of-cancer-study-shows.html.*
Takenaka et al. 2010; Downregulation of SS18-SSx1 expression in synovial sarcoma by small interfering RNA enhances the focal adhesion pathway and inhibits anchorage-independent growth in vitro and tumor growth in vivo. International Journal of Oncology. 36: 823-831.*
Thaete et al. 1999; Functional domains of the SYT and SYT-SSX synovial sarcoma translocation proteins and co-localization with the SNF protein BRM in the nucleus. Human Molecular Genetics. 8 (4): 585-591.*
Kasten et al. 2011; SnapShot: Chromatin remodeling: SWI/SNF. Cell 144: 310.*
Clark; et al., "Identification of novel genes, SYT and SSX, involved in the t(X;18)(p11.2;q11.2) translocation found in human synovial sarcoma", Nature Genetics (Aug. 1994), 7(4):502-8.
De Leeuw; et al., "Identification of two alternative fusion genes, SYT-SSX1 and SYT-SSX2, in t(X;18)(p11.2;q11.2)-positive synovial sarcomas", Human Molecular Genetics (Jun. 1995), 4(6):1097-9.
Kadoch; et al., "Proteomic and bioinformatic analysis of mammalian SWI/SNF complexes identifies extensive roles in human malignancy", Nature Genetics (Jun. 2013), 45(6):592-601.
Kadoch; et al., Reversible disruption of mSWI/SNF (BAF) complexes by the SS18-SSX oncogenic fusion in synovial sarcoma, Cell (Mar. 2013), 153(1):71-85.
Roberts; et al., "Highly penetrant, rapid tumorigenesis through conditional inversion of the tumor suppressor gene Snf5", Cancer Cell (Nov. 2002), 2(5):415-25.
Skytting; et al., "A novel fusion gene, SYT-SSX4, in synovial sarcoma", Journal of the National Cancer Institute (Jun. 1999), 91(11):974-5.
Svejstrup, "Synovial sarcoma mechanisms: a series of unfortunate events", Cell (Mar. 2013), 153(1):11-2.
Versteege; et al., "Truncating mutations of hSNF5/INI1 in aggressive paediatric cancer", Nature (Jul. 1998), 394 (6689):203-6.

* cited by examiner

*Primary Examiner* — Karen Cochrane Carlson
(74) *Attorney, Agent, or Firm* — Glenn J. Foulds; Bret E. Field; Bozicevic, Field & Francis LLP

(57) ABSTRACT

Methods and compositions are provided for treating human synovial sarcoma (SS). Also provided are screens to identify therapeutics for the treatment of synovial sarcoma. These methods, compositions, and screens are based on the discovery that promoting the assembly of wild type BAF (also called mSWI/SNF) complexes in SS cells by increasing levels of wild type SS18 and/or decreasing levels of SS18-SSX fusion protein leads to the cessation of proliferation of malignant cells in synovial sarcoma.

17 Claims, 23 Drawing Sheets
(20 of 23 Drawing Sheet(s) Filed in Color)

FIGURE 1A-C
A.
| PROTEIN | Cell type | | | | | |
|---|---|---|---|---|---|---|
| | ESC | | MEF | | P1.5 whole brain | |
| | % coverage | # peptides | % coverage | # peptides | % coverage | # peptides |
| Brg (Smarca4) | 45.7 | 101 | 34.3 | 68 | 42.4 | 123 |
| BAF250a (Arid1a) | 55.5 | 34 | 40.8 | 21 | 44.2 | 163 |
| BAF250b (Arid1b) | 17.5 | 27 | 25.3 | 52 | 34.3 | 96 |
| BAF155 (Smarcc1) | 62.8 | 130 | 54.4 | 80 | 42 | 75 |
| BAF57 (Smarce1) | 76.2 | 23 | 67.2 | 32 | 66.3 | 111 |
| BAF53a (Actl6a) | 52.9 | 26 | 37.1 | 18 | 50.8 | 31 |
| BAF47 (Smarcb1) | 54 | 27 | 27 | 14 | 43.1 | 26 |
| SS18 | 39.3 | 14 | 13.7 | 3 | 13.1 | 10 |
| Bmi1 | n.d. | n.d. | n.d. | n.d. | n.d. | n.d. |
| Ezh2 | n.d. | n.d. | n.d. | n.d. | n.d. | n.d. |
*n.d. (not detected)
B.
C.
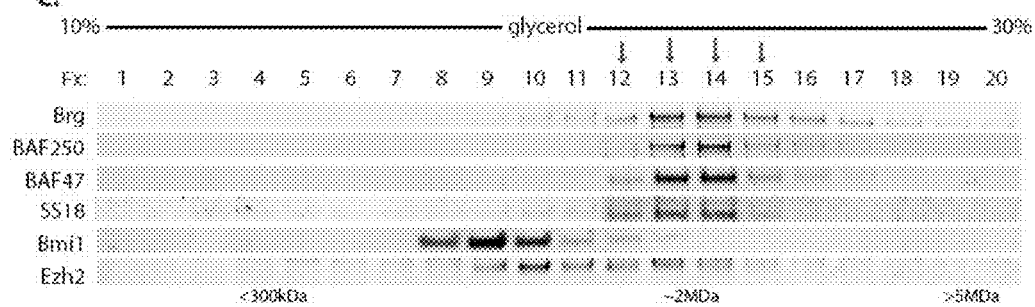

FIGURE 1D-E
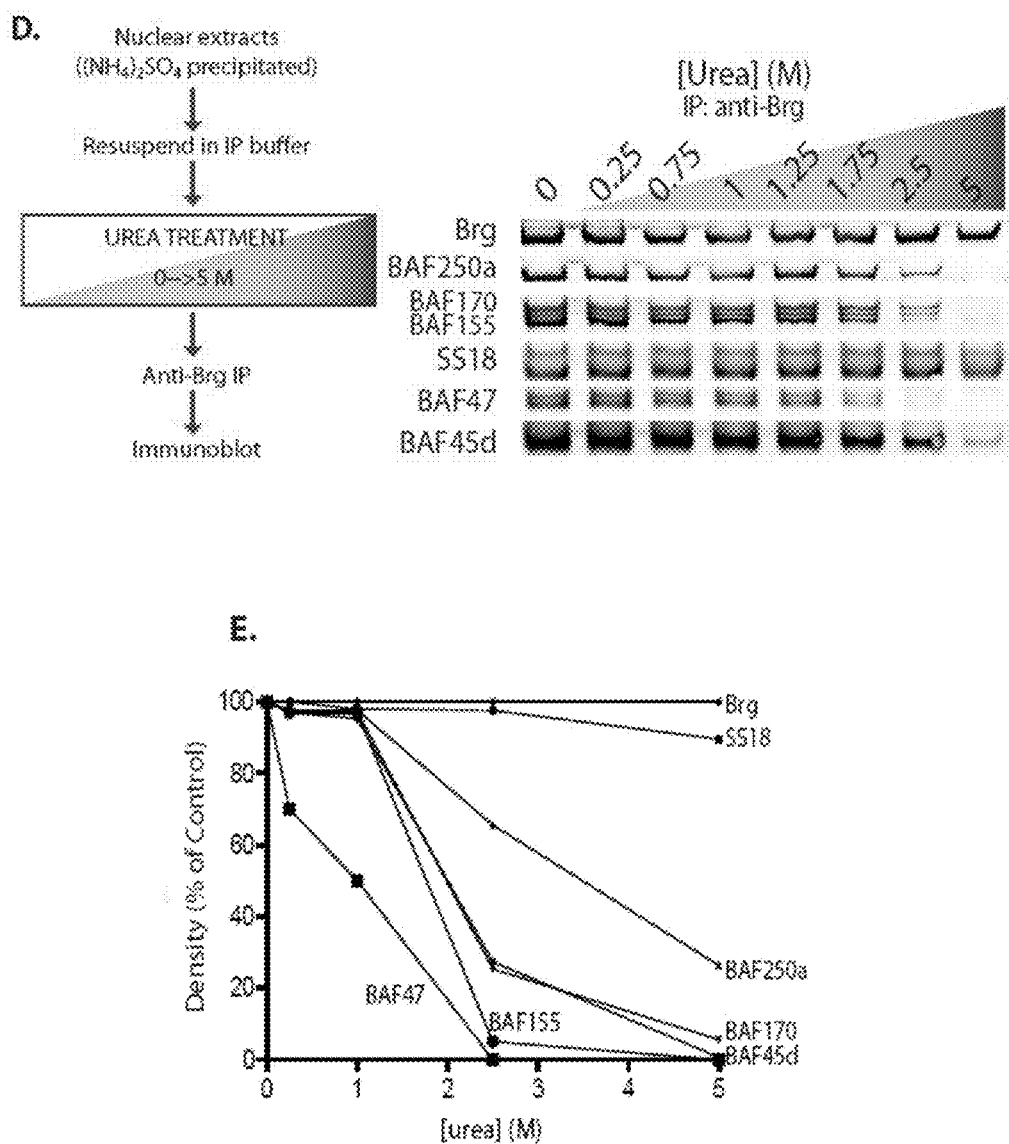

FIGURE 2A-C
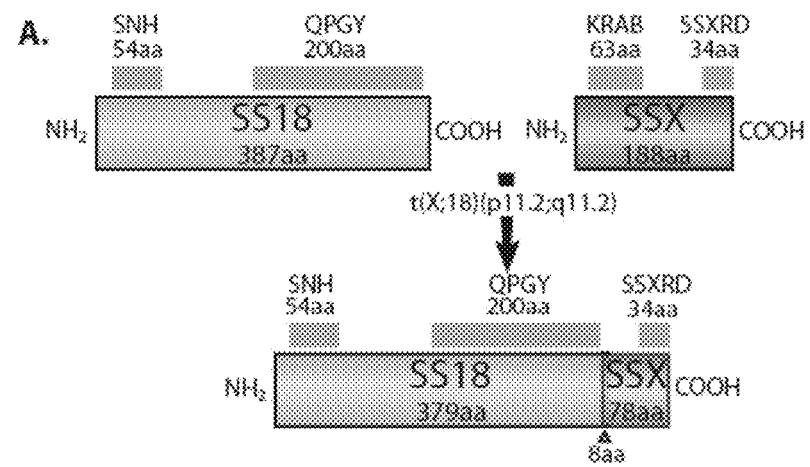
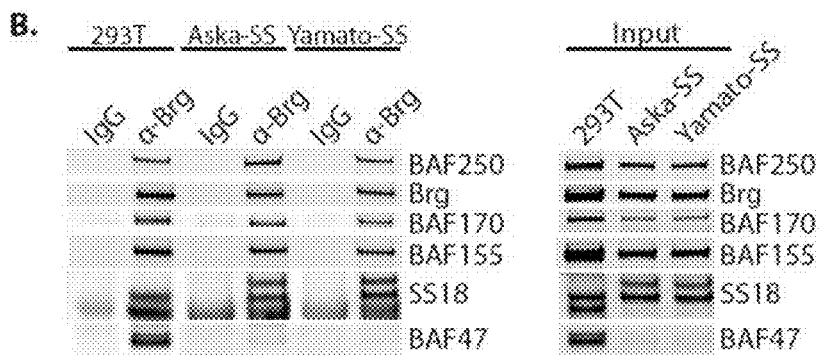
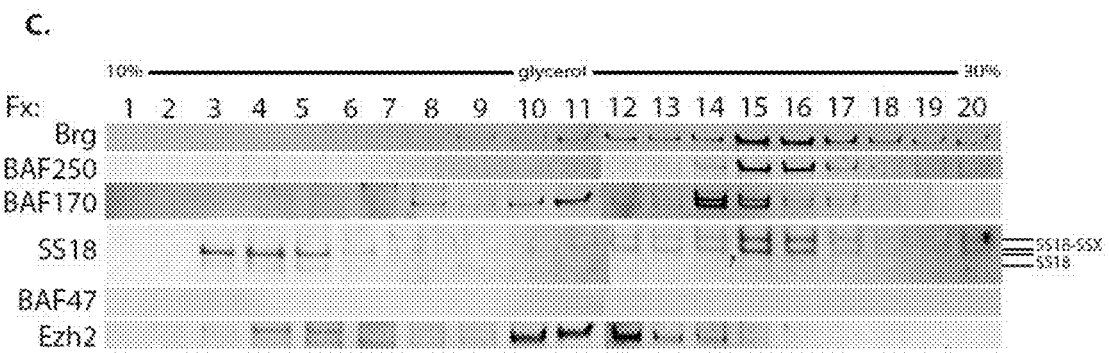

FIGURE 2D-E
D.
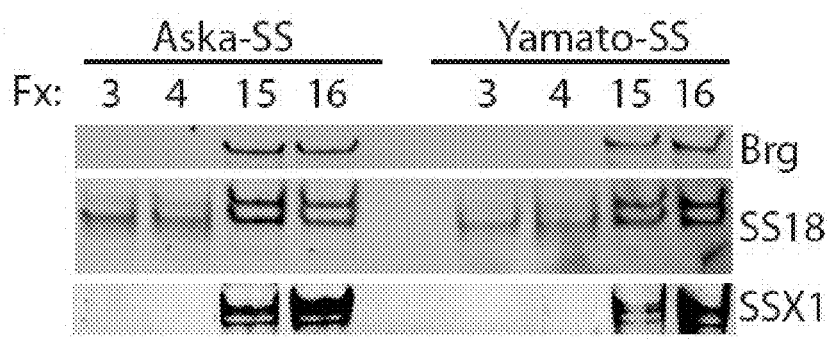
E. Immunodepletion
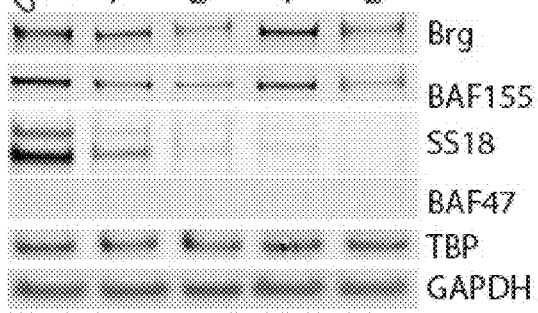

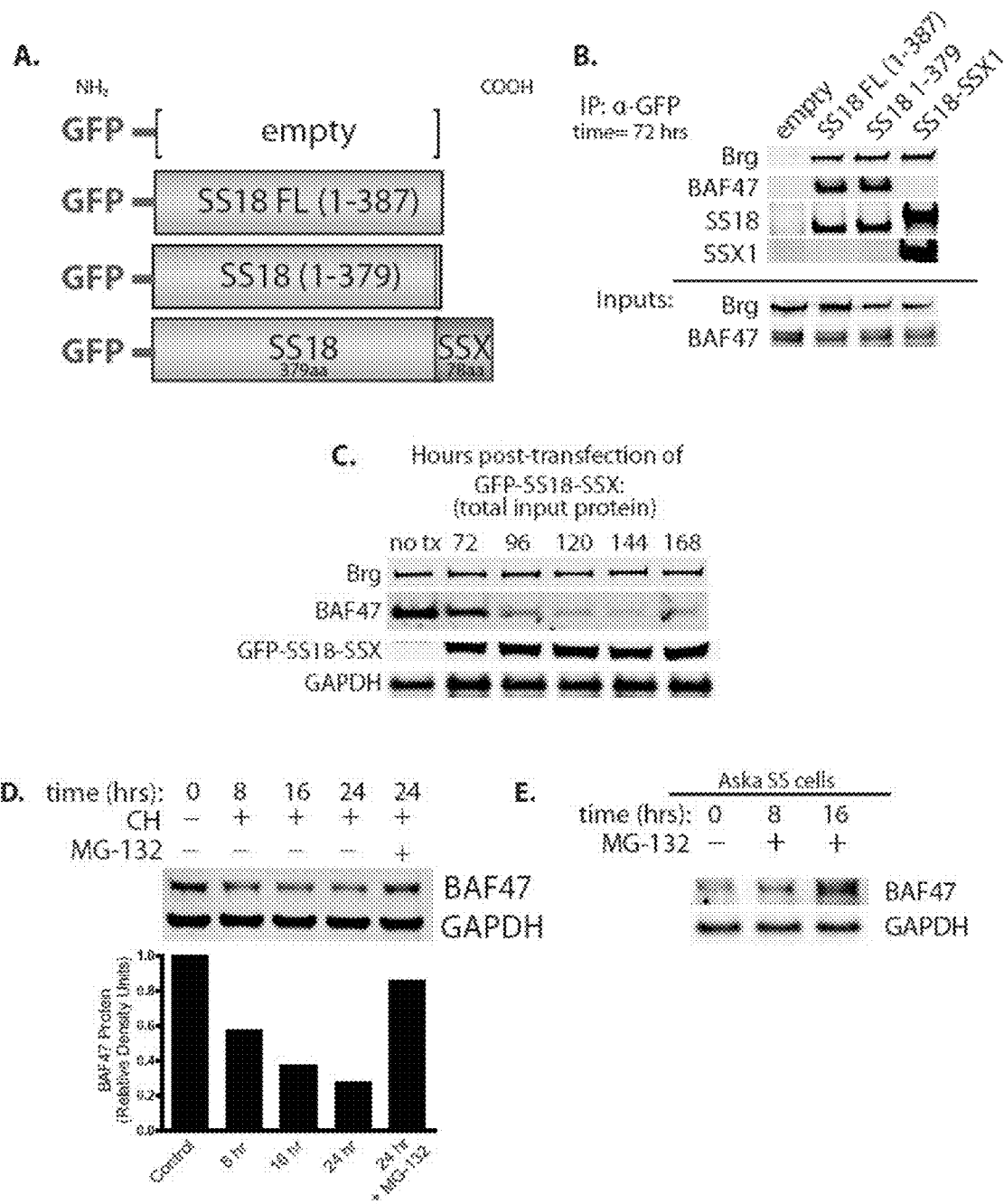
FIGURE 3A-E

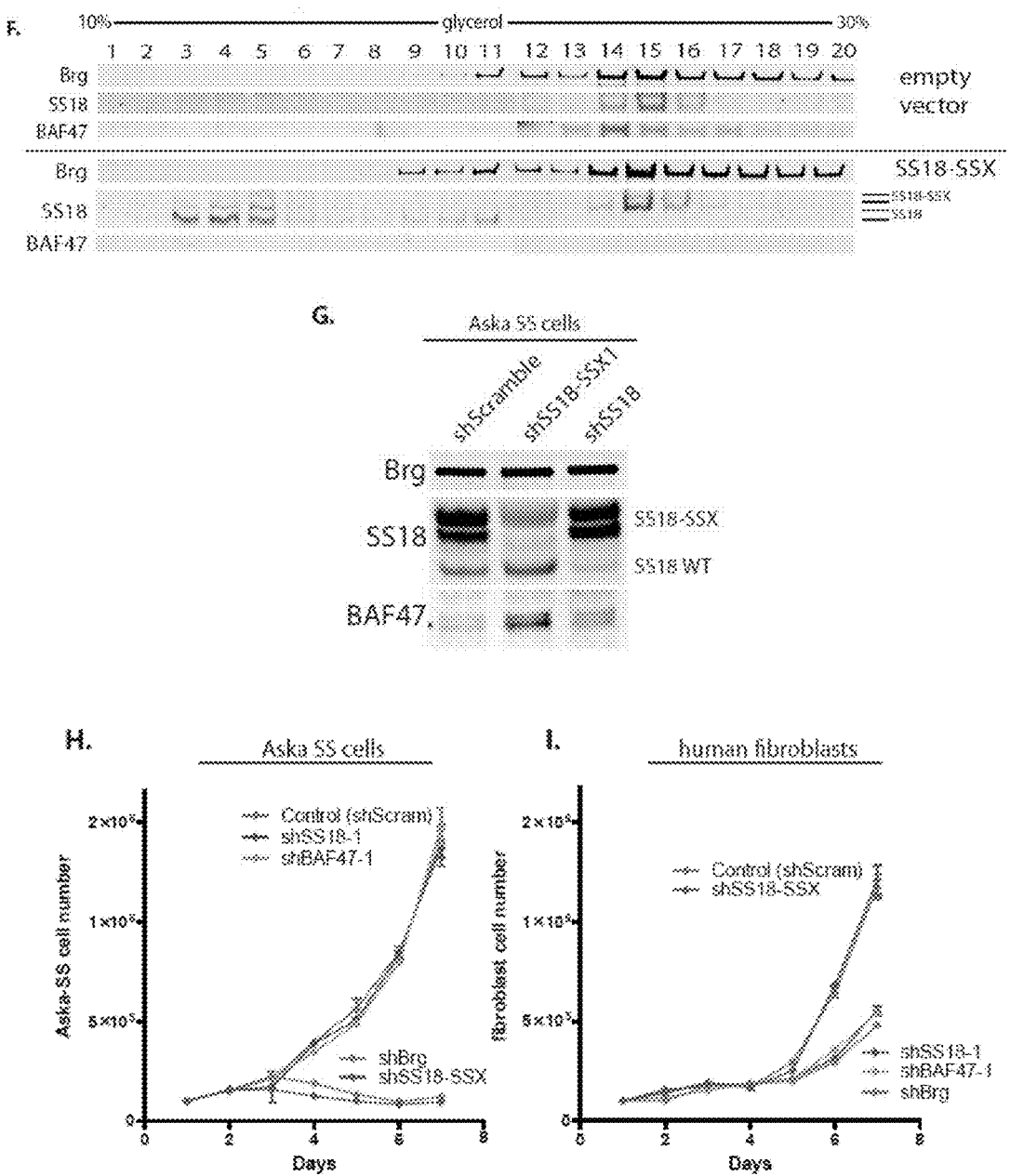
FIGURE 3F-I

FIGURE 4A-E
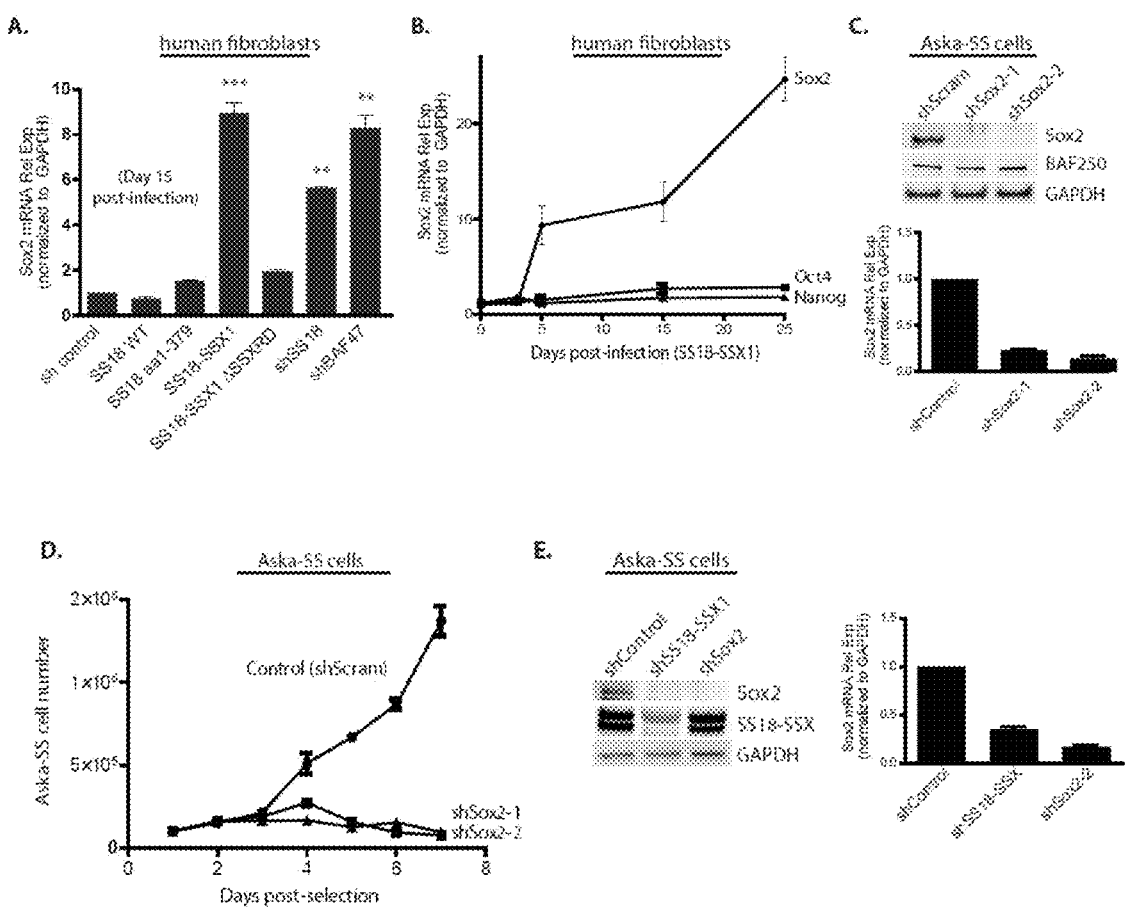

FIGURE 5A-B
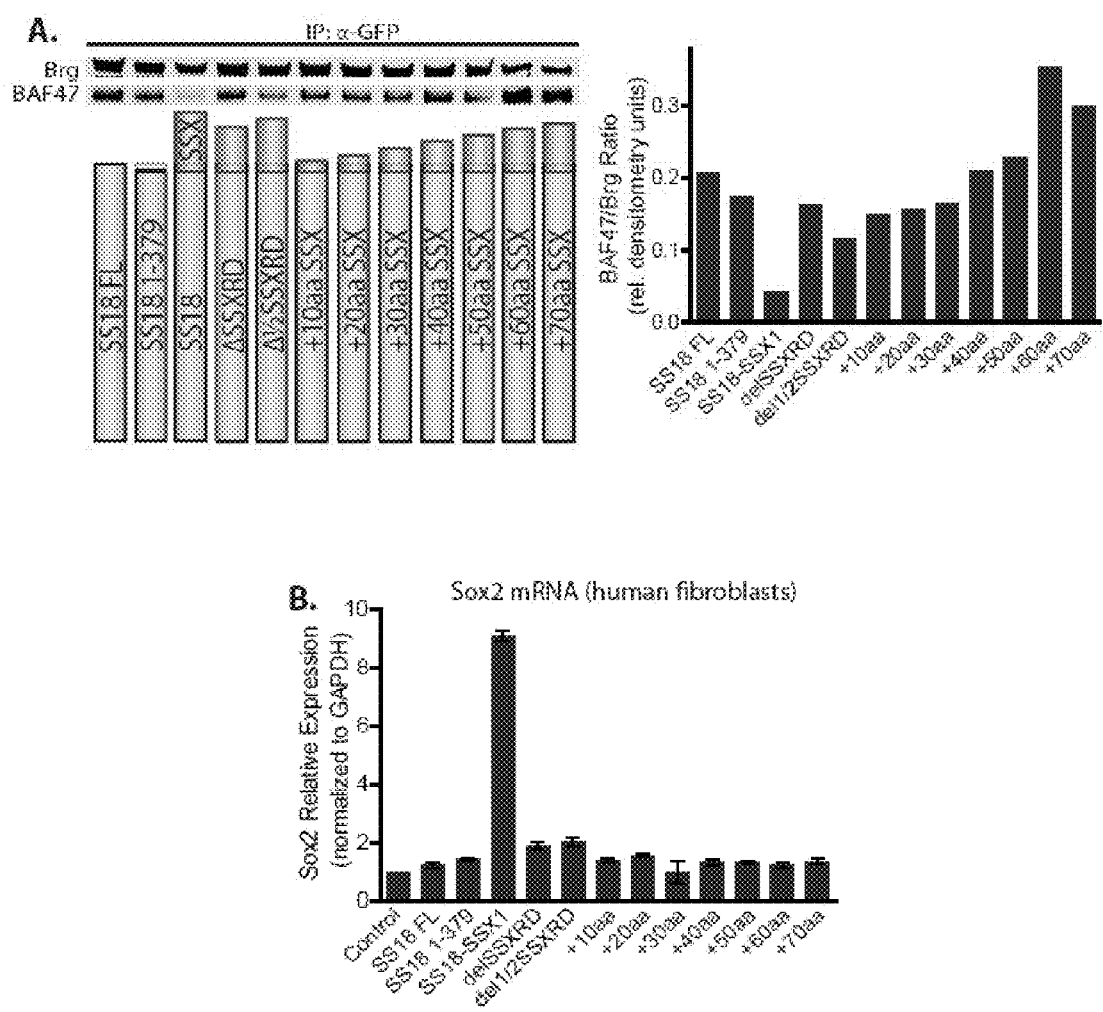

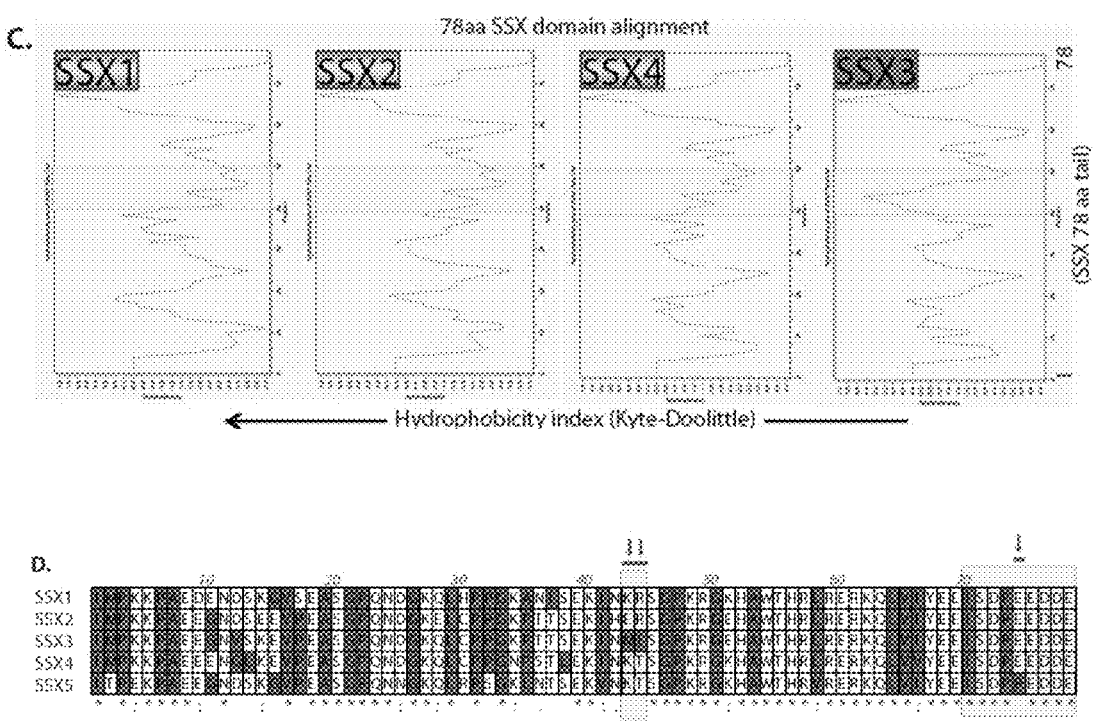
FIGURE 5C-D

FIGURE 5E-H
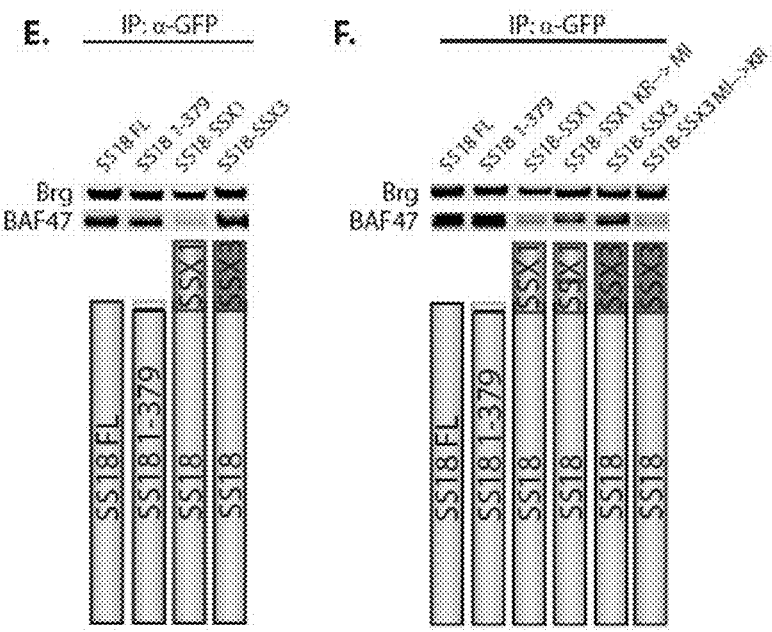
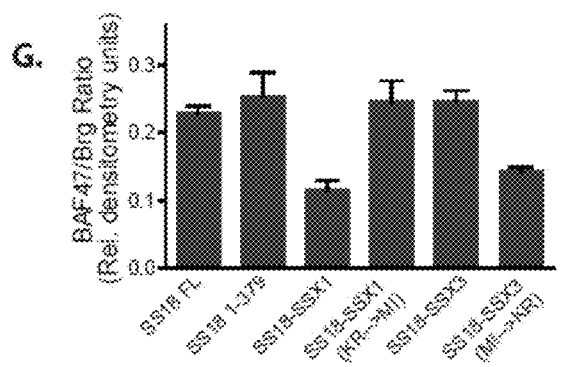
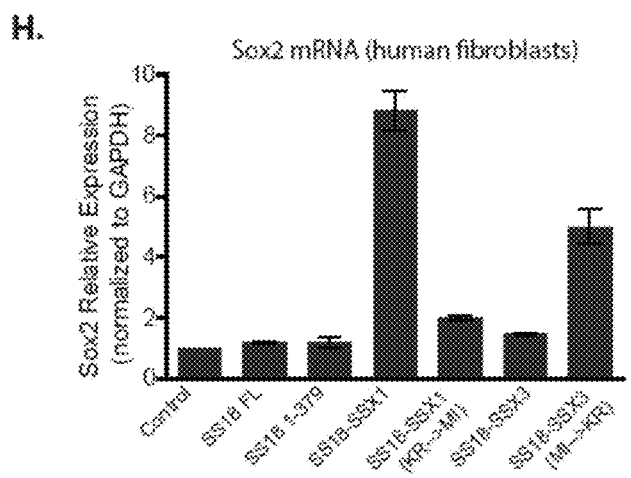

FIGURE 6A-D
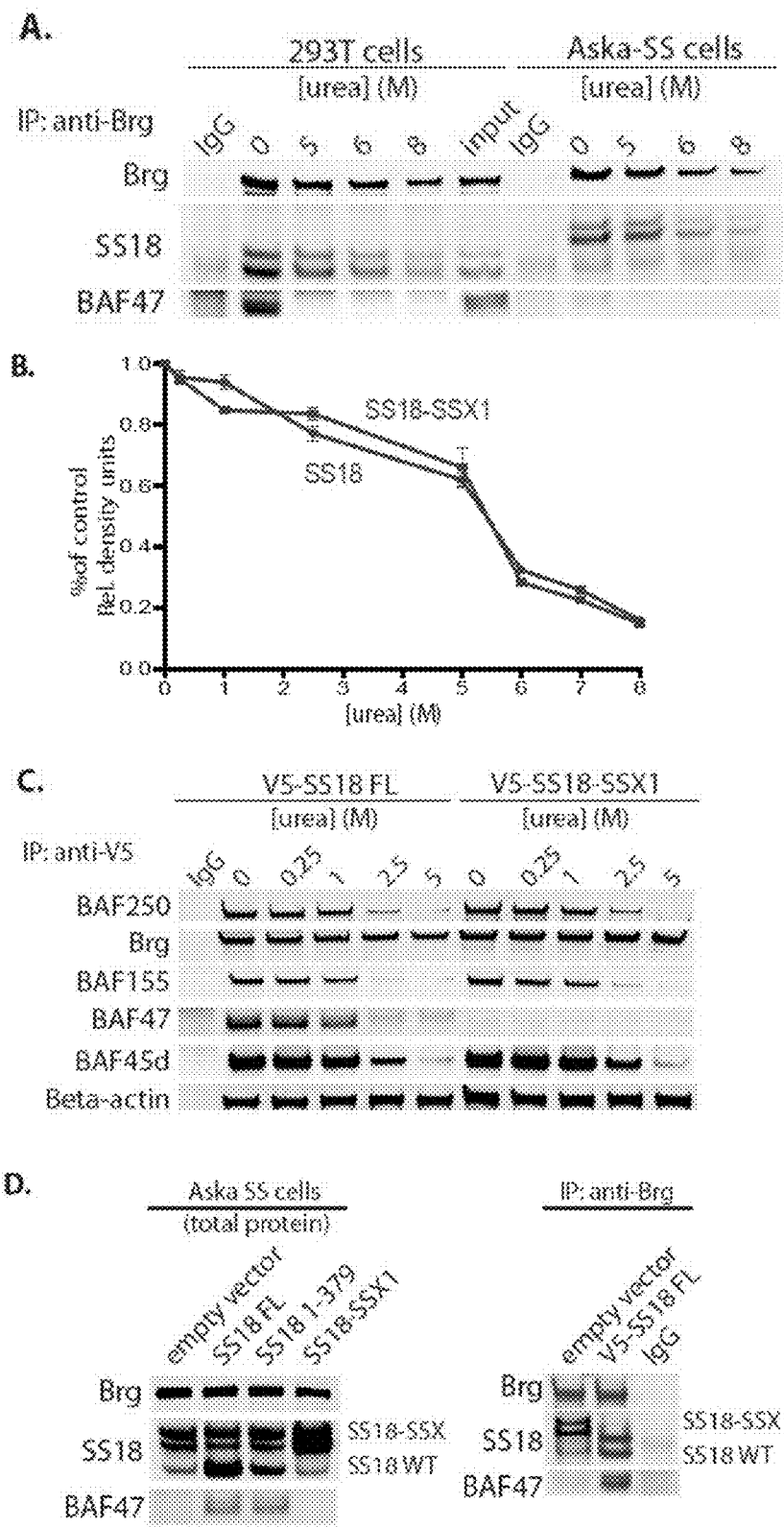

FIGURE 6E-G
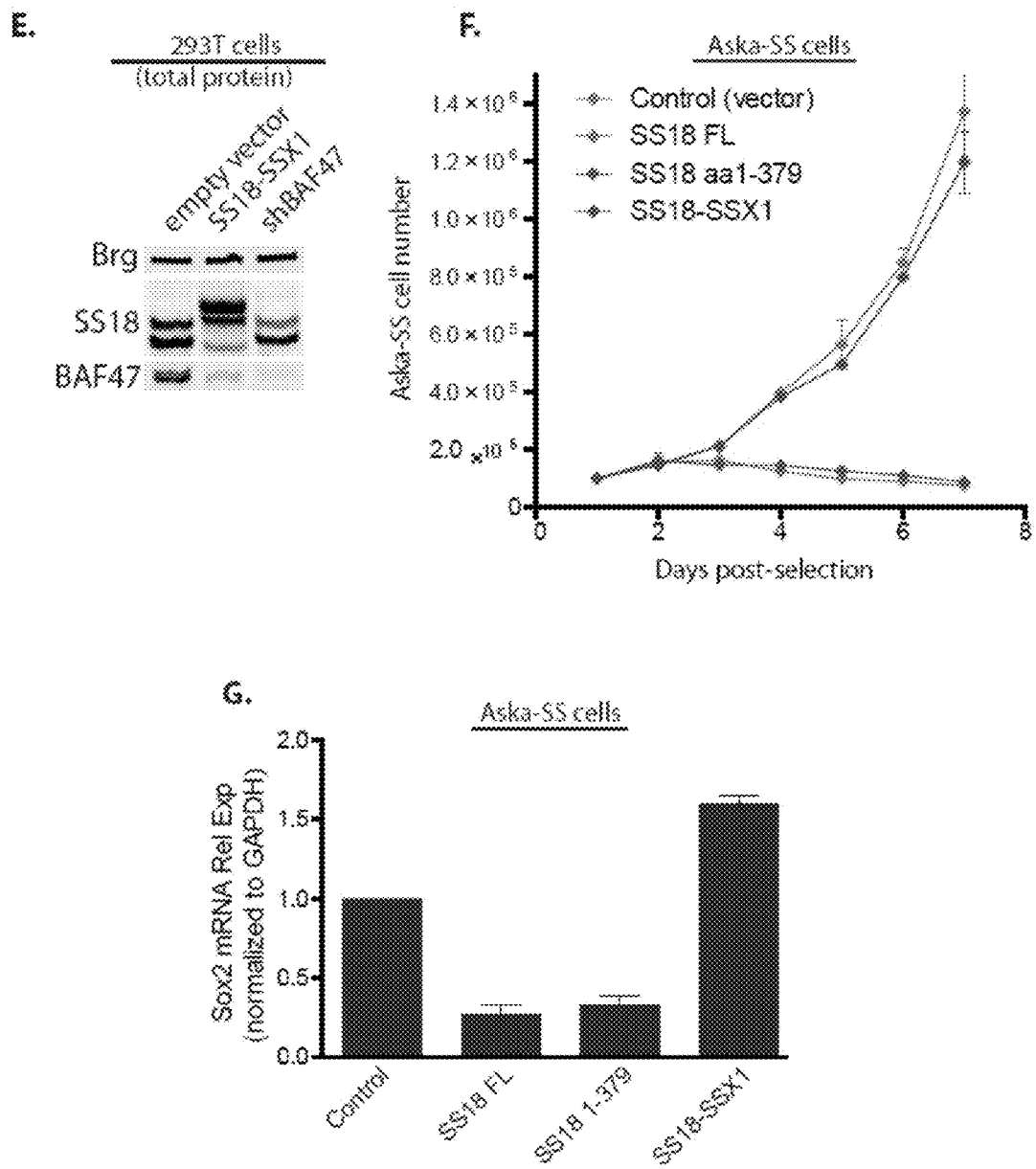

FIGURE 7A-C
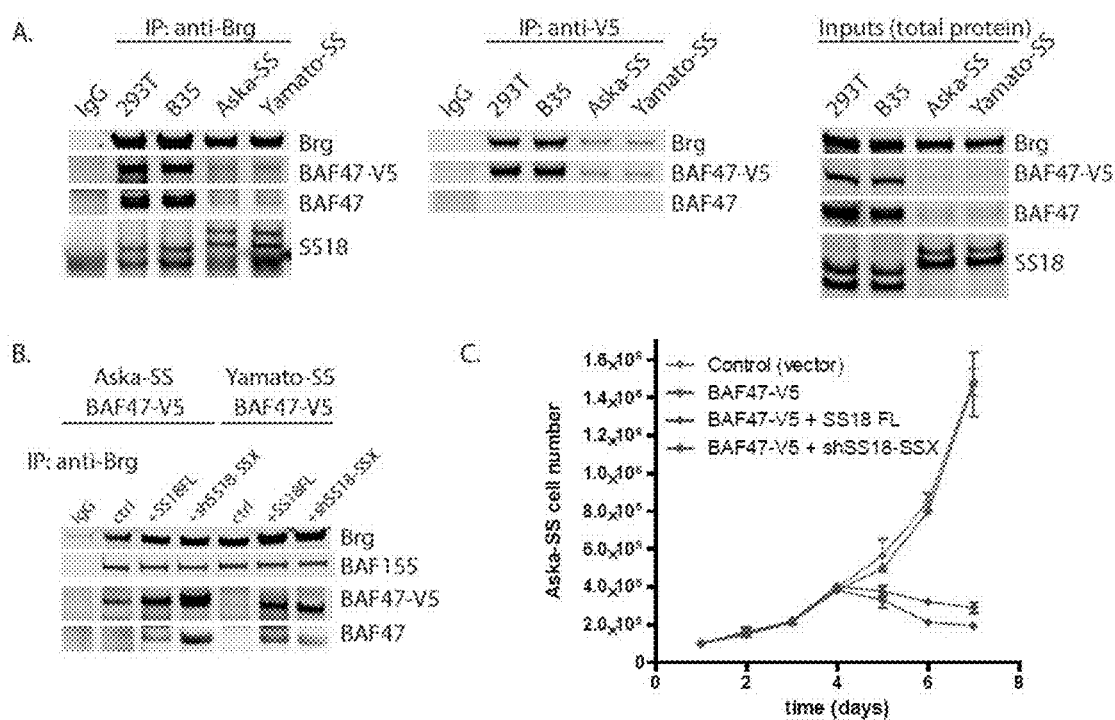

FIGURE 9A-C
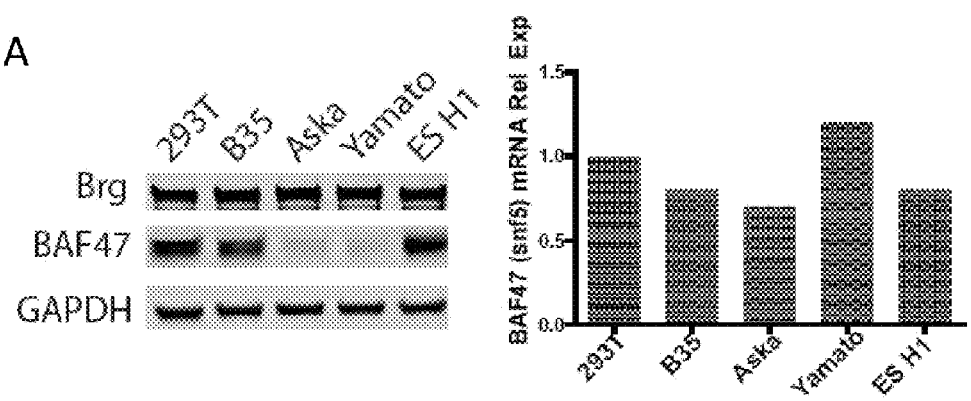
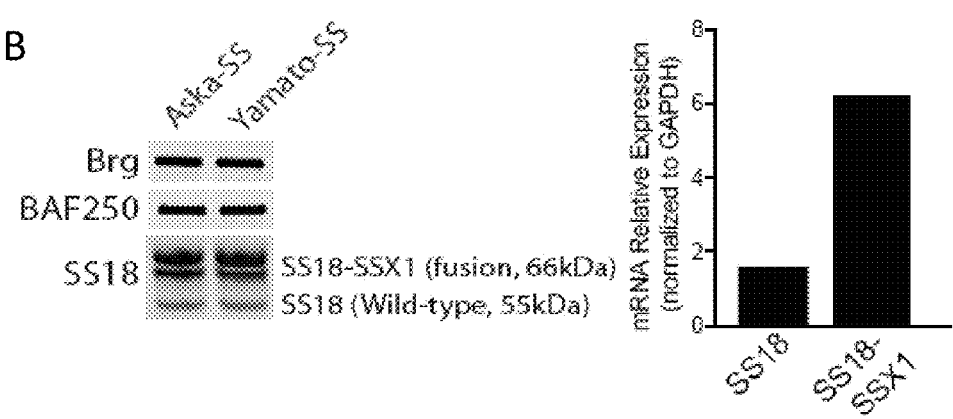
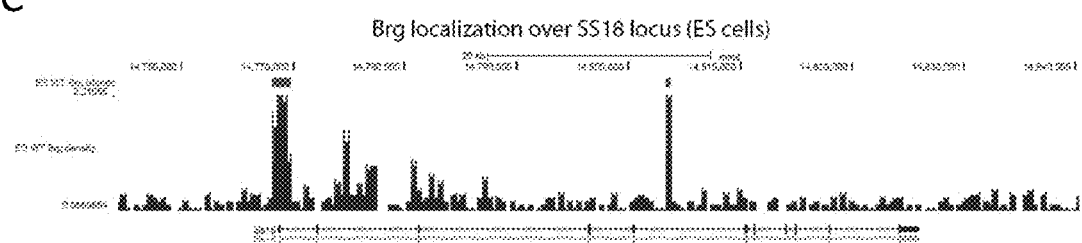

FIGURE 9D-E
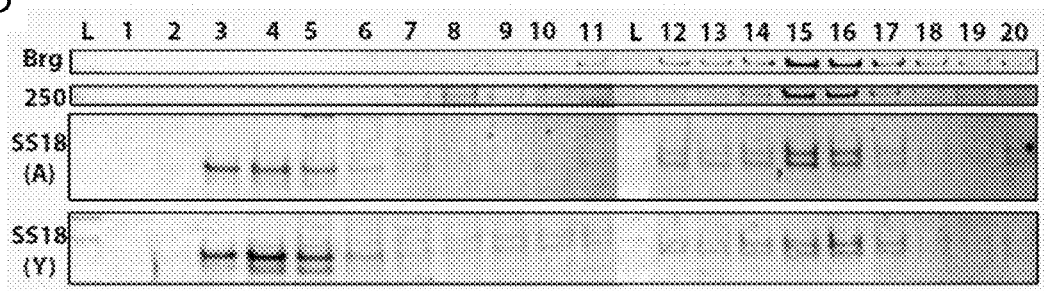
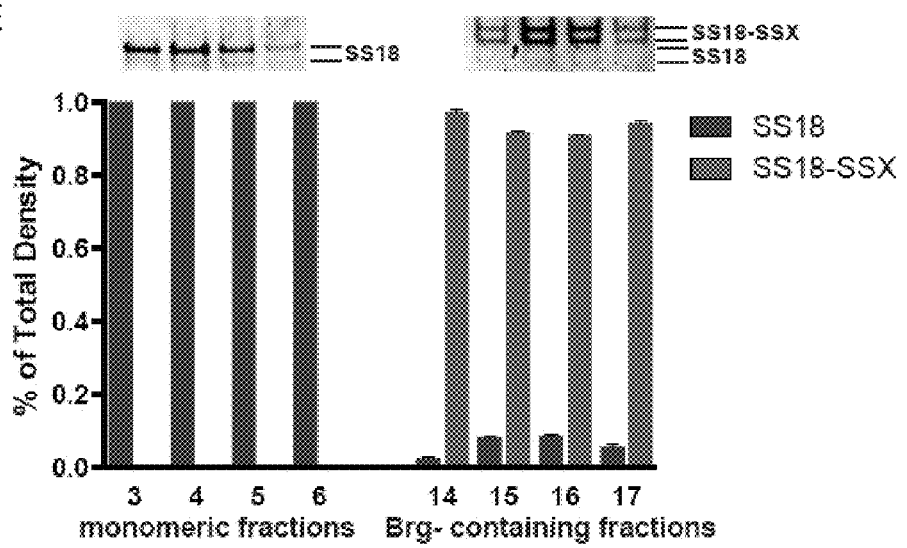

```
                          SEQUENCE LISTING

<160> NUMBER OF SEQ ID NOS: 18

<210> SEQ ID NO 1
<211> LENGTH: 78
<212> TYPE: PRT
<213> ORGANISM: Artificial Sequence
<220> FEATURE:
<223> OTHER INFORMATION: Synthetic polypeptide

<400> SEQUENCE: 1

Ile Met Pro Lys Lys Pro Ala Glu Asp Glu Asn Asp Ser Lys Gly Val
1               5                   10                  15

Ser Glu Ala Ser Gly Pro Gln Asn Asp Gly Lys Gln Leu His Pro Pro
            20                  25                  30

Gly Lys Ala Asn Ile Ser Glu Lys Ile Asn Lys Arg Ser Gly Pro Lys
        35                  40                  45

Arg Gly Lys His Ala Trp Thr His Arg Leu Arg Glu Arg Lys Gln Leu
    50                  55                  60

Val Ile Tyr Glu Glu Ile Ser Asp Pro Glu Glu Asp Asp Glu
65                  70                  75

<210> SEQ ID NO 2
<211> LENGTH: 78
<212> TYPE: PRT
<213> ORGANISM: Artificial Sequence
<220> FEATURE:
<223> OTHER INFORMATION: Synthetic polypeptide

<400> SEQUENCE: 2

Ile Met Pro Lys Lys Pro Ala Glu Glu Gly Asn Asp Ser Glu Glu Val
1               5                   10                  15

Pro Glu Ala Ser Gly Pro Gln Asn Asp Gly Lys Glu Leu Cys Pro Pro
            20                  25                  30

Gly Lys Pro Thr Thr Ser Glu Lys Ile His Glu Arg Ser Gly Pro Lys
        35                  40                  45

Arg Gly Glu His Ala Trp Thr His Arg Leu Arg Glu Arg Lys Gln Leu
    50                  55                  60

Val Ile Tyr Glu Glu Ile Ser Asp Pro Glu Glu Asp Asp Glu
65                  70                  75

<210> SEQ ID NO 3
```

<211> LENGTH: 78
<212> TYPE: PRT
<213> ORGANISM: Artificial Sequence
<220> FEATURE:
<223> OTHER INFORMATION: Synthetic polypeptide

<400> SEQUENCE: 3

```
Ile Met Pro Lys Lys Pro Ala Glu Glu Gly Asn Val Ser Lys Glu Val
  1               5                  10                  15

Pro Glu Ala Ser Gly Pro Gln Asn Asp Gly Lys Gln Leu Cys Pro Pro
             20                  25                  30

Gly Lys Pro Thr Thr Ser Glu Lys Ile Asn Met Ile Ser Gly Pro Lys
         35                  40                  45

Arg Gly Glu His Ala Trp Thr His Arg Leu Arg Glu Arg Lys Gln Leu
 50                  55                  60

Val Ile Tyr Glu Glu Ile Ser Asp Pro Glu Glu Asp Asp Glu
 65                  70                  75
```

<210> SEQ ID NO 4
<211> LENGTH: 78
<212> TYPE: PRT
<213> ORGANISM: Artificial Sequence
<220> FEATURE:
<223> OTHER INFORMATION: Synthetic polypeptide

<400> SEQUENCE: 4

```
Ile Met Pro Lys Lys Pro Ala Glu Glu Gly Asn Gly Leu Lys Glu Val
  1               5                  10                  15

Pro Glu Ala Ser Gly Pro Gln Asn Asp Gly Lys Gln Leu Cys Pro Pro
             20                  25                  30

Gly Asn Pro Ser Thr Leu Glu Lys Ile Asn Lys Thr Ser Gly Pro Lys
         35                  40                  45

Arg Gly Lys His Ala Trp Thr His Arg Leu Arg Glu Arg Lys Gln Leu
 50                  55                  60

Val Val Tyr Glu Glu Ile Ser Asp Pro Glu Glu Asp Asp Glu
 65                  70                  75
```

<210> SEQ ID NO 5
<211> LENGTH: 78
<212> TYPE: PRT
<213> ORGANISM: Artificial Sequence
<220> FEATURE:
<223> OTHER INFORMATION: Synthetic polypeptide

<400> SEQUENCE: 5

```
Ile Thr Pro Glu Lys Pro Ala Glu Glu Gly Asn Asp Ser Lys Gly Val
  1               5                  10                  15

Pro Glu Ala Ser Gly Pro Gln Asn Asn Gly Lys Gln Leu Arg Pro Ser
             20                  25                  30

Gly Lys Leu Asn Thr Ser Glu Lys Val Asn Lys Thr Ser Gly Pro Lys
         35                  40                  45

Arg Gly Lys His Ala Trp Thr His Arg Val Arg Glu Arg Lys Gln Leu
 50                  55                  60

Val Ile Tyr Glu Glu Ile Ser Asp Pro Pro Glu Asp Asp Glu
 65                  70                  75
```

<210> SEQ ID NO 6
<211> LENGTH: 418
<212> TYPE: PRT
<213> ORGANISM: Artificial Sequence
<220> FEATURE:

<223> OTHER INFORMATION: Synthetic polypeptide

<400> SEQUENCE: 6

```
Met Ser Val Ala Phe Ala Ala Pro Arg Gln Arg Gly Lys Gly Glu Ile
1               5                   10                  15

Thr Pro Ala Ala Ile Gln Lys Met Leu Asp Asp Asn Asn His Leu Ile
            20                  25                  30

Gln Cys Ile Met Asp Ser Gln Asn Lys Gly Lys Thr Ser Glu Cys Ser
        35                  40                  45

Gln Tyr Gln Gln Met Leu His Thr Asn Leu Val Tyr Leu Ala Thr Ile
    50                  55                  60

Ala Asp Ser Asn Gln Asn Met Gln Ser Leu Leu Pro Ala Pro Pro Thr
65                  70                  75                  80

Gln Asn Met Pro Met Gly Pro Gly Gly Met Asn Gln Ser Gly Pro Pro
                85                  90                  95

Pro Pro Pro Arg Ser His Asn Met Pro Ser Asp Gly Met Val Gly Gly
            100                 105                 110

Gly Pro Pro Ala Pro His Met Gln Asn Gln Met Asn Gly Gln Met Pro
        115                 120                 125

Gly Pro Asn His Met Pro Met Gln Gly Pro Gly Pro Asn Gln Leu Asn
    130                 135                 140

Met Thr Asn Ser Ser Met Asn Met Pro Ser Ser Ser His Gly Ser Met
145                 150                 155                 160

Gly Gly Tyr Asn His Ser Val Pro Ser Ser Gln Ser Met Pro Val Gln
                165                 170                 175

Asn Gln Met Thr Met Ser Gln Gly Gln Pro Met Gly Asn Tyr Gly Pro
            180                 185                 190

Arg Pro Asn Met Ser Met Gln Pro Asn Gln Gly Pro Met Met His Gln
        195                 200                 205

Gln Pro Pro Ser Gln Gln Tyr Asn Met Pro Gly Gly Gly Gln His
    210                 215                 220

Tyr Gln Gly Gln Gln Pro Pro Met Gly Met Met Gly Gln Val Asn Gln
225                 230                 235                 240

Gly Asn His Met Met Gly Gln Arg Gln Ile Pro Pro Tyr Arg Pro Pro
                245                 250                 255

Gln Gln Gly Pro Pro Gln Gln Tyr Ser Gly Gln Glu Asp Tyr Tyr Gly
            260                 265                 270

Asp Gln Tyr Ser His Gly Gly Gln Gly Pro Pro Glu Gly Met Asn Gln
        275                 280                 285

Gln Tyr Tyr Pro Asp Gly His Asn Asp Tyr Gly Tyr Gln Gln Pro Ser
    290                 295                 300

Tyr Pro Glu Gln Gly Tyr Asp Arg Pro Tyr Glu Asp Ser Ser Gln His
305                 310                 315                 320

Tyr Tyr Glu Gly Gly Asn Ser Gln Tyr Gly Gln Gln Asp Ala Tyr
                325                 330                 335

Gln Gly Pro Pro Pro Gln Gln Gly Tyr Pro Pro Gln Gln Gln Gln Tyr
            340                 345                 350

Pro Gly Gln Gln Gly Tyr Pro Gly Gln Gln Gly Tyr Gly Pro Ser
        355                 360                 365

Gln Gly Gly Pro Gly Gln Tyr Pro Asn Tyr Pro Gln Gly Gln Gly
    370                 375                 380

Gln Gln Tyr Gly Gly Tyr Arg Pro Thr Gln Pro Gly Pro Pro Gln Pro
385                 390                 395                 400
```

-continued

Pro Gln Gln Arg Pro Tyr Gly Tyr Asp Gln Gly Gln Tyr Gly Asn Tyr
               405                 410                 415

Gln Gln

<210> SEQ ID NO 7
<211> LENGTH: 387
<212> TYPE: PRT
<213> ORGANISM: Artificial Sequence
<220> FEATURE:
<223> OTHER INFORMATION: Synthetic polypeptide

<400> SEQUENCE: 7

Met Ser Val Ala Phe Ala Ala Pro Arg Gln Arg Gly Lys Gly Glu Ile
 1               5                  10                  15

Thr Pro Ala Ala Ile Gln Lys Met Leu Asp Asp Asn His Leu Ile
             20                  25                  30

Gln Cys Ile Met Asp Ser Gln Asn Lys Gly Lys Thr Ser Glu Cys Ser
             35                  40                  45

Gln Tyr Gln Gln Met Leu His Thr Asn Leu Val Tyr Leu Ala Thr Ile
 50                  55                  60

Ala Asp Ser Asn Gln Asn Met Gln Ser Leu Leu Pro Ala Pro Pro Thr
65                  70                  75                  80

Gln Asn Met Pro Met Gly Pro Gly Gly Met Asn Gln Ser Gly Pro Pro
                 85                  90                  95

Pro Pro Pro Arg Ser His Asn Met Pro Ser Asp Gly Met Val Gly Gly
                100                 105                 110

Gly Pro Pro Ala Pro His Met Gln Asn Gln Met Asn Gly Gln Met Pro
            115                 120                 125

Gly Pro Asn His Met Pro Met Gln Gly Pro Gly Pro Asn Gln Leu Asn
        130                 135                 140

Met Thr Asn Ser Ser Met Asn Met Pro Ser Ser Ser His Gly Ser Met
145                 150                 155                 160

Gly Gly Tyr Asn His Ser Val Pro Ser Ser Gln Ser Met Pro Val Gln
                165                 170                 175

Asn Gln Met Thr Met Ser Gln Gly Gln Pro Met Gly Asn Tyr Gly Pro
            180                 185                 190

Arg Pro Asn Met Ser Met Gln Pro Asn Gln Gly Pro Met Met His Gln
        195                 200                 205

Gln Pro Pro Ser Gln Gln Tyr Asn Met Pro Gln Gly Gly Gln His
    210                 215                 220

Tyr Gln Gly Gln Gln Pro Pro Met Gly Met Met Gly Gln Val Asn Gln
225                 230                 235                 240

Gly Asn His Met Met Gly Gln Arg Gln Ile Pro Pro Tyr Arg Pro Pro
                245                 250                 255

Gln Gln Gly Pro Pro Gln Gln Tyr Ser Gly Gln Glu Asp Tyr Tyr Gly
            260                 265                 270

Asp Gln Tyr Ser His Gly Gly Gln Gly Pro Pro Glu Gly Met Asn Gln
        275                 280                 285

Gln Tyr Tyr Pro Asp Gly Asn Ser Gln Tyr Gly Gln Gln Gln Asp Ala
    290                 295                 300

Tyr Gln Gly Pro Pro Gln Gln Gly Tyr Pro Gln Gln Gln
305                 310                 315                 320

Tyr Pro Gly Gln Gln Gly Tyr Pro Gly Gln Gln Gly Tyr Gly Pro
                325                 330                 335

```
Ser Gln Gly Gly Pro Gly Pro Gln Tyr Pro Asn Tyr Pro Gln Gly Gln
            340                 345                 350

Gly Gln Gln Tyr Gly Gly Tyr Arg Pro Thr Gln Pro Gly Pro Pro Gln
        355                 360                 365

Pro Pro Gln Gln Arg Pro Tyr Gly Tyr Asp Gly Gln Tyr Gly Asn
    370                 375                 380

Tyr Gln Gln
385

<210> SEQ ID NO 8
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 8
gagaagggcg tgagagagtg                                              20

<210> SEQ ID NO 9
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 9
aaacagccag tgcaggagtt                                              20

<210> SEQ ID NO 10
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 10
aaacagagct ttcccccaat                                              20

<210> SEQ ID NO 11
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 11
ttgagtgtgt tccctcctc                                               20

<210> SEQ ID NO 12
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 12
tctccaggtc cgtgtttacc                                              20

<210> SEQ ID NO 13
<211> LENGTH: 20
<212> TYPE: DNA
<213> ORGANISM: Artificial Sequence
<220> FEATURE:
```

<223> OTHER INFORMATION: Synthetic polynucleotide

<400> SEQUENCE: 13
cccgaaggtt ctccttttc                                              20

<210> SEQ ID NO 14
<211> LENGTH: 84
<212> TYPE: DNA
<213> ORGANISM: Artificial Sequence
<220> FEATURE:
<223> OTHER INFORMATION: Synthetic polynucleotide

<400> SEQUENCE: 14
ggacgaaaca ccggtccggc caagagttcg atgttagtct cgagactaac atcgaactct    60
tggtttttgg aattctcgac ctcg                                           84

<210> SEQ ID NO 15
<211> LENGTH: 84
<212> TYPE: DNA
<213> ORGANISM: Artificial Sequence
<220> FEATURE:
<223> OTHER INFORMATION: Synthetic polynucleotide

<400> SEQUENCE: 15
cgaggtcgag aattccaaaa accaagagtt cgatgttagt ctcgagacta acatcgaact    60
cttggccgga ccggtgtttc gtcc                                           84

<210> SEQ ID NO 16
<211> LENGTH: 84
<212> TYPE: DNA
<213> ORGANISM: Artificial Sequence
<220> FEATURE:
<223> OTHER INFORMATION: Synthetic polynucleotide

<400> SEQUENCE: 16
ggacgaaaca ccggtccggc ttacgctgag tacttcgact cgagtcgaag tactcagcgt    60 aagttttgg aattctcgac ctcg                                            84

<210> SEQ ID NO 17
<211> LENGTH: 84
<212> TYPE: DNA
<213> ORGANISM: Artificial Sequence
<220> FEATURE:
<223> OTHER INFORMATION: Synthetic polynucleotide

<400> SEQUENCE: 17
cgaggtcgag aattccaaaa acttacgctg agtacttcga ctcgagtcga agtactcagc    60
gtaagccgga ccggtgtttc gtcc                                           84

<210> SEQ ID NO 18
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 18

Ser Asp Pro Glu Glu Asp Asp Glu
 1               5

METHODS, COMPOSITIONS AND SCREENS FOR THERAPEUTICS FOR THE TREATMENT OF SYNOVIAL SARCOMA

CROSS REFERENCE TO RELATED APPLICATIONS

Pursuant to 35 U.S.C. §119 (e), this application claims priority to the filing date of the U.S. Provisional Patent Application Ser. No. 61/783,895 filed Mar. 14, 2013; the disclosure of which are herein incorporated by reference.

GOVERNMENT RIGHTS

This invention was made with government support under CA163915 awarded by the National Institutes of Health. The Government has certain rights in the invention.

FIELD OF THE INVENTION

This invention pertains to therapeutics for the treatment of synovial sarcoma.

BACKGROUND OF THE INVENTION

Human synovial sarcoma (SS) is a soft tissue sarcoma that is associated with a translocation event, t(X;18)(p11.2; q11.2), which fuses the SS18 gene on chromosome 18 to one of three closely related genes—SSX1, SSX2, or SSX4—on the X chromosome, resulting in an in-frame fusion protein in which the eight C-terminal amino acids of SS18 are replaced with 78 amino acids from the SSX C-terminus. This type of sarcoma accounts for about 8-10% of all soft-tissue malignancies and commonly occurs in the extremities of young adults and pediatric patients at inaccessible locations, which are often discovered late in the course of the disease. These malignancies are generally refractory to conventional chemotherapy-based forms of treatment; except for a small percentage of cases in which the tumors can be successfully removed with surgery, they are nearly always lethal. This underscores a significant need for novel therapeutic approaches in this disease. The present invention addresses these issues.

SUMMARY OF THE INVENTION

Methods and compositions are provided for treating synovial sarcoma (SS) in an individual having synovial sarcoma. Also provided are screens to identify therapeutics for the treatment of synovial sarcoma.

In some aspects of the invention, methods are provided for treating synovial sarcoma (SS) in an individual having synovial sarcoma. In some embodiments, the method comprises administering to an individual an agent that promotes the assembly of wild type BAF (also called SWI/SNF) complexes. In some embodiments, the agent increases the level, or amount, of wild type BAF47 in the cell. In some such embodiments, the agent increases the level, or amount, of wild type SS18 in the cell. In certain embodiments, the agent is a wild-type SS18 polypeptide or a nucleic acid that encodes a wild-type SS18 polypeptide. In some such embodiments, the agent decreases the level of SS18-SSX fusion protein in the cell. In certain embodiments, the agent is a nucleic acid inhibitor that is specific for SS18-SSX fusion transcript, e.g. an siRNA or shRNA that is specific for the 3'UTR of an SS18-SSX fusion transcript.

In some aspects of the invention, compositions are provided for treating human synovial sarcoma. In some embodiments, the composition comprises an agent that promotes the assembly of wild type BAF (also called SWI/SNF) complexes. In some embodiments, the agent increases the level, or amount, of wild type BAF47 in the cell. In some such embodiments, the agent increases the level, or amount, of wild type SS18 in the cell. In certain embodiments, the agent is a wild-type SS18 polypeptide or a nucleic acid that encodes a wild-type SS18 polypeptide. In some embodiments, the agent decreases the level of SS18-SSX fusion protein in the cell. In certain embodiments, the agent is a nucleic acid inhibitor that is specific for SS18-SSX fusion transcript, e.g. an siRNA or shRNA that is specific for the 3'UTR of an SS18-SSX fusion transcript.

In some aspects of the invention, screening methods are provided to identify a therapeutic for the treatment of SS. In one embodiment, a gain-of-function screen is provided to identify agents that promote the assembly of the wild type BAF complex, wherein an agent that promotes the assembly of the wild type BAF complex will find use as a therapeutic for the treatment of SS. This method is based upon the inventors' discovery that incorporation of the SS18-SSX fusion protein into the BAF complex leads to alterations in the composition of the BAF complex, eviction of BAF47 from the complex and its subsequent destabilization and proteasome-mediated degradation. Conversely, agents that promote the assembly of wild type complexes promote the restoration of subunit abundance, binding, assemble, and stoichiometry within the BAF complex, including, for example, the incorporation of wild type SS18 and BAF47, which prevents BAF47 degradation and restores wild type BAF complex activity, including, for example, appropriate regulation of the Ink4a and Sox2 promoters. As a result, appropriate formation of the BAF complex, restoration of subunit abundance, binding, assemble, and stoichiometry to wild type levels, increases in total cellular BAF47 protein levels, increases in Ink4a promoter activity, and decreases in Sox2 promoter activity may be used as read-outs to identify agents that promote the assembly of wild type BAF complex in cells. This gain-of-function approach has the advantage in that it eliminates non-specific toxic molecules that simply kill the cell or impair transcription, translation or protein stability.

BRIEF DESCRIPTION OF THE DRAWINGS

The invention is best understood from the following detailed description when read in conjunction with the accompanying drawings. The patent or application file contains at least one drawing executed in color. Copies of this patent or patent application publication with color drawing(s) will be provided by the Office upon request and payment of the necessary fee. It is emphasized that, according to common practice, the various features of the drawings are not to-scale. On the contrary, the dimensions of the various features are arbitrarily expanded or reduced for clarity. Included in the drawings are the following figures.

FIG. 1. SS18 is a dedicated, stable subunit of mSWI/SNF (BAF) complexes. (A) Composition of BAF complexes isolated from ES cells, MEFs and brain as determined by mass spectrometric analysis. See also FIG. 8C. (B) Immunoprecipitation (IP) using anti-Brg and anti-SS18 antibodies in 293T nuclear extracts (NE). See also FIG. 1A, B. (C) Glycerol gradient (10-30%) analysis on ES cell NE. (D) Left, Schematic for urea-based denaturation analyses; right, anti-Brg IPs on 293T NE preps treated with 0-5M urea. (E) Quantitative densitometry on urea denaturation immunoblots.

FIG. 2. mSWI/SNF (BAF) complexes are disrupted in synovial sarcoma cells bearing the SS18-SSX1 fusion protein. (A) Diagram of SS18-SSX fusion protein resulting from t(x; 18) translocation, hallmark to synovial sarcoma. (B) Anti-Brg IP (left) and total protein (right), in 293T cells as compared to synovial sarcoma (SS) cell lines, Aska-SS and Yamato-SS. See also FIG. 9A-C. (C) Glycerol gradient (10-30%, fractions 1-20) analysis on Aska-SS cell NE. See also FIG. 9D, E. (D) Side-by-side comparison of fractions 3,4 and 15,16 of Aska-SS glycerol gradient analysis. (E) Immunodepletion studies performed on 293T and Aska-SS cells using anti-BAF155 and anti-SSX1 antibodies. (undepleted=antibody not added).

FIG. 3. SS18-SSX1 ejects BAF47 and wild-type SS18 to recapitulate BAF complex phenotype in synovial sarcoma cells. (A) N-terminal GFP-tagged constructs of SS18 FL, SS18 1-379 (−8 aa), and SS18-SSX. (B) Anti-GFP IP of BAF complexes 72 hrs post-transfection with various pEGFP constructs in 293T fibroblasts. See also FIG. 10. (C) Immunoblot analysis on total protein isolated from transfected 293T cells at time t=0 hrs to t=168 hrs post-transfection with GFP-SS18-SSX. (D) Top, Cyclohexamide (CH) chase treatment of 293T cells, t=0 to t=24 hours, +/−MG-132 proteosome inhibitor. Bottom, quantitative densitometry of BAF47 protein levels on immunoblot. (E) Immunoblot analysis for BAF47 protein in Aska-SS cells treated with MG-132 proteosome inhibitor for t=8 and t=16 hours. (F) Glycerol gradient analyses on 293T cells infected with lentivirus (LV) containing either empty vector (top half) or SS18-SSX (bottom half). (G) shRNA-mediated knock-down (KD) of SS18-SSX and wild-type SS18 in Aska-SS cells. (H) Cell proliferation analyses of Aska-SS cells infected with shScramble control vector or delivery constructs containing shRNA KD to BAF subunits. Cells plated in triplicate at 10^5 cells/well per condition. Error bars, s.d. of n=3 experiments. (I) Cell proliferation analyses of human primary neonatal foreskin fibroblasts infected with shScramble control vector or shRNA KD to BAF complex subunits. Cells plated in triplicate at 10^5 cells/well per condition. Error bars, s.d. of n=3 experiments.

FIG. 5. Molecular requirements of the 78 aa SSX peptide for BAF47 subunit ejection from mSWI/SNF-like BAF complexes. (A) Left, Immunoblot analysis for BAF47 and Brg on anti-Brg IPs (Top) of 293T cells transfected with various SS18/SS18-SSX constructs (Bottom). Right, quantitative densitometry depicting BAF47/Brg protein ratios in IP studies. (B) Sox2 mRNA levels in human fibroblasts day 15 post-infection with LV containing SS18 and SS18-SSX variants. Error bars=s.d. (C) Hydrophobicity determination using Kyte-Doolittle algorithm for 78 C-terminal amino acids (aa) of SSX1-SSX4 proteins. Region of significant difference highlighted in yellow. (D) Peptide alignment of SSX1-SSX5 C-terminal 78 aa (SEQ ID NOs:1-5). Pink arrows indicate aa of significant difference between SSX1/2/4 and SSX3 or SSX1/2/4 and SSX5; yellow highlight indicates regions determined to be critical for BAF47 ejection. (E) Immunoblot analysis for BAF47 and Brg on anti-GFP IPs of 293T cells transfected with constructs as per above as well as SS18-SSX3; and (F) with SS18-SSX1, 5518-SSX1Δaa43, 44 (KR→MI), SS18-SSX3, 5518-SSX3Δaa43, 44 (MI→KR). See also FIG. 12A. (G) Quantitative densitometry depicting BAF47/Brg protein ratios in IP studies. Error bars=s.d. (H) Sox2 mRNA levels in human fibroblasts day 15 post-infection with LV containing various constructs. See also FIG. 12B. Error bars=s.d.

FIG. 9. (A) BAF47 total protein levels are significantly diminished in synovial sarcoma cells; BAF47 mRNA is comparable across various cell types assayed. (B) Wild-type SS18 protein levels are reduced in synovial sarcoma lines bearing the SS18-SSX fusion; SS18 wild type mRNA levels are also reduced. (C) Brg is localized to the SS18 promoter and an intronic region of the SS18 gene (Ho, L., et al. (2011). esBAF facilitates pluripotency by conditioning the genome for LIF/ STAT3 signalling and by regulating polycomb function. *Nat Cell Biol* 13, 903-913). (D) Glycerol gradient sedimentation analyses of both Aska-SS and Yamato-SS synovial sarcoma cell types. SS18 immunoblot on Aska cells (A) and Yamato cells (Y). L, ladder. (E) Quantitative densitometry of overexposed anti-SS18 immunoblot of Aska-SS monomeric (fx 3-6) and Brg-containing glycerol gradient fractions (fx 14-17). Error bars indicate s.d.

Figure 10:
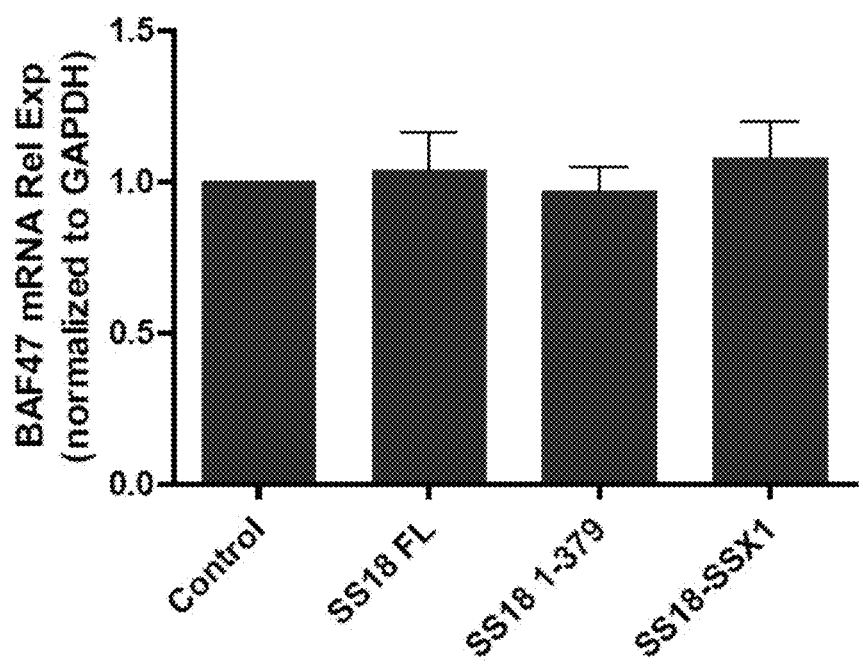

FIG. 10. BAF47 mRNA levels are comparable in cells transfected with SS18 and SS18-SSX variants, BAF47 mRNA levels at time t=72 hours post transfection with either empty vector control, SS18 FL (wild-type), SS18 1-379 (minus last 8 aa of SS18 Ctemminus), or SS18-SSX1. Error bars indicate s.d.

Figure 11:
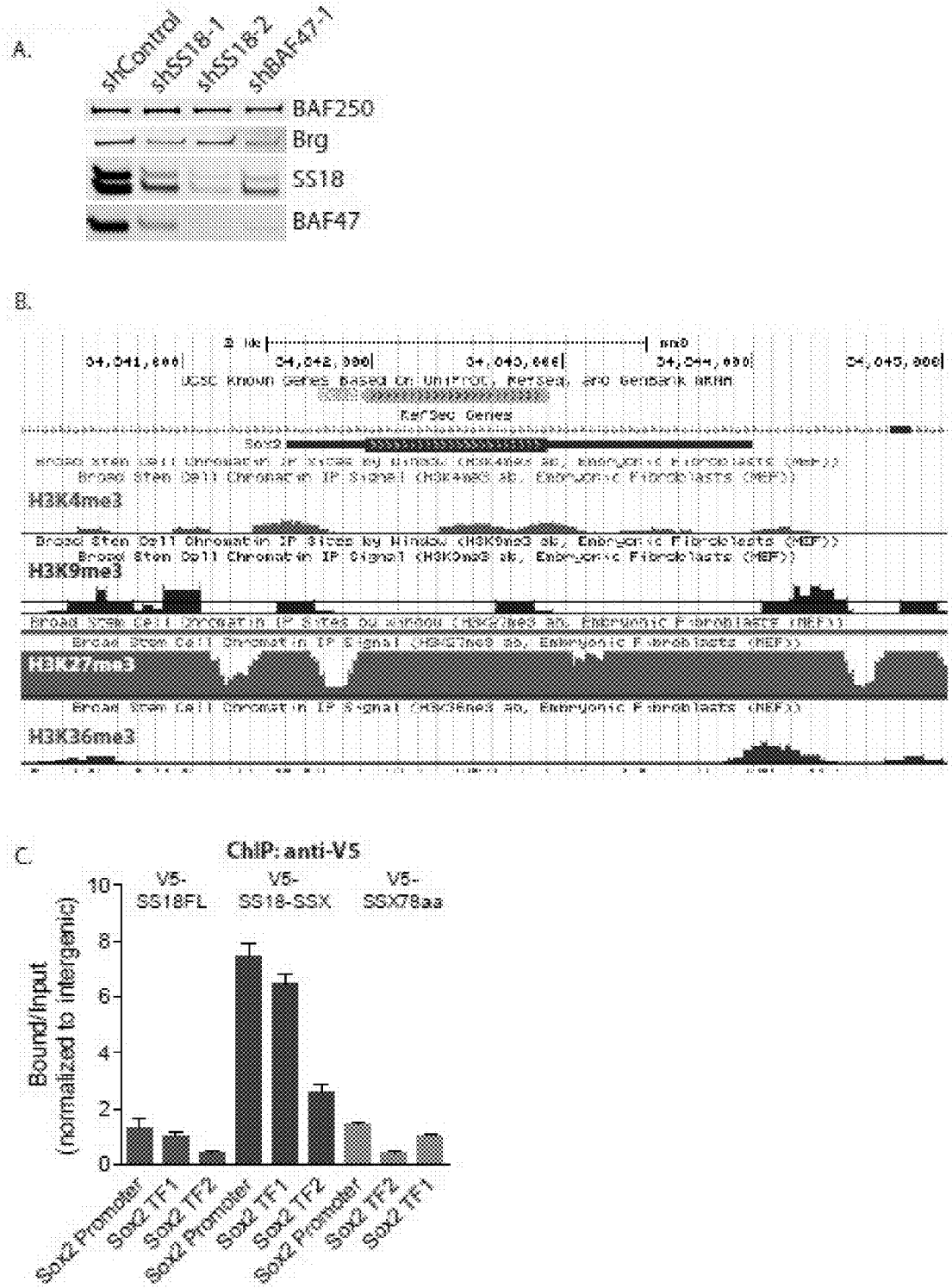

FIG. 11. (A) Reciprocal protein downregulation of SS18 and BAF47 upon shRNA-mediated KD. (B) ChIP-seq tracks of histone marks over the Sox2 locus in MEFs (Mikkelsen, T. S., et al. (2007). Genome-wide maps of chromatin state in pluripotent and lineage-committed cells. *Nature* 448, 553-560). (C) Anti-V5 ChIP analyses of V5-tagged SS18, SS18-SSX1, and SSX (78 aa tail) at three sites of the human Sox2 locus. Error bars indicate s.d.

Figure 12:
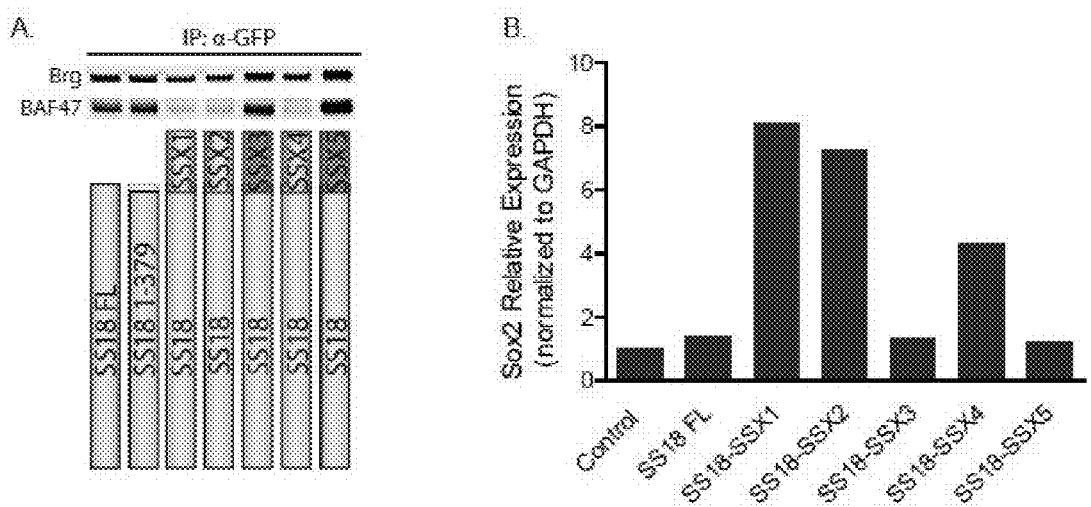

FIG. 12. SS18-SSX1, 2, 4 but not SS18-SSX3,5 eject BAF47 from BAF complexes and induce Sox2mRNA expression.
(A) Anti-GFP IP studies performed in 2931 cells transfected with SS18 FL, SS18 1-379, and SS18-SSX1-5 variants.
(B) Sox2 mRNA levels in human fibroblasts infected with SS18 and SS18-SSX1-5 variants.

Figure 13:
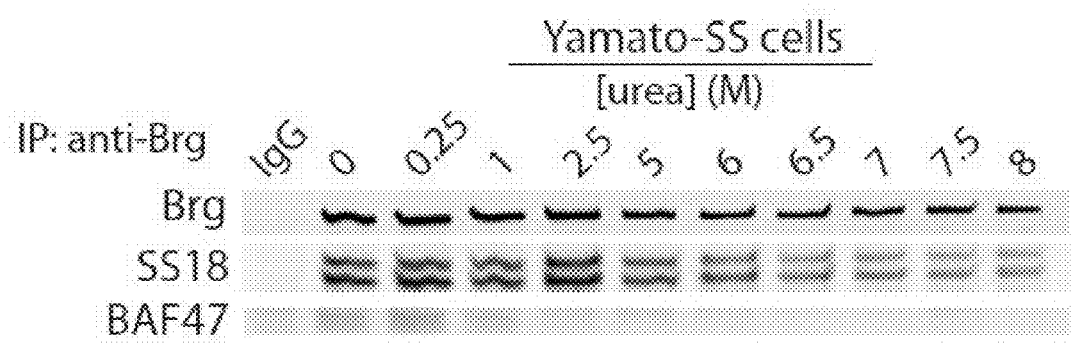

FIG. 13. Urea denaturation analysis on Yamato-SS synovial sarcoma cells. Urea series, 0M<[urea]<8M.

DETAILED DESCRIPTION OF THE INVENTION

Methods and compositions are provided for treating synovial sarcoma (SS) in an individual having synovial sarcoma. Also provided are screens to identify therapeutics for the treatment of synovial sarcoma. These and other objects, advantages, and features of the invention will become apparent to those persons skilled in the art upon reading the details of the compositions and methods as more fully described below.

Before the present methods and compositions are described, it is to be understood that this invention is not limited to particular method or composition described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supercedes any disclosure of an incorporated publication to the extent there is a contradiction.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

It must be noted that as used herein and in the appended claims, the singular forms "a", "an", and "the" include plural referents unless the context clearly dictates otherwise. Thus, for example, reference to "a cell" includes a plurality of such cells and reference to "the peptide" includes reference to one or more peptides and equivalents thereof, e.g. polypeptides, known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.
Methods and Compositions In some aspects of the invention, methods and compositions are provided for promoting the formation of wild type BAF complexes in cells. These methods and compositions find a number of uses, including in medicine in the treatment of human synovial sarcoma (SS) in an individual having human synovial sarcoma (SS), and in research, in the identification of candidate agents that treat synovial sarcoma. By a "synovial sarcoma" it is meant a soft tissue sarcoma that is associated with the translocation event t(X;18)(p11.2;q11.2), which fuses the coding sequence for the first 379 amino acids of the SS18 gene on chromosome 18 to the coding sequence for the last 78 amino acids one of three closely related genes—SSX1, SSX2, or SSX4—on the X chromosome. In other words, the C-terminal 78 amino acids of SSX1, SSX2, or SSX4 become fused to SS18 at residue 379. See, e.g., FIG. 2 herein. In some embodiments, the synovial sarcoma that is treated by the methods and compositions herein is associated with a translocation that results in the fusion of the SS18 gene to the SSX1 gene. In some embodiments, the synovial sarcoma is associated with a translocation that results in the fusion of the SS18 gene to the SSX2 gene. In some embodiments, the synovial sarcoma is associated with a translocation that results in the fusion of the SS18 gene to the SSX4 gene.

The terms "treatment", "treating" and the like are used herein to generally mean obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease in a mammal, and includes: (a) preventing the disease from occurring in a subject which may be predisposed to the disease but has not yet been diagnosed as having it; (b) inhibiting the disease, i.e., arresting its development; or (c) relieving the disease, i.e., causing regression of the disease. The therapeutic agent may be administered before, during or after the onset of disease or injury. The treatment of ongoing disease, where the treatment stabilizes or reduces the undesirable clinical symptoms of the patient, is of particular interest. Such treatment is desirably performed prior to complete loss of function in the affected tissues. The subject therapy will desirably be administered during the symptomatic stage of the disease, and in some cases after the symptomatic stage of the disease.

The terms "individual," "subject," "host," and "patient," are used interchangeably herein and refer to any mammalian subject for whom diagnosis, treatment, or therapy is desired, particularly humans.

In some aspects of the methods, the methods comprise contacting a cell, e.g. a synovial sarcoma cell, with an agent in an amount effective to promote the formation of wild type BAF complexes. By "BAF complexes" (also called mSWI/SNF, for mammalian SWItch/Sucrose NonFermentable, complexes), it is meant ATP-dependent chromatin remodeling complexes comprising proteins encoded by the SWI/SNF genes and other polypeptides, e.g. SMARCA4 (BRG1), SMARCA2 (BRM), ARID1A (BAF250A), ARID1B (BAF250B), ARID2 (BAF200), PBRM1 (BAF180), BCL11A, BCL11B, BCL7A, BCL7B, BCL7C, SMARCB1 (BAF47), SMARCD1 (BAF60A), SMARCD2 (BAF60B), SMARCD3 (BAF60c), SMARCC1 (BAF155), SMARCC2 (BAF170), PHF10 (BAF45A), DPF1 (BAF45B), DPF2 (BAF45C), DPF3 (BAF45D), ACTL6A (BAF53A), ACTL6B (BAF53B), BRD9, BRD7, SS18, CREST (SS18L1), and SMARCE1 (BAF57), that remodel the way DNA is packaged. The interaction of the SWI/SNF complex with chromatin modulates the binding of transcription factors to that chromatin and the transcriptional activity at those loci. By "wild type BAF complexes", it is meant BAF complexes comprising wild type SS18 polypeptide and BAF47, including other associated factors and subunits known to be associated with wild type (non-SS18-SSX containing) complexes, e.g. SMARCA4 (BRG1), SMARCA2 (BRM), ARID1A (BAF250A), ARID1B (BAF250B), ARID2 (BAF200), PBRM1 (BAF180), BCL11A, BCL11B, BCL7A, BCL7B, BCL7C, SMARCB1 (BAF47), SMARCD1 (BAF60A), SMARCD2 (BAF60B), SMARCD3 (BAF60c), SMARCC1 (BAF155), SMARCC2 (BAF170), PHF10 (BAF45A), DPF1 (BAF45B), DPF2 (BAF45C), DPF3 (BAF45D), ACTL6A (BAF53A), ACTL6B (BAF53B), BRD9, BRD7, SS18, CREST (SS18L1), and SMARCE1 (BAF57) polypeptide. This is in contrast to "mutant BAF complexes", which comprise SS18-SSX polypeptide. do not comprise BAF47, and comprise other BAF subunits in altered stoichiometries. By an "effective amount" of agent it is meant an amount of agent that is effective in promoting the formation of wild type BAF complexes and, hence, suppressing the proliferation of SS cells. The formation of wild type BAF complexes and/or the suppression of proliferation of SS cells may be readily assessed using any convenient method, e.g. as known in the art or as described herein. For example, sarcoma mass may be measured, where a decrease or cessation in the rate of sarcoma mass growth is indicative of an effective amount of agent.

Any agent that promotes the formation of wild type BAF complexes in cells, e.g. as known in the art, as described herein, or as identified using the screening methods described herein, may be employed in the subject methods and compositions. Agents that promote the formation of wild type BAF complexes may be readily validated as such by, for example, assessing the number of wild type BAF complexes in the cell; by assessing the amount of BAF47 protein in SS cells, where an increase in BAF47 protein following treatment indicates that the agent promotes the formation of wild type BAF complexes; or by assessing the level of Ink4a or Sox2 RNA or protein in SS cells, where an increase in the amount of Ink4a RNA/protein or a decrease in the amount of Sox2 RNA/protein following treatment indicates that the agent promotes the formation of wild type BAF complexes.

In some embodiments, the subject agent is a nucleic acid. In some embodiments, the subject agent is a polypeptide. In some embodiments, the subject agent is a small molecule. In some embodiments, the subject agent increases the relative amount of wild type BAF47 in the cell. In certain embodiments, the agent is a wild-type BAF47 polypeptide or a nucleic acid that encodes a wild-type BAF47 polypeptide. In certain embodiments, the subject agent increases the relative amount of wild type SS18 polypeptide in the cell. By an "SS18 polypeptide", it is meant the SS18 polypeptide (also known as SSXT and SYT) of the BAF complex, the sequence for which may be found at GenBank Accession Nos. NM_001007559.1 (isoform 1) and NM_005637.2 (isoform 2). In some such embodiments, the subject agent is a wild type SS18 polypeptide or active fragment thereof, or a nucleic acid that encodes a wild type SS18 polypeptide or active fragment thereof. In certain embodiments, the subject agent decreases the relative amount of SS18-SSX fusion protein in the cell. In some such embodiments, the subject agent is a nucleic acid inhibitor that is specific for an SS18-SSX fusion transcript, for example, an antisense RNA, antigomer RNA, siRNA, shRNA, CRISPRi (see, e.g., Qi, L. S. et al. (2013) Cell 152 (5):1173-83), etc. By "specific", "specific binding," "specifically bind," and the like, it is meant the ability of a binding agent, e.g. nucleic acid, polypeptide, antibody, etc., to preferentially bind directly to a target molecule relative to other molecules or moieties in the cell. In certain embodiments, the affinity between the binding agent and the target to which it specifically binds when they are specifically bound to each other in a binding complex is characterized by a KD (dissociation constant) of less than $10^{-6}$ M, less than $10^{-7}$ M, less than $10^{-8}$ M, less than $10^{-9}$ M, less than $10^{-10}$ M, less than $10^{-11}$ M, less than $10^{-12}$ M, less than $10^{-13}$ M, less than $10^{-14}$ M, or less than $10^{-15}$ M. In some certain embodiments, the nucleic acid inhibitor is specific for the SSX 3'UTR, e.g. the 3'UTR of SSX1, the 3'UTR of SSX2, the 3'UTR of SSX4.

The subject agent may be employed to promote the formation of wild type BAF complexes in cells in vitro or in vivo. For example, in some aspects of the methods, the methods comprise contacting a cell with a subject agent, e.g. as a candidate agent, in vitro, for research purposes, e.g. to identify novel therapeutics that promote the formation of wild type BAF complexes and treat synovial sarcoma. In some aspects of the methods, the methods comprise contacting a cell with an agent in vivo, e.g. administering to the individual having a synovial sarcoma (SS) an effective amount of an agent that promotes the formation of wild type BAF complexes and treat synovial sarcoma. These methods are based on the discovery that promoting the assembly of wild type BAF (also called mSWI/SNF) complexes in SS cells leads to the cessation of proliferation of malignant cells in synovial sarcoma.

Cells to be contacted may be from or in any mammalian species, e.g. murine, rodent, canine, feline, equine, bovine, ovine, primate, human, etc. When performing the subject methods in vitro, cells may be from established cell lines or they may be primary cells, where "primary cells", "primary cell lines", and "primary cultures" are used interchangeably herein to refer to cells and cells cultures that have been derived from a subject and allowed to grow in vitro for a limited number of passages, i.e. splittings, of the culture. For example, primary cultures are cultures that may have been passaged 0 times, 1 time, 2 times, 4 times, 5 times, 10 times, or 15 times, but not enough times go through the crisis stage. Typically, the primary cell lines of the present invention are maintained for fewer than 10 passages in vitro.

If the cells are primary cells, they may be harvest from an individual by any convenient method. For example, cells, e.g. skin, muscle, bone marrow, spleen, liver, pancreas, lung, intestine, stomach tissue, etc. may be harvested by biopsy. Of particular interest are cells of muscle, fat, fibrous tissue, blood vessels, or other supporting tissue of the body, including synovial tissue, from which synovial sarcomas more usually arise. An appropriate solution may be used for dispersion or suspension of the harvested cells. Such solution will generally be a balanced salt solution, e.g. normal saline, PBS, Hank's balanced salt solution, etc., conveniently supplemented with fetal calf serum or other naturally occurring factors, in conjunction with an acceptable buffer at low concentration, generally from 5-25 mM. Convenient buffers include HEPES, phosphate buffers, lactate buffers, etc. The cells may be used immediately, or they may be stored, frozen, for long periods of time, being thawed and capable of being reused. In such cases, the cells will usually be frozen in 10% DMSO, 50% serum, 40% buffered medium, or some other such solution as is commonly used in the art to preserve cells at such freezing temperatures, and thawed in a manner as commonly known in the art for thawing frozen cultured cells.

To promote the formation of wild type BAF complexes, the subject agent is provided to the cells for about 30 minutes to about 24 hours, e.g., 1 hour, 1.5 hours, 2 hours, 2.5 hours, 3 hours, 3.5 hours 4 hours, 5 hours, 6 hours, 7 hours, 8 hours, 12 hours, 16 hours, 18 hours, 20 hours, or any other period from about 30 minutes to about 24 hours, which may be repeated with a frequency of about every day to about every 4 days, e.g., every 1.5 days, every 2 days, every 3 days, or any other frequency from about every day to about every four days. The agent(s) may be provided to the subject cells one or more times, e.g. one time, twice, three times, or more than three times, and the cells allowed to incubate with the agent(s) for some amount of time following each contacting event e.g. 16-24 hours, after which time the media is replaced with fresh media and the cells are cultured further.

Typically, an effective amount of subject agent is provided to the cells. By an effective amount, it is meant the amount to induce a 2-fold increase or more in the number of wild type BAF complexes that form in the cell relative to a negative control, e.g. a cell not contacted with agent, or contacted with a negative control. That is to say, an effective amount or dose of subject agent will induce a 2-fold increase, a 3-fold increase, a 4-fold increase or more in the number of wild type BAF complexes in the cell, in some instances a 5-fold increase, a 6-fold increase or more, sometimes a 7-fold or 8-fold increase or more, e.g. an increase of 10-fold, 50-fold, or 100-fold or more, in some instances, an increase of 200-fold, 500-fold, 700-fold, or 1000-fold or more, e.g. a 5000-fold, or 10,000-fold increase in the number of wild type BAF complexes observed. The number of wild type BAF complexes may be measured by any convenient method, e.g. as known in the art or as described herein.

Contacting the cells with the subject agent may occur in any culture media and under any culture conditions that promote the survival of the cells. For example, cells may be suspended in any appropriate nutrient medium that is convenient, such as Iscove's modified DMEM or RPMI 1640, supplemented with fetal calf serum or heat inactivated goat serum (about 5-10%), L-glutamine, a thiol, particularly 2-mercaptoethanol, and antibiotics, e.g. penicillin and streptomycin. The culture may contain growth factors to which the cells are responsive. Growth factors, as defined herein, are molecules capable of promoting survival, growth and/or differentiation of cells, either in culture or in the intact tissue, through specific effects on a transmembrane receptor. Growth factors include polypeptides and non-polypeptide factors.

When performing the subject methods in vivo, the subject agent that promotes the formation of wild type BAF complexes is administered directly to the individual. The subject agent may be administered by any of a number of well-known methods in the art for the administration of polypeptides, small molecules, or nucleic acids to a subject. The subject agent can be incorporated into a variety of formulations. More particularly, subject agent can be formulated into pharmaceutical compositions by combination with appropriate pharmaceutically acceptable carriers or diluents.

Pharmaceutical preparations are compositions that include one or more of the subject agents present in a pharmaceutically acceptable vehicle. "Pharmaceutically acceptable vehicles" may be vehicles approved by a regulatory agency of the Federal or a state government or listed in the U.S. Pharmacopeia or other generally recognized pharmacopeia for use in mammals, such as humans. The term "vehicle" refers to a diluent, adjuvant, excipient, or carrier with which a compound of the invention is formulated for administration to a mammal. Such pharmaceutical vehicles can be lipids, e.g. liposomes, e.g. liposome dendrimers; liquids, such as water and oils, including those of petroleum, animal, vegetable or synthetic origin, such as peanut oil, soybean oil, mineral oil, sesame oil and the like, saline; gum acacia, gelatin, starch paste, talc, keratin, colloidal silica, urea, and the like. In addition, auxiliary, stabilizing, thickening, lubricating and coloring agents may be used. Pharmaceutical compositions may be formulated into preparations in solid, semi-solid, liquid or gaseous forms, such as tablets, capsules, powders, granules, ointments, solutions, suppositories, injections, inhalants, gels, microspheres, and aerosols. As such, administration of the subject agent can be achieved in various ways, including oral, buccal, rectal, parenteral, intraperitoneal, intradermal, transdermal, intracheal, etc., administration. The active agent may be systemic after administration or may be localized by the use of regional administration, intramural administration, or use of an implant that acts to retain the active dose at the site of implantation. The active agent may be formulated for immediate activity or it may be formulated for sustained release.

For some conditions, particularly central nervous system conditions, it may be necessary to formulate the subject agent to cross the blood-brain barrier (BBB). One strategy for drug delivery through the blood-brain barrier (BBB) entails disruption of the BBB, either by osmotic means such as mannitol or leukotrienes, or biochemically by the use of vasoactive substances such as bradykinin. The potential for using BBB opening to target specific agents to brain tumors is also an option. A BBB disrupting agent can be co-administered with the therapeutic compositions of the invention when the compositions are administered by intravascular injection. Other strategies to go through the BBB may entail the use of endogenous transport systems, including Caveolin-1 mediated transcytosis, carrier-mediated transporters such as glucose and amino acid carriers, receptor-mediated transcytosis for insulin or transferrin, and active efflux transporters such as p-glycoprotein. Active transport moieties may also be conjugated to the therapeutic compounds for use in the invention to facilitate transport across the endothelial wall of the blood vessel. Alternatively, drug delivery of therapeutics agents behind the BBB may be by local delivery, for example by intrathecal delivery, e.g. through an Ommaya reservoir (see e.g. U.S. Pat. Nos. 5,222,982 and 5,385,582, incorporated herein by reference); by bolus injection, e.g. by a syringe, e.g. intravitreally or intracranially; by continuous infusion, e.g. by cannulation, e.g. with convection (see e.g. US Application No. 20070254842, incorporated here by reference); or by implanting a device upon which the agent has been reversably affixed (see e.g. US Application Nos. 20080081064 and 20090196903, incorporated herein by reference).

Typically, an effective amount of the subject agent is provided. As discussed above with regard to in vitro methods, an effective amount or effective dose of a subject agent in vivo is the amount to induce a 2 fold increase or more in the number of wild type BAF complexes in the contacted cell(s) relative to a negative control, e.g. an individual not administered the subject agent. Because an increase in the number of wild type BAF complexes will suppress the proliferation of synovial sarcoma (SS) cells in the individual, measuring the proliferation of SS cells and the rate of SS tumor growth may be used as a surrogate biomarker to determine that an effective amount of subject agent has been administered. For example, sarcoma mass may be measured, where a decrease or cessation in the rate of sarcoma mass growth is indicative of an effective amount of agent.

The calculation of the effective amount or effective dose of a subject agent to be administered is within the skill of one of ordinary skill in the art, and will be routine to those persons skilled in the art. Needless to say, the final amount to be administered will be dependent upon the route of administration and upon the nature of the disorder or condition that is to be treated. The effective amount given to a particular patient will depend on a variety of factors, several of which will differ from patient to patient. A competent clinician will be able to determine an effective amount of a therapeutic agent to administer to a patient to halt or reverse the progression the disease condition as required. Utilizing $LD_{50}$ animal data, and other information available for the agent, a clinician can determine the maximum safe dose for an individual, depending on the route of administration. For instance, an intravenously administered dose may be more than an intrathecally administered dose, given the greater body of fluid into which the therapeutic composition is being administered. Similarly, compositions which are rapidly cleared from the body may be administered at higher doses, or in repeated doses, in order to maintain a therapeutic concentration. Utilizing ordinary skill, the competent clinician will be able to optimize the dosage of a particular therapeutic in the course of routine clinical trials.

For inclusion in a medicament, the subject agent may be obtained from a suitable commercial source. As a general proposition, the total pharmaceutically effective amount of the subject agent administered per dose will be in a range that can be measured by a dose response curve.

Pharmaceutical compositions comprising the subject agent, i.e. preparations of subject agent to be used for therapeutic administration, must be sterile. Sterility is readily accomplished by filtration through sterile filtration membranes (e.g., 0.2 μm membranes). Therapeutic compositions generally are placed into a container having a sterile access port, for example, an intravenous solution bag or vial having a stopper pierceable by a hypodermic injection needle. The subject pharmaceutical compositions may be stored in unit or multi-dose containers, for example, sealed ampules or vials, as an aqueous solution or as a lyophilized formulation for reconstitution. As an example of a lyophilized formulation, 10-mL vials are filled with 5 ml of sterile-filtered 1% (w/v) aqueous solution of compound, and the resulting mixture is lyophilized. The infusion solution is prepared by reconstituting the lyophilized compound using bacteriostatic Water-for-Injection.

Pharmaceutical compositions can include, depending on the formulation desired, pharmaceutically-acceptable, non-toxic carriers of diluents, which are defined as vehicles commonly used to formulate pharmaceutical compositions for animal or human administration. The diluent is selected so as not to affect the biological activity of the combination. Examples of such diluents are distilled water, buffered water, physiological saline, PBS, Ringer's solution, dextrose solution, and Hank's solution. In addition, the pharmaceutical composition or formulation can include other carriers, adjuvants, or non-toxic, nontherapeutic, nonimmunogenic stabilizers, excipients and the like. The compositions can also include additional substances to approximate physiological conditions, such as pH adjusting and buffering agents, toxicity adjusting agents, wetting agents and detergents. The composition can also include any of a variety of stabilizing agents, such as an antioxidant for example. When the pharmaceutical composition includes a polypeptide, the polypeptide can be complexed with various well-known compounds that enhance the in vivo stability of the polypeptide, or otherwise enhance its pharmacological properties (e.g., increase the half-life of the polypeptide, reduce its toxicity, enhance solubility or uptake). Examples of such modifications or complexing agents include sulfate, gluconate, citrate and phosphate. The nucleic acids or polypeptides of a composition can also be complexed with molecules that enhance their in vivo attributes. Such molecules include, for example, carbohydrates, polyamines, amino acids, other peptides, ions (e.g., sodium, potassium, calcium, magnesium, manganese), and lipids.

Further guidance regarding formulations that are suitable for various types of administration can be found in Remington's Pharmaceutical Sciences, Mace Publishing Company, Philadelphia, Pa., 17th ed. (1985). For a brief review of methods for drug delivery, see, Langer, Science 249:1527-1533 (1990).

The pharmaceutical compositions can be administered for prophylactic and/or therapeutic treatments. Toxicity and therapeutic efficacy of the active ingredient can be determined according to standard pharmaceutical procedures in cell cultures and/or experimental animals, including, for example, determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Therapies that exhibit large therapeutic indices are preferred.

The data obtained from cell culture and/or animal studies can be used in formulating a range of dosages for humans. The dosage of the active ingredient typically lines within a range of circulating concentrations that include the ED50 with low toxicity. The dosage can vary within this range depending upon the dosage form employed and the route of administration utilized.

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are usually sterile. To the extent that a given compound must be synthesized prior to use, the resulting product is typically substantially free of any potentially toxic agents, particularly any endotoxins, which may be present during the synthesis or purification process. Compositions for parental administration are also sterile, substantially isotonic and made under GMP conditions. The effective amount of a therapeutic composition to be given to a particular patient will depend on a variety of factors, several of which will differ from patient to patient. A competent clinician will be able to determine an effective amount of a therapeutic agent to administer to a patient to halt or reverse the progression the disease condition as required. Utilizing LD50 animal data, and other information available for the agent, a clinician can determine the maximum safe dose for an individual, depending on the route of administration. For instance, an intravenously administered dose may be more than an intrathecally administered dose, given the greater body of fluid into which the therapeutic composition is being administered. Similarly, compositions which are rapidly cleared from the body may be administered at higher doses, or in repeated doses, in order to maintain a therapeutic concentration. Utilizing ordinary skill, the competent clinician will be able to optimize the dosage of a particular therapeutic in the course of routine clinical trials.

In some embodiments, the method further comprises the step of diagnosing the individual as having a synovial sarcoma. Any convenient method known in the art or described herein may be used to diagnose a synovial sarcoma. For example, as discussed above, synovial sarcomas are associated with a t(X;18)(p11.2;q11.2) translocation event. Accordingly, a cytogenetics assay, e.g. a chromosomal analysis, e.g. chromosomal smear, may be used in diagnosing a synovial sarcoma. As a second example, although synovial sarcomas have been documented in most human tissues and organs including brain, prostate, and heart synovial sarcomas have a propensity to arise adjacent to joints, e.g. large joints of the arm and leg. As such, the detection of a sarcoma in a joint, e.g. a large joint of the arm or leg, may be used in diagnosing a synovial sarcoma. As a third example, synovial sarcomas comprise 2 types of cells. The first type, known as a spindle or sarcomatous cell, is relatively small and uniform, and found in sheets. The other is epithelial in appearance. Classical synovial sarcoma has a biphasic appearance with both types present. Synovial sarcoma can also appear to be poorly differentiated or to be monophasic fibrous, consisting only of sheets of spindle cells. As such, a histological analysis of an SS biopsy may be used in diagnosing a synovial sarcoma.

In some embodiments, the method further comprises administering a second synovial sarcoma treatment to the subject. For example, the method may comprise administering chemotherapy, e.g. doxorubicin hydrochloride, ifosfamide, radiotherapy, and the like. Any therapeutic known in the art for the treatment of cancers, e.g. soft tissue cancers, may be administered. In some instances, the therapy may be administered before the agent that promotes the formation of wild type BAF complexes. In some instances, the therapy may be administered after the agent that promotes the formation of wild type BAF complexes. In some instances, the therapy may be administered concurrently with the agent that promotes the formation of wild type BAF complexes.

Utility

As discussed above, the subject methods and compositions find a number of uses, including in medicine in the treatment of human synovial sarcoma (SS) in an individual having human synovial sarcoma (SS), and in research, in the identification of candidate agents that treat synovial sarcoma.

By a "synovial sarcoma" it is meant a soft tissue sarcoma that is associated with the translocation event t(X;18)(p11.2;q11.2), which fuses the coding sequence for the first 379 amino acids of the SS18 gene on chromosome 18 to the coding sequence for the last 78 amino acids one of three closely related genes—SSX1, SSX2, or SSX4—on the X chromosome. In other words, the C-terminal 78 amino acids of SSX1, SSX2, or SSX4 become fused to SS18 at residue 379. See, e.g., FIG. 2 herein.

Individuals having a synovial sarcoma may be readily identified in any of a number of ways. For example, a cytogenetics assay, e.g. a chromosomal analysis, e.g. chromosomal smear, may be used in diagnosing a synovial sarcoma. As a second example, although synovial sarcomas have been documented in most human tissues and organs including brain, prostate, and heart synovial sarcomas have a propensity to arise adjacent to joints, e.g. large joints of the arm and leg. As such, the detection of a sarcoma in a joint, e.g. a large joint of the arm or leg, may be used in diagnosing a synovial sarcoma. As a third example, synovial sarcomas comprise 2 types of cells. The first type, known as a spindle or sarcomatous cell, is relatively small and uniform, and found in sheets. The other is epithelial in appearance. Classical synovial sarcoma has a biphasic appearance with both types present. Synovial sarcoma can also appear to be poorly differentiated or to be monophasic fibrous, consisting only of sheets of spindle cells. As such, a histological analysis of an SS biopsy may be used in diagnosing a synovial sarcoma.

The subject methods and compositions may be used to treat human synovial sarcoma (SS) in an individual having human synovial sarcoma (SS). For example the administration of the subject agents for a suitable period of time, usually at least about one week, and maybe about two weeks, or more, up to a period of about 4 weeks, 8 weeks, or longer will evidence an alteration in the symptoms associated with reduced amounts of wild type BAF complexes in SS cells. For example, an effective dose is the dose that when administered for a suitable period of time, usually at least about one week, and may be about two weeks, or more, up to a period of about 4 weeks, 8 weeks, or longer will slow or even halt tumor growth in a patient suffering from synovial sarcoma. In some embodiments, an effective dose may not only slow or halt the progression of the disease condition but may also induce the reversal of the condition. For example, an effective dose of the subject agent will not only halt tumor growth in a synovial sarcoma patient, but will reduce the size of the tumor(s). It will be understood by those of skill in the art that an initial dose may be administered for such periods of time, followed by maintenance doses, which, in some cases, will be at a reduced dosage.

Screens

In some aspects of the invention, methods are provided for screening a candidate agent for the ability to treat an individual having a synovial sarcoma, e.g., for use in the methods described herein. In these methods, a candidate agent is identified that promotes the assembly of wild-type BAF complexes in the presence of SS18-SSX fusion protein, where an agent that promotes the assembly of wild-type BAF complexes in the presence of SS18-SSX fusion protein will treat synovial sarcoma. These methods are based upon the inventors' discovery that incorporation of the SS18-SSX fusion protein into the BAF complex leads to the eviction of BAF47 from the complex and its subsequent destabilization and proteasome-mediated degradation. Conversely, agents that promote the assembly of wild type complexes promote the incorporation of wild type SS18 and BAF47, which prevents BAF47 degradation and restores wild type BAF complex activity, including, for example, appropriate regulation of the Ink4a and Sox2 promoters. As a result, appropriate formation of the BAF complex, increases in total cellular BAF47 protein levels, increases in Ink4a promoter activity, and decreases in Sox2 promoter activity may be used as read-outs to identify agents that promote the assembly of wild type BAF complex in cells. In some embodiments, the screen is a cell-free screen. In other embodiments, the screen is a cell-based screen, i.e. the screen uses cells that express proteins of interest.

In some embodiments, the screening method comprises contacting a cell comprising an SS18-SSX fusion protein with a candidate agent, and assessing the effect of the candidate agent on the cell by monitoring one or more cellular parameters. Parameters are quantifiable components of cells, particularly components that can be accurately measured, desirably in a high throughput system. A parameter can be any cell component or cell product including cell surface determinant, receptor, protein or conformational or posttranslational modification thereof, lipid, carbohydrate, organic or inorganic molecule, nucleic acid, e.g. mRNA, DNA, etc. or a portion derived from such a cell component or combinations thereof. While most parameters will provide a quantitative readout, in some instances a semi-quantitative or qualitative result will be acceptable. Readouts may include a single determined value, or may include mean, median value or the variance, etc. Characteristically a range of parameter readout values will be obtained for each parameter from a multiplicity of the same assays. Variability is expected and a range of values for each of the set of test parameters will be obtained using standard statistical methods with a common statistical method used to provide single values. Thus, for example, one such method may comprise contacting a cell that expresses SS18-SSX with a candidate agent; and comparing the parameter to the parameter in a cell that expresses SS18-SSX but was not contacted with the candidate agent, wherein a difference in the parameter in the cell contacted with the candidate agent indicates that the candidate agent will treat SS. In some instances, one parameter is measured. In some instances, multiple parameters are measured.

Examples of cellular parameters that may be detected in the subject screens include the relative stoichiometry, abundance, binding, or assembly of one or more BAF subunits into the BAF complex, wherein the reestablishment of wild type stoichiometry, abundance, binding, or assembly indicates that the candidate agent promotes the assembly of wild type BAF complexes. For example, the amount of subunit in the cell may be quantified, wherein an increase in the amount of subunit in the cell as compared to in a cell not contacted with candidate agent indicates that the candidate agent promotes the assembly of wild-type BAF complexes. BAF subunits are well known in the art, and include, for example, SMARCA4 (BRG1), SMARCA2 (BRM), ARID1A (BAF250A), ARID1B (BAF250B), ARID2 (BAF200), PBRM1 (BAF180), BCL11A, BCL11B, BCL7A, BCL7B, BCL7C, SMARCB1 (BAF47), SMARCD1 (BAF60A), SMARCD2 (BAF60B), SMARCD3 (BAF60c), SMARCC1 (BAF155), SMARCC2 (BAF170), PHF10 (BAF45A), DPF1 (BAF45B), DPF2 (BAF45C), DPF3 (BAF45D), ACTL6A (BAF53A), ACTL6B (BAF53B), BRD9, BRD7, SS18, CREST (SS18L1), and SMARCE1 (BAF57).

For example, the amount of BAF47 polypeptide in the cell may be quantified, wherein an increase in the amount of BAF47 polypeptide in the cell as compared to in a cell not contacted with candidate agent indicates that the candidate agent promotes the assembly of wild-type BAF complexes. As such, the method may comprise contacting a cell comprising an SS18-SSX fusion protein with a candidate agent, and detecting the amount of BAF47 polypeptide in the cell, wherein an increase in the amount of BAF47 polypeptide in the cell as compared to in a cell not contacted with candidate agent indicates that the candidate agent promotes the assembly of wild-type BAF complexes. By a "BAF47 polypeptide" it is meant a polypeptide that associates with SS18, Brg, and other polypeptides to form wild type BAF complexes. The sequence for BAF47 (also known as hSNF5, INI1, and SMARCB1) may be found at GenBank Accession No. NM_003073.3 (isoform a) or NM_001007468.1 (isoform b)).

In some embodiments, the detecting step comprises detecting the amount of BAF subunit, e.g. BAF47, polypeptide in the cell with an agent that is specific for the subunit, e.g. BAF47. By an agent that is specific for a polypeptide subunit, e.g. BAF47, it is meant a composition, e.g. an antibody, a peptide, that is specific for the subunit, e.g. BAF47. In some embodiments, the cell comprises a detectably labeled polypeptide subunit, e.g. BAF47 polypeptide, and the detecting step comprises detecting the detectable label of the subunit, e.g. BAF47 polypeptide. By a "detectable label" it is meant a moiety that may be detected, e.g. a radioactive label, fluorescent label, a label that produces a histochemically or immunohistochemically detectable substance, or detectable dye. Non-limiting examples of detectable labels that may be used to label the subunit, e.g. BAF47, include luciferase, 6-galactosidase (beta-gal), horseradish peroxidase (HRP), a fluorophore or chromophore moiety (e.g. Alexa Fluor 488® or Alexa Fluor 647®), a protein that comprises a fluorophore or chromophore, e.g. GFP, RFP, dsRED, phiYFP, etc. and mutants thereof, and the like. In some instances, the detectable label may require the addition of a substrate for detection, e.g. luciferase, β-galactosidase, horseradish peroxidase (HRP), etc. Alternatively, the detectable label may be detected without the addition of a substrate e.g. a fluorophore or chromophore moiety, a protein that comprises a fluorophore or chromophore, e.g. GFP, RFP, dsRED, phiYFP, etc. and mutants thereof. In some embodiments, the detectable label is covalently bound to the C-terminus of the BAF47 polypeptide. In other embodiments, the detectable label is covalently bound to the N-terminus of the subunit, e.g., BAF47 polypeptide.

Thus, for example, in some embodiments of the method, synovial sarcoma cells comprising BAF47 that has been tagged with a detectable moiety (e.g. firefly luciferase) are contacted with a candidate agent, and the amount of tagged BAF47 is detected. In the absence of an agent that promotes assembly of normal BAF complexes, no (or negligible levels of) tagged BAF47 are detected. In the presence of a candidate agent that promotes assembly of normal BAF complexes, increased levels of tagged BAF47 are detected.

In some embodiments, the method further comprises the step of comparing the amount of polypeptide subunit, e.g. BAF47 polypeptide, detected in the cell contacted by candidate agent to the amount of polypeptide subunit, e.g. BAF47 polypeptide, in a cell contacted with a control. By a "control" or "reference" it is meant an agent that will produce a known result, e.g., that will promote the assembly of wild-type BAF complexes in the presence of SS18-SSX fusion protein (a positive control) or that will not promote the assembly of wild-type BAF complexes in the presence of SS18-SSX fusion protein. In some embodiments, the positive control is an agent selected from the group consisting of a wild type SS18 polypeptide or active fragment thereof, a nucleic acid that encodes a wild type SS18 polypeptide or active fragment thereof, and a nucleic acid inhibitor that is specific for an SS18-SSX fusion transcript selected from the group consisting of antisense RNA, antigomer RNA, siRNA, and shRNA.

Another cellular parameter that may be detected is the activity of the Ink4a promoter or Sox2 promoter, wherein an increase in the amount of Ink4a promoter activity or a decrease in the amount of Sox2 promoter activity in the cell as compared to in a cell not contacted with candidate agent indicates that the candidate agent promotes the assembly of wild-type BAF complexes. In other words, the method comprises contacting a cell comprising an SS18-SSX fusion protein with a candidate agent, and detecting the amount of Ink4a and/or Sox2 promoter activity in the cell, wherein an increase in the amount of Ink4a promoter activity or a decrease in the amount of Sox2 activity in the cell as compared to in a cell not contacted with candidate agent indicates that the candidate agent promotes the assembly of wild-type BAF complexes. As used herein, a "promoter" or "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site, as well as protein binding domains responsible for the binding of RNA polymerase. Eukaryotic promoters will often, but not always, contain "TATA" boxes and "CAT" boxes. By promoter activity it is meant the amount of transcription that is observed of the nucleic acid coding sequence, e.g. an endogenous gene, a reporter, etc., under control of the promoter of interest.

The activity of the Ik4a promoter may be detected using any convenient method for the detection of promoter activity. For example, the amount of Ink4a RNA or Ink4a polypeptide in the cell may be detected, e.g. using RT-PCR with primers that are specific for the Ink4a transcript or an antibody that is specific for the Ink4a polypeptide. Likewise, the amount of Sox2 RNA or Sox2 polypeptide in the cell may be detected, e.g. using RT-PCR with primers that are specific for the Sox2 transcript or an antibody that is specific for the Sox2 polypeptide. As another example, the cell may be engineered to comprise a coding sequence under control of the Ink4a promoter that encodes for an Ink4a polypeptide or fragment thereof fused to a detectable label, and/or a coding sequence under control of the Sox2 promoter that encodes for a Sox2 polypeptide or fragment thereof that is fused to a detectable labeled, wherein the detecting step comprises detecting the detectable label. Any coding sequence for any detectable label, e.g. as described herein or known in the art, may be employed, e.g. luciferase, β-galactosidase, horseradish peroxidase, a chromo- or fluorescent protein, etc. As a third example, the cell may be engineered to comprise a coding sequence under control of the Ink4a promoter that encodes for an Ink4a polypeptide or fragment thereof fused to a selectable marker, and/or a coding sequence under control of the Sox2 promoter that encodes for a Sox2 polypeptide or fragment thereof that is fused to a selectable marker, wherein the detecting step comprises detecting the selectable marker. By a "selectable marker" it is meant a protein that can be selected for in a cell using a drug, e.g. neomycin, etc. As a fourth example, the cell may be engineered to comprise an Ink4a promoter operably linked to a reporter, and/or a Sox2 promoter operably linked to a reporter, wherein the detecting step comprises detecting the reporter(s). As used herein, the term "reporter" or "reporter gene" refers to a coding sequence attached to heterologous promoter or enhancer elements and whose product may be assayed easily and quantifiably when the construct is introduced into tissues or cells.

In some embodiments, the method further comprises the step of comparing the amount of Ink4a promoter activity detected in the cell contacted by candidate agent to the amount of Ink4a promoter activity in a cell contacted with a control, and/or comparing the amount of Sox2 promoter activity detected in the cell contacted by candidate agent to the amount of Sox2 promoter activity in a cell contacted with a control. In certain embodiments, the control is a positive control selected from the group consisting of a wild type SS18 polypeptide or active fragment thereof, a nucleic acid that encodes a wild type SS18 polypeptide or active fragment thereof, and a nucleic acid inhibitor that is specific for an SS18-SSX fusion transcript selected from the group consisting of antisense RNA, antigomer RNA, siRNA, and shRNA.

Cells useful for screening include any cell that expresses the SS18-SSX fusion protein. For example, the cell may endogenously express SS18-SSX. In other words, the cell is a primary synovial sarcoma cell (i.e. isolated from a synovial sarcoma) or is a cell of a cell line generated therefrom, e.g. Aska-SS, Yamato-SS, FU-SY-1, SW-982, HS-SY-II, 1273/99. As another example, the cell may ectopically express SS18-SSX. In other words, the cell is a non-synovial sarcoma cell e.g. a 293 cell, a NIH3T3 cell, a ES cell, a Raji cell, a CCRF-CEM cell, a primary fibroblast or a cell from a cell line generated therefrom, etc., that has been manipulated to express SS18-SSX, e.g. by transformation or infection with a vector comprising a nucleic acid that encodes the SS18-SSX fusion protein, by the introduction of SS18-SSX fusion polypeptide directly into the cell, etc. In some instances, the SS18-SSX is expressed extrachromosomally (e.g. from a minicircle, a cosmid, etc.). In other instances, the SS18-SSX is expressed from the genome of the cell. In some such instances, e.g. as when the SS18-SSX is endogenously expressed by the cell, the SS18-SSX is expressed from the locus of translocation. In other instances, e.g. as when the SS18-SSX is ectopically expressed in the cell, the SS18-SSX is expressed from a locus other than the locus of translocation. The cell may express any SS18-SSX fusion protein that is associated with synovial sarcoma. For example, the cell may express SS18 fused to SSX1. The cell may express SS18 fused to SSX2. The cell may express SS18 fused to SSX2.

In other embodiments, the screening method comprises contacting a mutant BAF complex, i.e. a BAF complex comprising SS18-SSX fusion protein, with a candidate agent in the presence of a polypeptide subunit, e.g. BAF47, and detecting the incorporation of the polypeptide subunit, e.g. BAF47, into the complex. Many methods are known in the art for detecting the association of proteins into a complex. For example, the BAF complex may be bound to a detection bead, e.g. scintillation proximity assay (SPA) bead, and the polypeptide subunit, e.g. BAF47, detectably labeled, e.g. with a radioisotope, wherein the detecting comprises detecting the proximity of the subunit, e.g. BAF47, to the detection bead, e.g. by scintillation proximity assay. As another example, the BAF complex may be tagged with a first moiety, e.g. a first AlphaScreen bead or a FOrster resonance energy transfer (FRET) donor element, and the subunit, e.g. BAF47, tagged with a second moiety, e.g. a second AlphaScreen bead or a FRET acceptor element, wherein the detecting comprises detecting a signal produced by the proximity of the first moiety with the second moiety. As a third example, the BAF complex is tagged with the first moiety and the SS18-SSX fusion protein tagged with the second moiety, wherein the detecting comprises detecting the loss of a signal produced by the proximity of the first moiety with the second moiety.

In other embodiments, the screening method comprises contacting SS18-SSX fusion protein with a candidate agent, and detecting the binding of candidate agent to SS18-SSX fusion protein, wherein an agent that binds SS18-SSX and not wild type SS18 will promote the assembly of wild-type BAF complexes in the presence of SS18-SSX fusion protein. Methods for detecting binding of an agent to a protein are well known in the art, any of which may be used in such screens. For example, the SS18-SSX may be bound to a solid support, and the binding of agent to the SS18-SSX fusion protein detected by surface plasmon resonance, e.g. biacore. In some embodiments, the method further comprises contacting wild type SS18 protein with the candidate agent, and detecting the binding of candidate agent to wild type SS18 protein.

In some embodiments, the identification of a candidate agent having therapeutic use relies upon the use of a multiwell plate. For example, the contacting of cells may occur in a multiwell plate, the contacting of a mutant BAF complex with candidate agent may occur in a multiwell plate, etc. By a "multiwell plate" it is meant a dish made, for example, of polystyrene, polypropylene, or other plastic compound that comprises wells. In some embodiments, the multiwell plate is a 24-well plate. In some embodiments, the multiwell plate is a 96-well plate. In some embodiments, the multiwell plate is a 384-well plate. In some embodiments, the multiwell plate is a 1536-well plate. In some embodiments, the multiwell plate is a 3456-well dish.

Candidate agents of interest for screening include known and unknown compounds that encompass numerous chemical classes, primarily organic molecules, which may include organometallic molecules, inorganic molecules, genetic sequences, etc. An important aspect of the invention is to evaluate candidate drugs, including toxicity testing; and the like.

Candidate agents include organic molecules comprising functional groups necessary for structural interactions, particularly hydrogen bonding, and typically include at least an amine, carbonyl, hydroxyl or carboxyl group, frequently at least two of the functional chemical groups. The candidate agents often comprise cyclical carbon or heterocyclic structures and/or aromatic or polyaromatic structures substituted with one or more of the above functional groups. Candidate agents are also found among biomolecules, including peptides, polynucleotides, saccharides, fatty acids, steroids, purines, pyrimidines, derivatives, structural analogs or combinations thereof. Included are pharmacologically active drugs, genetically active molecules, etc. Compounds of interest include chemotherapeutic agents, hormones or hormone antagonists, etc. Exemplary of pharmaceutical agents suitable for this invention are those described in, "The Pharmacological Basis of Therapeutics," Goodman and Gilman, McGraw-Hill, New York, N.Y., (1996), Ninth edition. Also included are toxins, and biological and chemical warfare agents, for example see Somani, S. M. (Ed.), "Chemical Warfare Agents," Academic Press, New York, 1992).

Candidate agents of interest for screening also include nucleic acids, for example, nucleic acids that encode siRNA, shRNA, antisense molecules, or miRNA, or nucleic acids that encode polypeptides. Many vectors useful for transferring nucleic acids into target cells are available. The vectors may be maintained episomally, e.g. as plasmids, minicircle DNAs, virus-derived vectors such cytomegalovirus, adenovirus, etc., or they may be integrated into the target cell genome, through homologous recombination or random integration, e.g. retrovirus derived vectors such as MMLV, HIV-1, ALV, etc. Vectors may be provided directly to the subject cells. In other words, the cells are contacted with vectors comprising the nucleic acid of interest such that the vectors are taken up by the cells.

Methods for contacting cells with nucleic acid vectors, such as electroporation, calcium chloride transfection, and lipofection, are well known in the art. Alternatively, the nucleic acid of interest may be provided to the subject cells via a virus. In other words, the cells are contacted with viral particles comprising the nucleic acid of interest. Retroviruses, for example, lentiviruses, are particularly suitable to the method of the invention. Commonly used retroviral vectors are "defective", i.e. unable to produce viral proteins required for productive infection. Rather, replication of the vector requires growth in a packaging cell line. To generate viral particles comprising nucleic acids of interest, the nucleic acids comprising the nucleic acid are packaged into viral capsids by a packaging cell line. Different packaging cell lines provide a different envelope protein to be incorporated into the capsid, this envelope protein determining the specificity of the viral particle for the cells. Methods of introducing viral vectors comprising the nucleic acid of interest into packaging cell lines, of collecting the viral particles that are generated by the packaging lines, and of infecting cells using the packaged viral particles are well known in the art.

Vectors used for providing nucleic acid of interest to the subject cells will typically comprise suitable promoters for driving the expression, that is, transcriptional activation, of the nucleic acid of interest. This may include ubiquitously acting promoters, for example, the CMV-b-actin promoter, or inducible promoters, such as promoters that are active in particular cell populations or that respond to the presence of drugs such as tetracycline. By transcriptional activation, it is intended that transcription will be increased above basal levels in the target cell by at least about 10 fold, by at least about 100 fold, more usually by at least about 1000 fold. In addition, vectors used for providing reprogramming factors to the subject cells may include genes that must later be removed, e.g. using a recombinase system such as Cre/Lox, or the cells that express them destroyed, e.g. by including genes that allow selective toxicity such as herpesvirus TK, bcl-xs, etc.

Candidate agents of interest for screening also include polypeptides. Such polypeptides may optionally be fused to a polypeptide domain that increases solubility of the product. The domain may be linked to the polypeptide through a defined protease cleavage site, e.g. a TEV sequence, which is cleaved by TEV protease. The linker may also include one or more flexible sequences, e.g. from 1 to 10 glycine residues. In some embodiments, the cleavage of the fusion protein is performed in a buffer that maintains solubility of the product, e.g. in the presence of from 0.5 to 2 M urea, in the presence of polypeptides and/or polynucleotides that increase solubility, and the like. Domains of interest include endosomolytic domains, e.g. influenza HA domain; and other polypeptides that aid in production, e.g. IF2 domain, GST domain, GRPE domain, and the like.

If the candidate polypeptide agent is being assayed for its ability to act intracellularly, the polypeptide may comprise the polypeptide sequences of interest fused to a polypeptide permeant domain. A number of permeant domains are known in the art and may be used in the non-integrating polypeptides of the present invention, including peptides, peptidomimetics, and non-peptide carriers. For example, a permeant peptide may be derived from the third alpha helix of *Drosophila melanogaster* transcription factor Antennapaedia, referred to as penetratin. As another example, the permeant peptide comprises the HIV-1 tat basic region amino acid sequence, which may include, for example, amino acids 49-57 of naturally-occurring tat protein. Other permeant domains include poly-arginine motifs, for example, the region of amino acids 34-56 of HIV-1 rev protein, nona-arginine, octa-arginine, and the like. (See, for example, Futaki et al. (2003) Curr Protein Pept Sci. 2003 April; 4(2): 87-96; and Wender et al. (2000) Proc. Natl. Acad. Sci. U.S.A 2000 Nov. 21; 97(24):13003-8; published U.S. Patent applications 20030220334; 20030083256; 20030032593; and 20030022831, herein specifically incorporated by reference for the teachings of translocation peptides and peptoids). The nona-arginine (R9) sequence is one of the more efficient PTDs that have been characterized (Wender et al. 2000; Uemura et al. 2002).

The candidate polypeptide agent may be produced from eukaryotic produced by prokaryotic cells, it may be further processed by unfolding, e.g. heat denaturation, DTT reduction, etc. and may be further refolded, using methods known in the art. Modifications of interest that do not alter primary sequence include chemical derivatization of polypeptides, e.g., acylation, acetylation, carboxylation, amidation, etc. Also included are modifications of glycosylation, e.g. those made by modifying the glycosylation patterns of a polypeptide during its synthesis and processing or in further processing steps; e.g. by exposing the polypeptide to enzymes which affect glycosylation, such as mammalian glycosylating or deglycosylating enzymes. Also embraced are sequences that have phosphorylated amino acid residues, e.g. phosphotyrosine, phosphoserine, or phosphothreonine. The polypeptides may have been modified using ordinary molecular biological techniques and synthetic chemistry so as to improve their resistance to proteolytic degradation or to optimize solubility properties or to render them more suitable as a therapeutic agent. Analogs of such polypeptides include those containing residues other than naturally occurring L-amino acids, e.g. D-amino acids or non-naturally occurring synthetic amino acids. D-amino acids may be substituted for some or all of the amino acid residues.

Alternatively, the candidate polypeptide agent may be prepared by in vitro synthesis, using conventional methods as known in the art. Various commercial synthetic apparatuses are available, for example, automated synthesizers by Applied Biosystems, Inc., Beckman, etc. By using synthesizers, naturally occurring amino acids may be substituted with unnatural amino acids. The particular sequence and the manner of preparation will be determined by convenience, economics, purity required, and the like. Alternatively, the candidate polypeptide agent may be isolated and purified in accordance with conventional methods of recombinant synthesis. A lysate may be prepared of the expression host and the lysate purified using HPLC, exclusion chromatography, gel electrophoresis, affinity chromatography, or other purification technique. For the most part, the compositions which are used will comprise at least 20% by weight of the desired product, more usually at least about 75% by weight, preferably at least about 95% by weight, and for therapeutic purposes, usually at least about 99.5% by weight, in relation to contaminants related to the method of preparation of the product and its purification. Usually, the percentages will be based upon total protein.

In some cases, the candidate polypeptide agents to be screened are antibodies. The term "antibody" or "antibody moiety" is intended to include any polypeptide chain-containing molecular structure with a specific shape that fits to and recognizes an epitope, where one or more non-covalent binding interactions stabilize the complex between the molecular structure and the epitope. The specific or selective fit of a given structure and its specific epitope is sometimes referred to as a "lock and key" fit. The archetypal antibody molecule is the immunoglobulin, and all types of immunoglobulins, IgG, IgM, IgA, IgE, IgD, etc., from all sources, e.g. human, rodent, rabbit, cow, sheep, pig, dog, other mammal, chicken, other avians, etc., are considered to be "antibodies." Antibodies utilized in the present invention may be either polyclonal antibodies or monoclonal antibodies. Antibodies are typically provided in the media in which the cells are cultured.

Candidate agents may be obtained from a wide variety of sources including libraries of synthetic or natural compounds. For example, numerous means are available for random and directed synthesis of a wide variety of organic compounds, including biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Candidate agents are screened for biological activity by adding the agent to at least one and usually a plurality of cell samples, usually in conjunction with cells not contacted with the agent. The change in parameters in response to the agent is measured, and the result evaluated by comparison to reference cultures, e.g. in the presence and absence of the agent, obtained with other agents, etc.

The agents are conveniently added in solution, or readily soluble form, to the medium of cells in culture. The agents may be added in a flow-through system, as a stream, intermittent or continuous, or alternatively, adding a bolus of the compound, singly or incrementally, to an otherwise static solution. In a flow-through system, two fluids are used, where one is a physiologically neutral solution, and the other is the same solution with the test compound added. The first fluid is passed over the cells, followed by the second. In a single solution method, a bolus of the test compound is added to the volume of medium surrounding the cells. The overall concentrations of the components of the culture medium should not change significantly with the addition of the bolus, or between the two solutions in a flow through method.

A plurality of assays may be run in parallel with different agent concentrations to obtain a differential response to the various concentrations. As known in the art, determining the effective concentration of an agent typically uses a range of concentrations resulting from 1:10, or other log scale, dilutions. The concentrations may be further refined with a second series of dilutions, if necessary. Typically, one of these concentrations serves as a negative control, i.e. at zero concentration or below the level of detection of the agent or at or below the concentration of agent that does not give a detectable change in the phenotype. In some instances, as discussed above, a positive control may also be run.

Various methods can be utilized for quantifying the selected cellular parameter(s). For example, quantitative RT-PCR, western blots, ELISA assays, or protein arrays may be employed to measure the amount of BAF subunit, Ink4a, or Sox2 in the cell. Flow cytometry, microscopy, luminometry, histochemistry, immunohistochemistry, and the like may be employed to detect detectable labels tagging aBAF subunit, Ink4a, or Sox2 polypeptides or fragments thereof or reporters fused to Ink4a or Sox2 promoters. Drugs may be used to detect the expression of selectable markers. Such methods would be well known to one of ordinary skill in the art.

The following examples are offered by way of illustration and not by way of limitation.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

General methods in molecular and cellular biochemistry can be found in such standard textbooks as Molecular Cloning: A Laboratory Manual, 3rd Ed. (Sambrook et al., HaRBor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998), the disclosures of which are incorporated herein by reference. Reagents, cloning vectors, and kits for genetic manipulation referred to in this disclosure are available from commercial vendors such as BioRad, Stratagene, Invitrogen, Sigma-Aldrich, and ClonTech.

Example 1

Recent exon sequencing studies have revealed that over 19% of human tumors have mutations in subunits of mSWI/SNF (BAF) complexes. To investigate the underlying mechanism, we studied human synovial sarcoma (SS), in which transformation results from the translocation of exactly 78 amino acids of SSX to the SS18 subunit of BAF complexes. We demonstrate that the SS18-SSX fusion protein competes for assembly with wild-type SS18, forming an altered complex lacking the tumor suppressor BAF47 (hSNF5). The altered complex binds the Sox2 locus and reverses polycomb-mediated repression, resulting in Sox2 activation. Sox2 is uniformly expressed in SS tumors and is essential for proliferation. Increasing the concentration of wild-type SS18 leads to reassembly of wild-type complexes retargeted away from the Sox2 locus, polycomb-mediated repression of Sox2 and cessation of proliferation. This mechanism of transformation depends on only two amino acids of SSX, providing a potential foundation for therapeutic intervention.

Materials and Methods

Nuclear Extract Preparation and Proteomic Studies.

Nuclear extract (NE) preparation and immunoprecipitation (IP) studies were performed as described in Ho, L., et al. (2009). An embryonic stem cell chromatin remodeling complex, esBAF, is essential for embryonic stem cell self-renewal and pluripotency. *Proc Natl Aced Sci USA* 106, 5181-5186 and further below. Antibody specifications are presented in Table 1 below. All cell types were grown under standard conditions and lysed and homogenized in Buffer A (10 mM Hepes (pH 7.6), 25 mM KCl, 1 mM EDTA, 10% glycerol, 1 mM DTT, and protease inhibitors (complete mini tablets (Roche) supplemented with 1 mM PMSF) on ice. Nuclei were sedimented by centrifugation (1,000×g), resuspended in Buffer C (10 mM Hepes (pH 7.6), 3 mM MgCl2, 100 mM KCl, 0.1 mM EDTA, 10% glycerol, 1 mM DTT, and protease inhibitors), and lysed by the addition of ammonium sulfate to a final concentration of 0.3 M. Soluble nuclear proteins were separated by the insoluble chromatin fraction by ultracentrifugation (100,000×g) and precipitated with 0.3 mg/ml ammonium sulfate for 20 min on ice. Protein precipitate was isolated by ultracentrifugation (100,000×g), and resuspended in IP buffer (150 mM NaCl, 50 mM Tris-HCl (pH 8.0), 1% NonidetP-40, 0.5% deoxycholate, 1 mM DTT, 1 mM PMSF with protease inhibitors) for immunoprecipitation analyses or HEMG-0 buffer (25 mM HEPES pH 7.9, 0.1 mM EDTA, 12.5 mM MgCl2, 100 mM KCl, freshly supplemented with DTT and PMSF) for glycerol gradient analyses.

TABLE 1

| Antibody Specifications | | | | | |
|---|---|---|---|---|---|
| Antibody | Clone | Type | Peptide Region | Source | Catalog # |
| Brg | G7 | mouse monoclonal IgG1 | aa209-296; N-terminus | Santa Cruz Biotechnology | sc-17796 |
| BAF250 | C7 | mouse monoclonal IgG1 | | Santa Cruz Biotechnology | sc-373784 |
| BAF170 | | Rabbit polyclonal | aa744-857; internal | generated in-house | N/A |
| BAF155 | | Rabbit polyclonal | aa924-1004; C-terminus | generated in-house | N/A |
| BAF47 | A-5 | mouse monoclonal IgG1 | aa1-300 | Santa Cruz Biotechnology | sc-166165 |
| BAF45d | | Rabbit polyclonal | aa95-201; internal | generated in-house | N/A |
| SS18 | H80 | Rabbit polyclonal | 1-80 (h) | Santa Cruz Biotechnology | sc-28698 |
| SSX1 | C-7 | mouse monoclonal IgG1 | 1-188 | Santa Cruz Biotechnology | sc-166595 |
| Ezh2 | | Rabbit polyclonal | | Upstate/Millipore | 07-689 |
| Bmi1 | F6 | mouse monoclonal IgG1 | 1-202 | Upstate/Millipore | 05-637 |
| Sox2 | | rabbit polyclonal | | EMD Millipore | AB5603 |
| H3K27me3 | | Rabbit polyclonal | | Millipore | 07-449 |
| GAPDH | FL335 | Rabbit polyclonal | FL (h) | Santa Cruz Biotechnology | sc-25778 |
| GFP | | Rabbit polyclonal | | Invitrogen | A11122 |

Transfection Studies.

Briefly, cells were plated in 6-well plates to 80% confluence prior to transfection using PEI (Poly(ethylenimine)) in a 3:1 PEI:DNA ratio and were harvested at the appropriate time points thereafter.

Cell Proliferation Analyses.

Cells were assessed for >95% viability prior to being plated at 10^5 cells/well in triplicate/condition in 12-well plates. Cell counts were determined using trypan blue exclusion-based methods.

Urea Denaturation Studies.

NE (150 µg) were subjected to partial urea denaturation ranging from 0.25M to 8M urea (in IP buffer) for 15 min at RT prior to anti-Brg IP. The co-precipitated proteins were analyzed by immunoblot. Quantitative densitometry analyses were performed with the LiCor Oddessy Imaging System (Li-COR Biosciences).

Density Sedimentation Analyses.

800 µg NE were resuspended in 300 µl of 0% glycerol HEMG buffer, and carefully overlaid on to a 10 ml 10-30% glycerol (in HEMG buffer) gradient prepared in a 14×89 mm polyallomer centrifuge tube (Beckman #331327). Tubes were centrifuged in an SW40 rotor at 4° C. for 16 hrs at 40K RPM. 0.5 ml fractions were collected and used in analyses.

HEMG buffer: 25 mM HEPES pH 7.9, 0.1 mM EDTA, 12.5 mM $MgCl_2$, 100 mM KCl, freshly supplemented with DTT and PMSF before use.

Cyclohexamide/MG-132 Studies.

MG-132 (Calbiochem, #474790) (10 mg/ml in DMSO) was used at 1:1000, cyclohexamide (Sigma, #C4859) (100 mg/ml) at 1:100 in cell culture media. Briefly, cells were plated in 6-well plates and treated with the above agents for 0 to 24 hours and harvested with RIPA lysis buffer.

Gene Expression Profiling and Analysis.

Total RNA was isolated using TRIzol® reagent (Invitrogen) and reverse transcribed into cDNA (SuperScript® III RT kit (Invitrogen)). Real-time PCR was performed using TaqMan Universal Master Mix with Taqman probes and/or SYBR green method with custom designed primers, normalized to GAPDH and/or 18S rRNA expression. All primers are listed in Table 2 below.

TABLE 2

Primer Specifications

RT-PCR Primers

| Gene | TaqMan Assay ID # |
|---|---|
| Brg1 (smarca4) | Hs00231324_m1 |
| BAF155 (smarcc1) | hs00268265_m1 |
| BAF170 (smarcc2) | hs00161961_m1 |

TABLE 2-continued

Primer Specifications

| | |
|---|---|
| BAF47 (smarcb1) | hs00268260_m1 |
| SS18 | hs01075909_m1 |
| SOX2 | hs01053049_s1; hs04234836_s1 |
| Pou5f1 | hs00742896_s1 |
| Nanog | hs02387400_g1 |
| GAPDH | hs03929097_g1 |
| SS18-SSX ft | hs03024820_ft |

ChIP Primers

| Gene | Sequence (5'----3') |
|---|---|
| hSOX2-ChIP-Prom F (SEQ ID NO: 8) | GAGAAGGGCGTGAGAGAGTG |
| hSOX2-ChIP-Prom R (SEQ ID NO: 9) | AAACAGCCAGTGCAGGAGTT |
| hSOX2 TF1a For_ChIP (SEQ ID NO: 10) | AAACAGAGCTTTCCCCCAAT |
| hSOX2 TF1a Rev_ChIP (SEQ ID NO: 11) | TTGAGTGTGTTCCCCTCCTC |
| hSOX2 TF2a For_ChIP (SEQ ID NO: 12) | TCTCCAGGTCCGTGTTTACC |
| hSOX2 TF2a Rev_ChIP (SEQ ID NO: 13) | CCCGAAGGTTCTCCTTTTTC | shRNA-Mediated Knock Down and Lentiviral (LV) Generation.

shRNAs specific for human Brg1, BAF47, SS18, and Sox2 were purchased from Open Biosystems (Table 3). shRNA KD constructs for SS18-SSX and shScramble control were generated by annealed oligos (Table 4) and subsequent cloning into the pLK0.1 vector. LV was produced as described by Tiscornia et al. (Nat. Protoc. 2006; 1(1):234-40; Nat. Protoc. 2006; 1(1):241-5)

LV was produced by PEI (Polysciences Inc., 24765) transfection of 293t lentiX cells (Clontech) with gene delivery vector co-transfected with packaging vectors pspax2 and pMD2.G essentially as described by Tiscornia et al., supra. Cell supernatants were collected at 72 hours post transfection and centrifuged at 20,000 rpm for 2 hours at 4° C. Virus-containing pellets were resuspended in PBS and used to infect cells by spinfection methods (1000×g, 30 min at 37° C.). Selection of LV-infected cells was achieved with puromycin used at 2 µg/ml. KD efficiency was determined and confirmed by RT-PCR and western blot analysis. The SS18-SSX1 specific shRNA was designed, synthesized, and cloned into pLKO.1. Infected cells were selected with Puromycin (2 µg/ml).

TABLE 3 shRNA Specifications

| Gene | Species | Source | Clone ID# | Vector | Accession #'s |
|---|---|---|---|---|---|
| Brg1 | homo sapiens | Open Biosystems | V3LHS_317182 | pGIPZ | NM_001128844, NM_001128845, NM_001128846, NM_001128847 |
| SS18 | homo sapiens | Open Biosystems | V3LHS_412280, V3LHS_385463, V3LHS_385460 | pGIPZ | NM_001007559, NM_005637, AK296949, AK299082, AK304305, X79201 |
| BAF47 | homo sapiens | Open Biosystems | V2LHS_153159, V3LHS_367694, V3LHS_367696 | pGIPZ | NM_001007468, NM_003073 |
| Sox2 | homo sapiens | Open Biosystems | V2LHS_153337, V3LHS_404430, V3LHS404432 | pGIPZ | NM_003106, NM_011443, NM_001109181 |

TABLE 4

Annealed oligonucleotides

| Gene | Species | Source | Clone ID # | Vector | sequence |
|---|---|---|---|---|---|
| SS18-SSX shRNA-B_For (SEQ ID NO: 14) | homo sapiens | synthesized; oligo anneal | N/A | pLKO.1 | GGA CGA AAC ACC GGT CCG GCC AAG AGT TCG ATG TTA GTC TCG AGA CTA ACA TCG AAC TCT TGG TTT TTG GAA TTC TCG ACC TCG |
| SS18-SSX shRNA-B_Rev (SEQ ID NO: 15) | homo sapiens | synthesized; oligo anneal | N/A | pLKO.1 | CGA GGT CGA GAA TTC CAA AAA CCA AGA GTT CGA TGT TAG TCT CGA GAC TAA CAT CGA ACT CTT GGC CGG ACC GGT GTT TCG TCC |
| Control shRNA_For (SEQ ID NO: 16) | homo sapiens | synthesized; oligo anneal | N/A | pLKO.1 | GGA CGA AAC ACC GGT CCG GCT TAC GCT GAG TAC TTC GAC TCG AGT CGA AGT ACT CAG CGT AAG TTT TTG GAA TTC TCG ACC TCG |
| Control shRNA_Rev (SEQ ID NO: 17) | homo sapiens | synthesized; oligo anneal | N/A | pLKO.1 | CGA GGT CGA GAA TTC CAA AAA CTT ACG CTG AGT ACT CGA CTC GAC GTC GAA GTA CTC AGC GTA AGC CGG ACC GGT GTT TCG TCC |

ChIP Analyses.

Cells were crosslinked in formaldehyde, washed, and sonicated as described. ChIP antibodies: anti-BAF155 (in house generated), anti-H3K27me3 (Millipore, 07-449), V5 (Invitrogen, 46-0705). Primers used for real-time PCR are listed in Table 2 above.

For each 10 cm plate sample: cells were trypsinized for 5-8 min, trypsin was quenched by addition of 10 ml media containing FBS, cells were diluted to 40 ml with PBS and fixed for 12 min by addition of formaldehyde to a final concentration of 1%. Crosslinking was then quenched by addition of 2.5 M glycine (0.125 M final concentration) and cells were incubated on ice. Crosslinked cells were spun at 600×g for 5 min, nuclei were prepared by consecutive washes with Paro Rinse 1 buffer (10 mM Tris pH 8.0, 10 mM EDTA [pH 8.0], 0.5 mM EGTA, 0.25% Triton X-100) followed by Paro 2 buffer (10 mM Tris pH 8.0, 1 mM EDTA, 0.5 mM EGTA, 200 mM NaCl). Pellets were resuspended in 2 ml total volume of ChIP lysis buffer (50 mM HEPES/KOH pH 7.5, 300 mM NaCl, 1 mM EDTA, 1% Triton X-100, 0.1% DOC, 0.1% SDS, plus protease inhibitors complete mini (Roche)) and then sonicated for 9×30 s (ES cells) or 23×30 s at an amplitude of 30 with a Misonix sonicator, or until DNA was sheared to between 500 and 1000 bp (as confirmed by agarose gel). Antibodies used for ChIP are as follows: anti-BAF155 (in house generated), anti-H3K27me3 (Millipore, 07-449), V5 (Invitrogen, 46-0705). Primers used for real-time PCR listed in Table 2 above.

Affinity Purification and Mass Spectrometry.

A rabbit polyclonal antibody raised against aa1257-1338 of hBrg (SMARCA4) that recognizes both mouse Brg and Brm (SMARCA2) was used for affinity purification from nuclear extracts obtained from ES cells; a monoclonal antibody to Brg (SCBT G7) was used in purifications from p1.5 whole brains. Immunoprecipitation of endogenous complexes was performed in 300 mM NaCl, 50 mM Tris-HCl (pH 8.0), 1% Nonidet P-40, 0.5% deoxycholate, 0.1% SDS, 1 mM DTT. Purified complexes were separated further by strong cationic exchange, and fractions were analyzed on LTQ-Orbitrap (Thermo Scientific). Peptides were identified by searching acquired mass spectra using SEQUEST (University of Washington) against the Mouse IPI database version 3.34. Peptide identifications were validated statistically using PeptideProphet, and the protein inference was performed using ProteinProphet, available as a part of the TransProteomic Pipeline. The list of protein identifications in each analysis was filtered using a 0.95 probability threshold or as otherwise stated (estimated error rate of less than 1%). All proteins identified in the control runs and other known contaminants were subtracted from the final list.

Immunoprecipitation.

Nuclear extracts were resuspended in IP buffer and precleared for 30 minutes at 4 degrees C. using Protein G/A Sepharose beads (GE Healthcare). The protein concentration was determined using Bradford assay and adjusted to a final volume of 250 μL at a final concentration of 1.5 mg/mL with IP buffer. Each IP was incubated with 2.5 μg of antibody (Antibody specifications are presented in Table 1 above) overnight at 4° C. and then for 2 h with 20 μL Protein A/G Sepharose beads. The beads were washed four times at room temperature with 1 mL IP buffer and resuspended in 20 μL 2× gel loading buffer (4×LDS Buffer; Invitrogen)+DTT.

Results

SS18 is a Subunit of Mammalian SWI/SNF-Like BAF Complexes.

Figure 8:
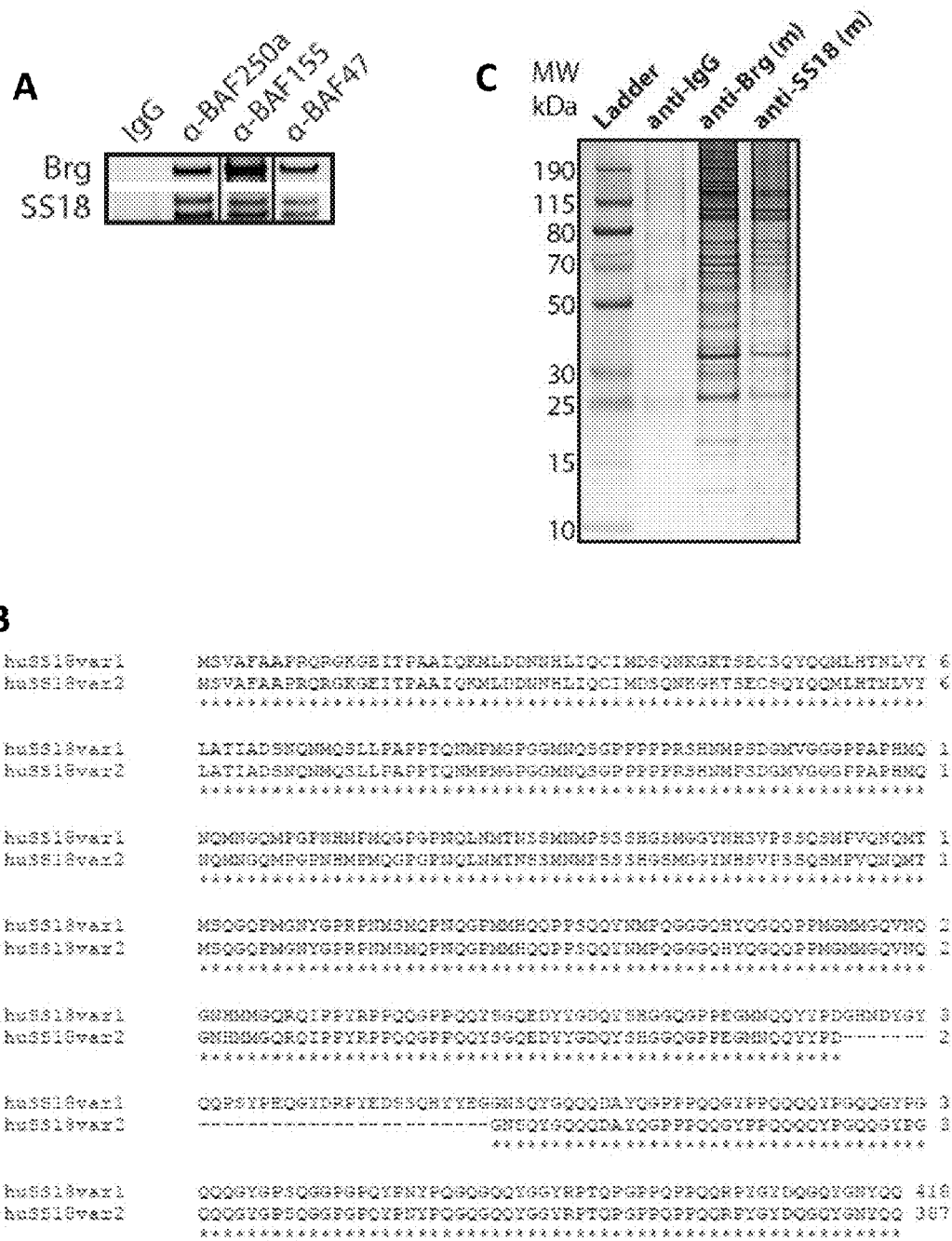
FIG. 8. (A) Immunoprecipitation using anti-BAF250a, anti-BAF155, or anti-BAF47 antibodies reveals SS18. (B) Human SS18 exists as two alternatively spliced isoforms (var1 SEQ ID NO:6 and var2 SEQ ID NO:7), yielding a double banding pattern upon immunoblot analysis. (C) Silver stain analysis of anti-Brg and anti-SS18 immunoprecipitations reveals similar banding patterns.

To better understand the composition of BAF complexes, we used a rapid biochemical/affinity purification approach to isolate endogenous complexes from non-transformed cells. Ammonium sulfate fractionation was followed by rapid affinity purification using a highly specific antibody to a genetically non-essential epitope in the Brg/Brm ATPase subunits (Ho, L., et al. (2009). An embryonic stem cell chromatin remodeling complex, esBAF, is essential for embryonic stem cell self-renewal and pluripotency. *Proc Natl Acad Sci USA* 106, 5181-5186). SS18 (synovial sarcoma translocation, chromosome 18) peptides were found in highly pure, endogenous BAF complexes in all tissue types examined, with the exception of post-mitotic adult neurons. Numbers of peptides and percent coverage for the protein SS18 were comparable to those of established BAF complex subunits, suggesting it is a subunit of BAF complexes (FIG. 1A). Immunoprecipitation studies using anti-Brg as well as antibodies specific to other established mSWI/SNF complex components including BAF250a, BAF155 and BAF47 confirmed the association of SS18 with native BAF complexes; similarly, reciprocal immunoprecipitation using an antibody to SS18 revealed known components of BAF complexes (FIG. 1B, FIG. 8A). Two bands are detected for human SS18 due to alternative splicing (FIG. 8B). Purification of complexes using anti-Brg and anti-SS18 antibodies revealed similar banding patterns upon silver stain analyses (FIG. 8C). In order to determine whether SS18 was dedicated exclusively to BAF complexes, we performed glycerol gradient sedimentation analyses, which demonstrated the presence of SS18 only in fractions containing Brg and other BAF complex subunits (fractions 12-15). SS18 did not associate with polycomb repressor complexes PRC1 or PRC2, as indicated by Bmi1 or Ezh2 immunoblots, respectively, or as a free monomer in earlier fractions of the gradient (FIG. 1C). Results were comparable in several cell types assayed including cell lines ES E14, Raji, 293T, and CCRF-CEM as well as primary human fibroblasts. Using urea-based denaturation studies, we determined that SS18 was remarkably stably bound to the complex, to a greater extent than most other subunits including BAF47, BAF155 and BAF 170, requiring denaturing conditions of greater than 5M urea to dissociate (FIG. 1D, FIG. 1E), similar to ribosomal subunits. The observation that SS18 remains bound when other subunits have dissociated indicates that SS18 binds directly to a stable core complex of Brg, BAF53a, and beta-actin (Zhao, K., et al. (1998). Rapid and phosphoinositol-dependent binding of the SWI/SNF-like BAF complex to chromatin after T lymphocyte receptor signaling. Cell 95, 625-636). These results demonstrate that SS18 is a dedicated subunit of mSWI/SNF or BAF complexes with binding characteristics similar to those of ribosomal subunits.

SS18-SSX Integrates into SWI-SNF-Like BAF Complexes and Alters Complex Composition.

The invariant molecular feature of human synovial sarcoma is the SS18-SSX fusion protein in which the C-terminal 78 amino acids of SSX are fused in frame with amino acids 1-379 of the SS18 subunit (FIG. 2A). To investigate the oncogenic mechanism, two biphasic synovial sarcoma (SS) lines, Aska-SS and Yamato-SS, were used, both of which bear the SS18-SSX1 chromosomal translocation (Naka, N., et al. (2010). Synovial sarcoma is a stem cell malignancy. Stem cells (Dayton, Ohio) 28, 1119-1131). Anti-Brg immunoprecipitation studies performed on nuclear extracts isolated from synovial sarcoma cell lines, as compared to control 293T cells (and various other cell types), demonstrated that when SS18 was fused to its translocation partner SSX, the SS18-SSX1 fusion protein was indeed bound to BAF complexes, as reflected by an appropriate upshift in molecular weight of SS18 from 55 kDa to 66 kDa upon immunoblot analysis (FIG. 2B, left). Remarkably, we observed that both synovial sarcoma lines, as compared to several other cell types assayed, exhibited lower to absent total protein levels of the tumor suppressor subunit BAF47 (hSNF5 or INI1) (FIG. 2B, right; FIG. 9A, left), while transcripts were largely comparable (FIG. 9A, right). Immunoprecipitated BAF complexes containing the SS18-SSX1 fusion protein showed nearly absent levels of wild-type SS18 on the complex. Input protein levels of the wild-type sized SS18 protein were also lowered, as were mRNA levels, suggesting reduced transcription (FIG. 9B), and consistent with previously reported findings (Brodin, B., et al. (2001) Cloning and characterization of spliced fusion transcript variants of synovial sarcoma: SYT/SSX4, SYT/SSX4v, and SYT/SSX2v. Possible regulatory role of the fusion gene product in wild type SYT expression. Gene 268, 173-182). In addition, a prominent Brg peak is located at the promoter and in an intronic region of the SS18 gene as determined by ChIP-seq analysis in murine ES cells (FIG. 9C) (Ho, L., et al. (2011) esBAF facilitates pluripotency by conditioning the genome for LIF/STAT3 signaling and by regulating polycomb function. Nat Cell Biol 3, 903-913), suggesting auto-regulation of this locus. Density sedimentation analyses performed on nuclear extracts isolated from Aska-SS and Yamato-SS lines revealed disruption of BAF complex composition, in that wild-type SS18 protein no longer associated with the BAF complex fractions (fractions 15, 16), and rather existed in fractions 3 and 4 suggesting its presence as a monomer (FIG. 2C, FIG. 9D). Quantitative densitometry of an anti-SS18 immunoblot of the glycerol gradient, revealed that only a small percentage (2-8%) of BAF complexes contains the wild-type SS18 protein in these cells (FIG. 9E). Side-by-side molecular weight comparisons indicated that the SS18-SSX fusion protein, in both SS lines, was almost entirely associated with the BAF complex (denoted by Brg peaks in fractions 15, 16) and the wild-type SS18 protein was present, albeit at lower protein levels, in the monomeric fractions of the gradient (fractions 3, 4) (FIG. 2D). This was further confirmed by immunoblotting using an anti-SSX1 antibody, which demonstrated the presence of SSX1 only in fractions containing Brg. As shown above, in SS cell lines containing the SS18-SSX fusion, BAF47 no longer associated with BAF complexes and was nearly absent from nuclear extracts indicative of degradation. This is particularly interesting given that BAF47 is a known tumor suppressor; loss of this subunit from the complex as a result of the integration of SS18-SSX might produce functional consequences similar to those of SNF5 inactivation. In order to further assess the degree of dedication of SS18 and SS18-SSX to the BAF complex, we performed depletion studies using two rounds of immunoprecipitation with polyclonal antibodies specific to a known complex subunit, BAF155, as well as to SS18's fusion partner, SSX1 (FIG. 2E). In 293T cells, BAF155 antibodies depleted SS18 protein from the nuclear extracts; SSX1 antibody did not deplete the lysate, as expected, in the wild-type setting. In the Aska-SS synovial sarcoma cell line, immunodepletion using the SSX1 antibody significantly depleted complex subunits Brg, BAF155, and SS18-SSX proteins from nuclear extracts to comparable levels as with anti-BAF155 antibody. These results collectively demonstrate that both wild-type SS18 and in synovial sarcoma, the SS18-SSX1 fusion protein, are dedicated to BAF complexes, but that the fusion protein alters subunit composition.

To understand how incorporation of SS18-SSX alters the biochemical subunit composition of BAF complexes, we produced N-terminally GFP-tagged constructs of SS18 FL (full length, aa 1-387), SS18 aa 1-379 (lacking the last C-terminal 8 aa which are lost in the fusion), and SS18-SSX using a pEGFP-based expression system (FIG. 3A). Previous studies have established that the N-terminal SNH domain of SS18 is responsible for its BAF complex association (Nagai, M., et al. (2001) Analysis of transforming activity of human synovial sarcoma-associated chimeric protein SYT-SSX1 bound to chromatin remodeling factor hBRM/hSNF2 alpha. Proc Nat Acad Sci USA 98, 3843-3848). Anti-GFP immunoprecipitations were performed to isolate BAF complexes which had incorporated the exogenously introduced SS18 or SS18-SSX variants. Expressing the SS18-SSX fusion protein resulted in the loss of BAF47 from the complex at 72 hours post-transfection (FIG. 3B). Wild-type SS18 FL or SS18 1-379 both incorporated into BAF complexes but did not alter BAF47 binding to the complex. Input levels of BAF47 at this time point (72 hours) following introduction of SS18-SSX (and all variants tested) were comparable to those of untreated cells. Immunoblot analysis performed on total input protein harvested at 96 hours post-transfection with SS18-SSX indicated a marked decrease in BAF47 levels, with mRNA levels held stable, suggesting that BAF47 is first lost from the complex upon integration of SS18-SSX and subsequently degraded (FIG. 3C, FIG. 10). To understand the means by which BAF47 is degraded under normal conditions, we performed cyclohexamide (CH) chase experiments over 24 hours, plus and minus proteasome inhibitor treatment using MG-132 at the 24 hour time point. The protein half-life of BAF47 was approximately 10 hours after the addition of CH; BAF47 levels could be rescued from CH treatment with MG-132 to >85% of control levels, indicative of proteasome-mediated degradation (FIG. 3D). Treatment of Aska-SS cells with MG-132 resulted in a substantial increase in BAF47 total protein levels (FIG. 3E). Upon infection of SS18-SSX1 into 293T fibroblasts, wild-type SS18-containing complexes were readily replaced by SS18-SSX containing complexes (fractions 14,15,16) and BAF47 levels were reduced as determined by glycerol gradient analyses (FIG. 3F). Wild-type SS18 was observed in free, monomeric fractions of the glycerol gradient, as well as in transient lower molecular weight, Brg-associated fractions 9-11. These studies indicate that the SS18-SSX fusion incorporates into BAF complexes, replacing wild-type SS18, and ejecting and destabilizing BAF47.

To understand whether low protein levels of BAF47 results specifically from the presence of the SS18-SSX1 fusion in SS cells, we generated shRNA-based knock down (KD) constructs specific for the 3' UTR of SSX (based on Takenaka, S., et al. (2010) Downregulation of SS18-SSX1 expression in synovial sarcoma by small interfering RNA enhances the focal adhesion pathway and inhibits anchorage-independent growth in vitro and tumor growth in vivo. *International journal of oncology* 36, 823-831) to exclusively target SS18-SSX, but not wild-type SS18. Remarkably, we noted a substantial increase in BAF47 total protein levels upon KD of the SS18-SSX oncogenic fusion (FIG. 3G). In addition, wild-type SS18 protein levels increased, suggesting relieved repression of SS18 upon KD of the SS18-SSX fusion. We assessed the effect of SS18-SSX KD on proliferation of both synovial sarcoma cell lines. Importantly, KD of the SS18-SSX fusion and of Brg, to which the SS18-SSX fusion was bound, resulted in a profound decrease in proliferation of synovial sarcoma cells (FIG. 3H). By contrast, KD of wild-type SS18 and BAF47, subunits not contained in the SS18-SSX-containing BAF complexes, wild-type SS18 and BAF47, had little to no effect on synovial sarcoma cell proliferation (FIG. 3H), suggesting that the aberrant residual complex is responsible for driving and maintaining cell proliferation. In human primary fibroblasts with wildtype complexes, KD of Brg, SS18 and BAF47 reduced proliferation; KD of SS18-SSX1 did not alter proliferation as compared to control hairpin (FIG. 3I). These studies indicate that the eviction of BAF47 inactivates it and that it is no longer required for proliferation of the SS cell lines. Hence, the free BAF47 protein does not acquire a new function enabling transformation.

Synovial Sarcoma Cell Gene Expression Features Recapitulated: SS18-SSX Induces Sox2 Expression.

Several studies have demonstrated that SS cells harbor stem-cell like gene expression profiles (Garcia, C. B., et al. (2012) Reprogramming of mesenchymal stem cells by the synovial sarcoma-associated oncogene SYT-SSX2. *Oncogene* 31, 2323-2334; Naka, N., et al. (2010) Synovial sarcoma is a stem cell malignancy. *Stem cells* 28, 1119-1131). Moreover, Roberts and colleagues observed that tumors lacking the BAF47 tumor suppressor subunit also express stem cell-like signatures (Wilson, B. G., et al. (2010) Epigenetic antagonism between polycomb and SWI/SNF complexes during oncogenic transformation. *Cancer Cell* 18, 316-328). Naka and colleagues demonstrated that Aska-SS and Yamato-SS lines as well as 15/15 human tumor specimens of synovial sarcoma tested express mRNA transcripts of pluripotency factors Sox2, Oct4 and Nanog (Naka, N., et al. (2010) Synovial sarcoma is a stem cell malignancy. *Stem cells* 28, 1119-1131). We focused on Sox2 because of its role in oncogenesis (Bass, A. J., et al. (2009) SOX2 is an amplified lineage-survival oncogene in lung and esophageal squamous cell carcinomas. *Nature Genetics* 41, 1238-1242). Introduction of SS18-SSX dramatically induced Sox2 mRNA in primary, untransformed human neonatal foreskin fibroblasts by 15 days post-infection and selection (FIG. 4A). This induction was specific to the full SS18-SSX1 fusion and did not occur when the C-terminal 34 aa of the conserved SSXRD domain was removed from SSX1.

To determine if Sox2 mRNA induction was driven by the partially formed complexes, we tested the effect of shRNA-mediated KD of SS18 and BAF47 in fibroblasts on Sox2 mRNA induction. KD of SS18 and BAF47 both resulted in a statistically significant increase in Sox2 mRNA to levels nearly comparable to those resulting from overexpression of SS18-SSX (FIG. 4A). At the protein level, BAF47 and SS18 appear to reciprocally regulate one another's stability in fibroblasts as determined by KD of BAF47 and SS18 and immunoblot analysis for protein levels of each (FIG. 11A). KD of Brg alone resulted in >70% reduction in protein levels, but did not induce Sox2. Collectively, these data suggest that the activity of aberrant complexes, which lack BAF47 and wild-type SS18, are responsible for Sox2 mRNA induction. Sox2 mRNA levels increased 23-fold by day 25 post-infection with SS18-SSX1 as compared to control (FIG. 4B). Oct4 and Nanog mRNA were not induced significantly.

We sought to determine whether Sox2 was important for synovial sarcoma cell proliferation. To this end, we generated lentivirus containing two different shRNA hairpins to Sox2 which both effectively reduced Sox2 mRNA and protein in Aska SS cells (FIG. 4C) and assessed proliferative capacity in vitro. shRNA-mediated KD of Sox2 profoundly reduced proliferation of Aska-SS cells as compared to scrambled shRNA control (FIG. 4D). Sox2 mRNA and protein levels were reduced in Aska-SS cells upon KD of the SS18-SSX1 fusion to levels comparable to those of cells treated with Sox2 shRNA itself (FIG. 4E), indicating elevated levels of Sox2 were specifically due to the presence of SS18-SSX fusion.

Figure 4F:
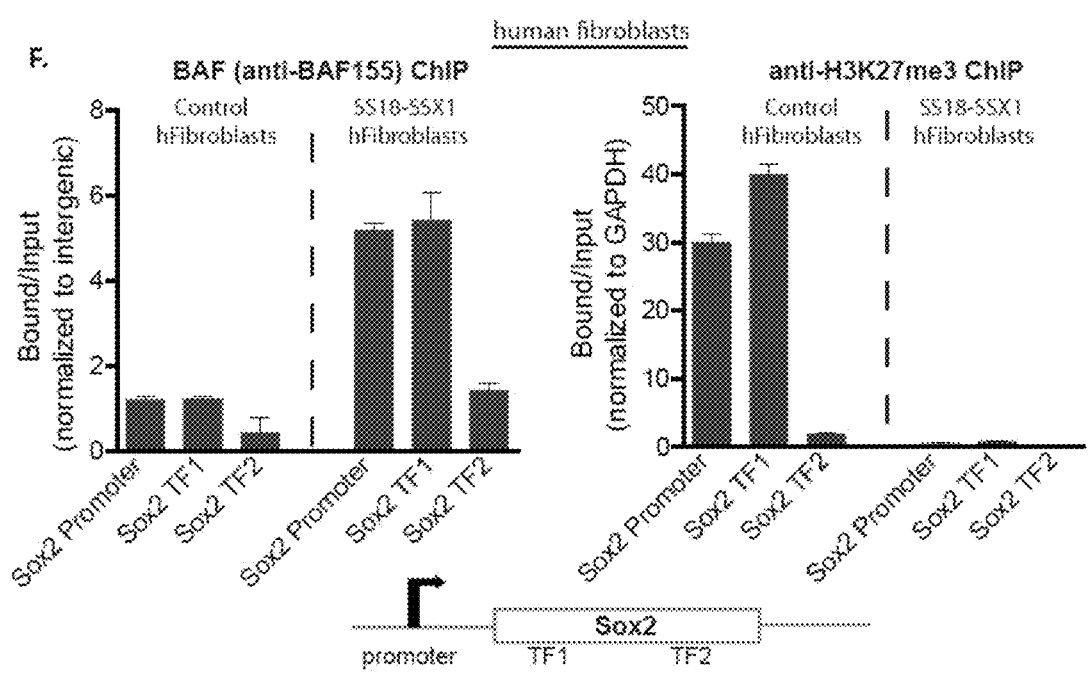
FIG. 4. SS18-SSX1 induces Sox2 mRNA expression which drives SS cell proliferation. (A) Sox2 mRNA levels at day 10 post-infection with LV containing either SS18/SS18-SSX variants or shRNAs to BAF complex subunits. (Normalized to GAPDH; *p<0.005, p<0.01). See also FIG. 11A. (B) Time course of Sox2, Oct4, and Nanog mRNA levels post-infection with SS18-SSX-containing LV. (Normalized to GAPDH; error bars reflect s.d. in n=5 separate experiments). (C) shRNA-mediated knock-down of Sox2 in Aska-SS cells: top, immunoblot analysis; bottom, Sox2 mRNA levels. (D) Proliferative analysis of Aska-SS cells treated with Sox2 shRNA KD LV. Control, shScramble. (E) Left, Immunoblot analysis on Aska-SS cells treated with shControl or with either shSS18-SSX1 or shSox2-1; Right, Sox2 mRNA relative expression (normalized to GAPDH). (F) Left, anti-BAF155 ChIP on human primary fibroblasts treated with either empty vector or SS18-SSX1, with subsequent qPCR for regions at the human Sox2 promoter and two Sox2 transcription factor (TF) binding sites within the exon. Right, anti-H3K27me3 ChIP. Error bars, s.d. of n=3 experiments. See also FIG. 11B, C.

To understand the mechanism of Sox2 induction by SS18-SSX, we assessed BAF complex occupancy at the Sox2 promoter as well as two clusters of transcription factor (TF) binding sites within the Sox2 exonic region using our affinity-purified BAF155 polyclonal antibody. Intergenic regions were selected as normalization controls. SS18-SSX1-infected primary human fibroblasts demonstrated a significant increase in BAF complex occupancy at all three sites within the human Sox2 locus as compared to control fibroblasts (FIG. 4F). In MEFs, there is a prominent H3K27me3 peak over the Sox2 locus as shown by MEF ChIP-seq studies (Mikkelsen, T. S., et al. (2007). Genome-wide maps of chromatin state in pluripotent and lineage-committed cells. *Nature* 448, 553-560), consistent with absent Sox2 expression in these cells (FIG. 11B). Lentiviral introduction of SS18-SSX1 into primary human fibroblasts resulted in a striking decrease in H3K27me3 enrichment at all three sites tested within the Sox2 locus (FIG. 4F).

To determine if the 78 aa tail of SSX was itself responsible for the targeting of BAF complexes to the Sox2 locus (perhaps by binding a transcription factor) we infected human fibroblasts with V5-tagged SSX78 aa (as well as SS18FL and SS18-SSX). However, we did not find that the 78 aa SSX fragment localized to the Sox2 locus (FIG. 11C). These studies indicate that the SS18-SSX fusion functioning within the altered BAF complexes binds to and activates the Sox2 locus in fibroblasts by disrupting H3K27me3-mediated repression, which is likely directed by the actions of PRC2, the only complex known to place this mark (Chamberlain, S. J., et al. (2008) Polycomb repressive complex 2 is dispensable for maintenance of embryonic stem cell pluripotency. Stem Cells 26, 1496-1505).

Molecular Requirements of SS18-SSX for BAF47 Ejection from BAF Complexes.

Because expression of SS18-SSX1 resulted in the ejection and subsequent degradation of the BAF47 subunit, we aimed to understand the features of the 78 amino acid SSX tail that could be responsible for this. We generated a series of truncation mutants: deleting the conserved SSXRD domain of 34 aa, deleting ½ of the SSXRD domain (17 aa, hydrophobic) and adding amino acids in increments of 10 amino acids to the SS18 C-terminus (+10 through +70). We noted that SS18+10 through SS18+70 did not result in significant ejection of BAF47 from the complex as determined by immunoblot analysis and quantitative densitometry performed on immunoprecipitated complexes (FIG. 5A). This implies that a region in the last 8 amino acids (SDPEEDDE) (SEQ ID NO:18) is required for BAF47 ejection. Deleting ½ of SSXRD resulted in slightly decreased levels of BAF47. Upon introduction of these variants into human fibroblasts, Sox2 mRNA induction was only observed with SS18-SSX1 (FIG. 5B).

Because none of these truncation mutants fully recapitulated the SS18-SSX1-induced BAF47 ejection and Sox2 mRNA induction phenotype, we turned to the fact that the only translocations that have been observed in human synovial sarcoma are SS18-SSX1, SS18-SSX2, and SS18-SSX4. SS18-SSX3 has never been observed in a human tumor. This family of 9 genes (SSX1-9) located at ch Xp11.2 is highly similar; protein homology among members ranges from 73-93% (Smith, R A., et al. (2010) The SSX family of cancer-testis antigens as target proteins for tumor therapy. Clin Dev Immunol 2010, 150591). We used Kyte-Doolittle hydrophobicity analysis to compare the 78 C-terminal amino acids of SSX1, 2, 4 versus SSX3, which revealed a significant difference in hydrophobicity between amino acids 40-50 (FIG. 5C), as highlighted. Upon peptide alignment of the 78 amino acids of SSX1-4 it became clear that the amino acid composition at positions 43 and 44 was most discrepant between the SSX members observed in human SS tumors (1,2 and 4) and the non-oncogenic SSX3. SSX1, SSX2, and SSX4 contain lysine (K) and arginine (R), glutamic acid (E) and arginine (R), and lysine (K) and threonine (T), respectively at position 43, 44, while SSX3 contains a methionine (M) and isoleucine (I) at these positions (FIG. 5D, arrows). Given that SSX1 is a common fusion partner of SS18 in synovial sarcoma and SSX3 is not, we then sought to understand if SSX3 fused to SS18 could result in BAF47 ejection and Sox2 induction. To this end, we generated an SS18-SSX3 fusion protein (379 amino acids of SS18 fused to 78 amino acids of the SSX3 C-terminus). SS18-SSX3 was able to integrate into BAF complexes, as assessed by anti-GFP immunoprecipitation of BAF complexes, but failed to eject BAF47 (FIG. 5E) from the complexes. Remarkably, replacement of amino acids 43, 44 of SSX1 (KR) with those of SSX3 (MI) in the SS18-SSX1 fusion resulted in substantial loss of the ability to displace BAF47 (FIG. 5F). Reciprocal amino acid substitution at position 43, 44 in SS18-SSX3 (MI to KR) resulted in the gained ability of SS18-SSX3 to eject BAF47. Comparative densitometry accounting for the BAF47/Brg ratio is shown, representative of n=3 experiments (FIG. 5G). Intriguingly, SS18-SSX1 as well as SS18-SSX3 (A43, 44 MI-*KR) significantly induced Sox2 mRNA; no other variant produced this phenotype (FIG. 5H), lending further evidence that the loss of BAF47 (hSnfS) from mSWI/SNF complexes is necessary for the induction of Sox2 mRNA expression in synovial sarcoma. All three fusions reported in human synovial sarcomas (SSX1, 2, 4) produced BAF47 eviction, while SS18-SSX3 and SS18-SSX5 (which bears an amino acid change in the last 8 aa of SSX) fusions did not (FIG. 12A, B).

Reversibility of BAF Complex Subunit Composition and Targeting in Human Synovial Sarcoma.

Our observation that SS18 was displaced or failed to assemble into BAF complexes in the presence of somewhat higher concentrations of the SS18-SSX fusion protein (FIGS. 2C, 3F) lead us to investigate the possibility that the transforming fusion protein and the wild-type protein might exist in a concentration-dependent equilibrium or could be competing for assembly into newly formed complexes. Urea-based denaturation experiments demonstrated that SS18 and SS18-SSX are both stably bound to BAF complexes and dissociate to comparable degrees from 0 to 8 M urea as shown by immunoblot and quantitative densitometry analyses (FIG. 6A, 6B). BAF complex components dissociated at comparable levels across the urea denaturation series from V5-tagged SS18 and SS18-SSX, indicative of equal affinity binding of wild-type SS18 and SS18-SSX (FIG. 6C). Moreover, Brg and β-actin remained bound to V5-SS18/SS18-SSX-purified complexes to >5M urea, suggesting that SS18/SS18-SSX is part of a highly stable core complex of Brg, BAF53a and β-actin.

Given these findings and having observed that shRNA-mediated KD of the SS18-SSX1 fusion could restore BAF47 total protein levels (FIG. 3G), we sought to determine whether overexpression of wild-type SS18 could also be sufficient to allow normal complexes to reform in synovial sarcoma cell lines and whether this could reverse the misassembly of synovial sarcoma BAF complexes and correct the gene expression phenotypes. Intriguingly, introduction of SS18 FL or SS18 1-379 resulted in a profound increase in BAF47 total protein levels by Day 10 post-infection (FIG. 6D, left). Moreover, BAF complexes in Aska-SS cells infected with SS18 regained normal incorporation of wild-type SS18 and BAF47 subunits, suggesting concentration-driven re-integration of SS18 (FIG. 6D, right). Introduction of SS18-SSX1 into 293T fibroblasts resulted in reduction of BAF47 total protein to a comparable degree as shRNA-mediated KD of BAF47 (FIG. 6E). These studies indicate that the SS18-SSX fusion protein and the wild type SS18 protein compete for assembly into BAF complexes and that the transforming mutant protein can be displaced from BAF complexes to yield wild-type complexes by increasing the concentration of the wild-type protein.

Figure 6H:
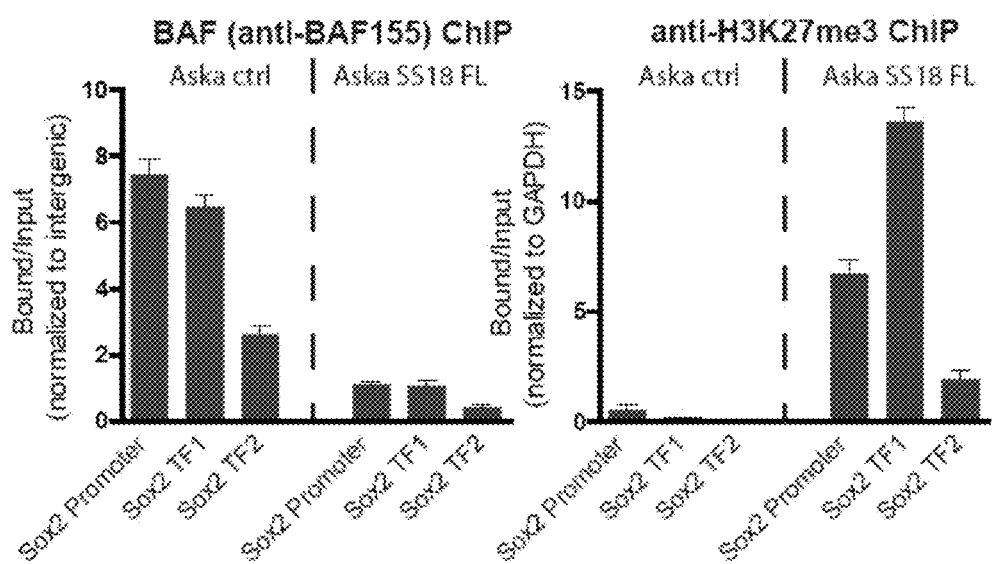
FIG. 6. Reversible integration, gene expression and occupancy by SS18 and SS18-SSX containing mSWI/SNF (BAF) complexes. (A) Denaturation studies using 0-8M urea with subsequent immunoblot analysis for SS18 in 293T cells and SS18-SSX in Aska-SS cells. See also FIG. 13. (B) Quantitative densitometry of SS18 or SS18-SSX1 protein immunoblots from n=3 experimental replicates of urea denaturation 0<[urea]<8M. Y-axis: band quantitation/untreated control. Error bars=s.d. (C) IP using anti-V5 antibody in urea treated nuclear extracts isolated from 293T fibroblasts infected with either V5-SS18 or V5-SS18-SSX with immunoblotting for BAF complex components. (D) Left, Immunoblot analysis on total protein isolated from Aska-SS cells with either SS18 or SS18 1-379 or SS18-SSX1 introduced via LV. Right, anti-Brg IP of complexes in either empty vector or V5-SS18FL treated conditions. (E) Introduction of SS18-SSX1 and shBAF47 into 293T cells with subsequent immunoblot analysis on total protein. (F) Cell proliferation analyses of Aska-SS cells infected with control vector, SS18, SS18 1-379, and SS18-SSX. Error bars=s.d. (G) Sox2 mRNA relative expression (normalized to GAPDH) 10 days post infection with LV containing either control shScramble or overexpression of SS18, SS18 1-379, or SS18-SSX. Error bars=s.d. (H) Left, anti-BAF155 ChIP on Aska-SS cells treated with either empty vector or SS18 FL, with subsequent qPCR for regions at the human Sox2 promoter and two Sox2 transcription factor (TF) binding sites within the exon. Right, anti-H3K27me3 ChIP at Sox2 locus in Aska-SS control treated and SS18 FL-treated cells. Error bars=s.d.

Proliferation of SS cells was inhibited by introduction of wild-type SS18 and SS18 1-379, to a similar degree as in cells treated with shRNA-mediated KD of the SS18-SSX1 fusion (FIG. 6F). In contrast, introduction of SS18-SSX into SS18-SSX-bearing synovial sarcoma Aska-SS cells had no appreciable effect on proliferation as compared to control. Sox2 mRNA expression levels in Aska-SS cells were reduced by 3- and 4-fold, upon overexpression of SS18FL and SS18 1-379, respectively (FIG. 6G). In contrast, overexpression of SS18-SSX1 in these lines already bearing one translocated allele caused Sox2 mRNA levels to increase 1.7-fold above control levels relative to empty vector control indicating that the levels of Sox2 produced by the SS18-SSX fusion protein were not at maximum. Finally, Aska-SS synovial sarcoma cells infected with SS18FL to reverse the BAF complex phenotype exhibited a dramatically decreased occupancy of BAF complexes at the human Sox2 locus with a concomitant increase in H3K27me3 occupancy (FIG. 6H). These studies indicate that normal BAF complexes can be reassembled in malignant cells by over expression of the wild type SS18 protein, leading to BAF complex removal from the Sox2 gene and resumption of normal repression of Sox2 by H3K27 trimethylation.

Finally, we aimed to test the potential for BAF47 overexpression to promote reassembly of wildtype BAF complexes containing BAF47 and SS18 in SS cells and its effect on proliferation. Notably, overexpressed V5-tagged BAF47 was unable to bind SS18-SSX containing complexes in both SS cell lines tested, as evidenced by low protein levels on complexes detected by anti-Brg and anti-V5 immunoprecipitations as well as by total protein immunoblots, suggestive of rapid degradation (FIG. 7A). To test whether shifting aberrant complex assembly back to that of wild-type would allow for integration of the exogenous BAF47-V5 into complexes we infected SS cells containing BAF47-V5 with either SS18FL or shSS18-SSX. Indeed, in both lines, overexpression of SS18FL or KD of the SS18-SSX fusion resulted in increased incorporation and stabilization of BAF47-V5 as indicated by anti-Brg immunoprecipitation (FIG. 7B). BAF47 overxpression had no effect on SS cell proliferation in culture; however, proliferation was dramatically attenuated upon co-introduction of overexpressed SS18FL or KD of SS18-SSX, suggesting that BAF47 can only assemble into wild-type SS18-containing complexes and not complexes bearing the SS18-SSX fusion (FIG. 7C).

Discussion

Figure 7D:
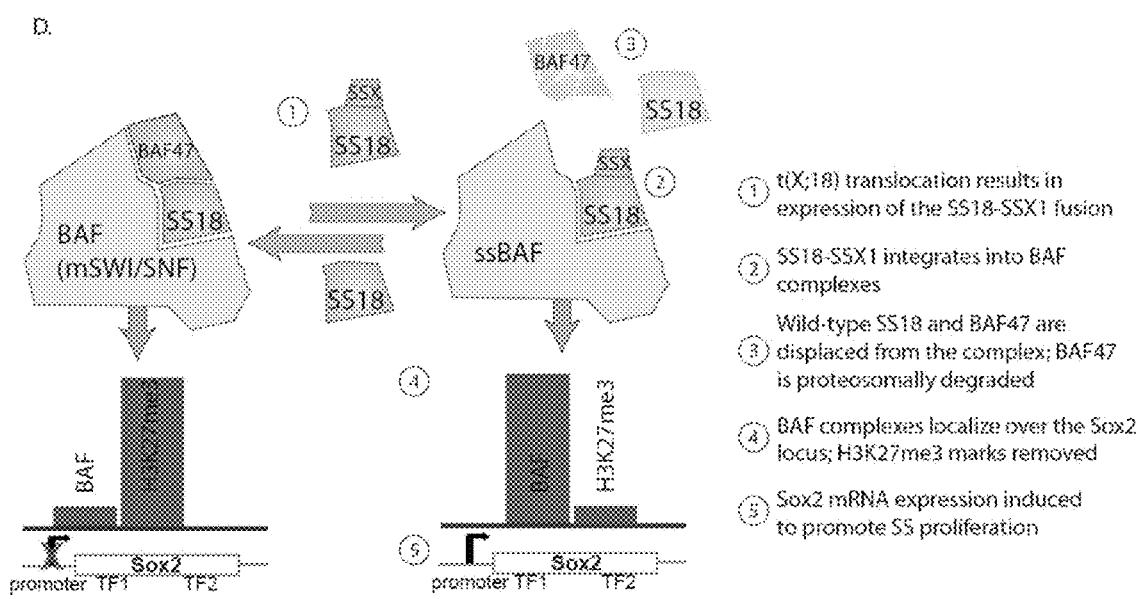
FIG. 7. A model for reversible transformation by the SS18-SSX1 oncogenic fusion. (A) (left) Anti-Brg IPs on 293T, B35, Aska-SS and Yamato-SS cells bearing introduced BAF47-V5; (middle) anti-V5 IPs; (right) Total protein inputs. (B) Anti-Brg IPs on nuclear extracts of Aska-SS and Yamato-SS cells with stably introduced BAF47-V5 and co-infection with either control vector, SS18FL, or shSS18-SSX. (C) Proliferation analyses of Aska-SS cells infected with either control vector, BAF47-V5, or BAF47-V5+co-infected SS18FL, BAF47-V5+co-infected shSS18-SSX. Error bars=s.d. (D) Model for reversible disruption of BAF complex composition and action upon SS18-SSX incorporation.

Our studies demonstrate that in sarcoma cells, the fusion of SS18 with SSX, which is diagnostic of this tumor type, leads to assembly of aberrant BAF complexes that become targeted to the Sox2 locus, with loss of repressive H3K27me3 marks, driving Sox2 expression and proliferation of these cells (FIG. 7D). The observation that Sox2 is activated in all SS studied (Naka, N., et al. (2010) Synovial sarcoma is a stem cell malignancy. *Stem cells* 28, 1119-1131) indicates this is a general mechanism of oncogenesis in these tumors. We find that the SS18-SSX fusion incorporates into BAF complexes and activates Sox2 expression, explaining the uniform activation of this gene in SS. But how do complexes containing the SS18-SSX fusion activate Sox2? BAF complexes containing the SS18-SSX fusion could be targeted by the interaction of SSX with a factor that binds the Sox2 locus. Alternatively, an incorrectly assembled complex could target the Sox 2 locus by changes to bromo-, chromo- and PHD domain presentation. We find that the 78 aa of SSX alone is not targeted to the Sox2 locus when expressed in human fibroblasts (FIG. 11B), indicating that it is the aberrantly assembled complex that targets the inactive Sox2 locus, reversing H3K27Me3-mediated repression, and leading to Sox2 activation.

The wild type SS18 protein is capable of replacing the SS18-SSX fusion in BAF complexes when expressed at somewhat higher levels than the fusion protein. The incorporation of wild-type and mutant proteins is unlikely to be due to direct binding competition. This conclusion arises from the fact that 8 M urea is required to remove either the wild-type SS18 protein from the wild type complexes or the SS18-SSX fusion from the malignant complexes. Hence, the two proteins most likely compete for assembly into complexes, with the product of the fusion allele winning in SS cells due to increased concentration.

The ability of SS18-SSX to disrupt BAF complexes maps to two regions of the SSX protein: The C-terminal 8 amino acids (SDPEEDDE) (SEQ ID NO:18) and a polar region of two amino acids present in the oncogenic members of the SSX family of proteins. Substitution of KR with MI, found in the non-transforming SSX3, restores normal complex assembly and gene regulation; substitution of MI with KR in SS18-SSX3 results in BAF47 ejection and increased Sox2 mRNA. In this regard, SSX5 is interesting in that it has KT at position 43, 44, combined with an amino acid substitution of P for E in the 8 terminal amino acids; SS18-SSX5 has not been found in translocations and does not eject BAF47, confirming the importance of both regions for oncogenicity. These two regions could interact to facilitate complex dissolution or form dimers in the malignant complexes. Structural studies will be necessary to define the precise mechanism. However, the ability of such a small region to lead to complex dissolution and the observation that the wild type and malignant protein are in a dynamic equilibrium indicates that the fusion containing the two amino acid essential region in the SSX tail (K43, R44) is an excellent target for developing therapeutics for this disease. A decoy molecule that causes SSX1 to resemble SSX3 would be expected to prevent eviction of BAF47, and thereby reverse the effects of the aberrant SS-BAF complex. This notion is consistent with the precision of the oncogenic translocation, in that all translocations discovered to date add exactly 78 amino acids of SSX1, 2 or 4 to the SS18 protein at position 379.

In SS cells, the partially assembled complex gains the ability to bind the Sox2 gene, reversing H3K27Me3-mediated repression. Forcing correct assembly by expressing the wild-type SS18 causes the reassembly of wild-type complexes without the fusion thus reestablishing normal repression of Sox2 by polycomb. The fly Brahma protein was discovered from its ability to oppose polycomb and hence is known as a trithorax gene, however the underlying biochemical mechanisms have been controversial. In some studies, polycomb was found to prevent Brahma (BAP) complex binding, while in others it seemed that BAP or SWI/SNF directly recruited Poll I, thereby opposing polycomb. Our studies suggest that somehow BAF complexes evict polycomb, however our temporal resolution is limited to the infection times (24-72 hrs) and hence we are unable to determine if the mechanism is direct physical eviction, or dilution of H3K27Me3 by nucleosome exchange with cell division since the measured rates of nucleosome turnover (Deal, R. B., et al. (2010) Genome-wide kinetics of nucleosome turnover determined by metabolic labeling of histones. *Science* 328, 1161-1164) are sufficient to remove most H3K27Me3 if methylation were prevented by the SS BAF complex. Evidence for BAF-polycomb opposition in malignancy has also been found with inactivation of BAF47 (hSNF5 or Ini1) in human malignant rhabdoid sarcoma (MRTs). In these tumors and in mouse models, polycomb was found to be removed from the INK4a locus upon introduction of BAF47 (hSNF5) (Kia et al., 2008) Understanding the underlying mechanism of polycomb opposition will require techniques that allow rapid recruitment of BAF complexes with a high degree of temporal and spatial control (Hathaway, N. A., et al. (2012). Dynamics and memory of heterochromatin in living cells. *Cell* 149, 1447-1460).

Synovial sarcoma is largely resistant to conventional, chemotherapy-based forms of treatment, underlining the need for an understanding of its pathogenesis. Disease-specific biologic agents which target SS18-SSX or its interactions have to date not been developed. Here we have shown that the SS18-SSX1 oncogenic fusion usurps SWI/SNF-like BAF complexes, resulting in activation of Sox2, which drives proliferation. Remarkably, the oncogenic fusion and wild-type SS18 bind to BAF complexes with comparable affinities, allowing directed assembly of oncogenic or wild-type complexes. Moreover, the composition of SS18-SSX-containing BAF complexes (lacking BAF47 and wild-type SS18) can be reversed by reducing the levels of SS18-SSX or by increasing levels of wild-type SS18. The observation that eviction of BAF47 from the complexes is dependent upon only 2 amino acids in SSX demonstrates an unusual mechanism of oncogenesis and opens a therapeutic avenue.

Example 2

As mentioned above, there is a significant need in the art for novel therapeutic approaches for the treatment of synovial sarcoma. The diagnostic feature of synovial sarcoma is the t(X;18) chromosomal translocation which results in a highly precise, in-frame fusion of the SSX gene to SS18 which is hallmark to essentially 100% of cases. This translocation (FIG. 2A) fuses precisely 78 amino acids of SSX to the C-terminus of SS18 at amino acid 379. As a result, a fusion protein is translated that has all but the last 8 aa of SS18 directly joined to SSX1, 2 or 4. The precision of this translocation is worthy to note because it implies an equally precise mechanism of pathogenesis of SS in all cases observed to date.

In Example 1 above it is shown that the SS18-SSX fusion protein assembles into the BAF (also called mSWI/SNF) complexes, leading to the displacement of the wild type product of the non-translocated SS18 allele (WT SS18) and the eviction of the tumor suppressor subunit, BAF47 (also called hSNF5 or INI1) from the BAF complex. BAF47 is known to be a potent tumor suppressor and is biallelically inactivated in 100% of cases of pediatric malignant rhabdoid tumors (MRTs). Example 1 shows that this displacement and preferential assembly of the SS18-SSX fusion protein into BAF complexes leads to the assembly of aberrant BAF complexes that become targeted to the Sox2 gene locus, resulting in its activation. Sox2 gene activation, in turn, drives the proliferation of the malignant cells and is required for the proliferation of two SS cell lines in culture. Example 1 shows that increasing the concentration of the product of the wild type allele (WT SS18) such that it significantly exceeds that of the product of the translocated allele (SS18-SSX) leads to reassembly of normal BAF complexes and cessation of proliferation. In addition, shRNA-mediated knock-down of the SS18-SSX fusion (targeting only the malignant fusion and not the WT allele) restores normal BAF complex assembly, including increased protein levels and reassembly of BAF47 into complexes.

In addition, Example 1 shows that the ability of the SS18-SSX fusion to displace the WT allele and eject BAF47 depends on only two amino acids that are present in the transforming SSX genes (SSX1,2, and 4), but not in the non-transforming SSX family members (SSX3,5). The last 8 amino acids of the 78 amino acid SSX tail added to SS18 are also critical for the transforming phenotype. These studies identify a mechanism of reversible transformation and map the critical determinants to a small druggable region of the SS18-SSX fusion protein. A conceptual overview of this mechanism is illustrated in FIG. 7D.

The mechanism shown in FIG. 4 provides a pathway to the development of therapeutics for human synovial sarcoma. A small molecule that obscured the oncogenic region of SS18-SSX1,2, or 4 will prevent its assembly into BAF complexes, restoring the repression of Sox2 by H3K27me3, leading to a resumed non-transformed state, as illustrated.

The region of SSX family member proteins that determines the potential to evict the tumor suppressor BAF47 are amino acids 43,44 and the region of the last 8 amino acids. Substitution of the two amino acids at positions 43,44 in SSX1 (K43,R44) with the residues (M43,I44) from the non-transforming SSX family member SSX3 leads to normal complex assembly and cessation of proliferation. A small molecule capable of binding these hydrophilic residues will prevent the assembly of the SS18-SSX fusion protein into BAF complexes and restore the non-transformed state.

A high-throughput, gain-of-function screening method to detect molecules with the ability to favor the assembly of the normal BAF complex (FIG. 7A, B) is provided here. The screen is reliant upon the discovery that incorporation of the SS18-SSX fusion protein leads to eviction of BAF47 and its subsequent destabilization and proteasome-mediated degradation. Hence, a molecule that would favor assembly of normal BAF complexes would lead to increased levels of the BAF47 protein by virtue of its ability to assembly into complexes and its subsequent stabilization (as demonstrated with either shRNA-mediated knock down of the SS18-SSX fusion or by overexpression of wild-type SS18).

A lentiviral delivery construct is prepared which tags firefly luciferase to the C-terminus of full length BAF47. Introduction of tagged BAF47 into both SS cell lines results in minimally detectable total protein levels, as well as BAF47 protein levels on BAF complexes as assessed by anti-Brg immunoprecipitation studies (FIG. 7A). Upon co-introduction of SS18 WT or KD of the SS18-SSX fusion, increased BAF47 total protein levels and BAF-associated protein is observed (FIG. 7B). Therefore, small molecules that lead to the reassembly of BAF47 into complexes will therefore lead to an increase in luciferase signal, (i.e. a gain-of-function). This gain-of-function approach has the advantage in that it will eliminate non-specific toxic molecules that simply kill the cell or impair transcription, translation or protein stability.

In the synovial sarcoma cell lines Aska-SS and Yamato-SS, BAF47-luciferase is evicted from BAF complexes leading to its destabilization. In the presence of a small molecule, e.g. a small molecule that binds to the K43-R44 amino acids of SSX1, SSX2 or SSX4, we expect that the transforming SS18-SSX fusion will not be able to assemble into BAF complexes. We further expect that this class of synovial sarcoma therapeutics will have the general features of one hydrophobic side (which will mimic the M, I residues in the non-transforming SSX family members) and one hydrophilic side that will bind the hydrophobic K43, R44 residues. In the presence of such small molecules BAF47 will be incorporated into complexes, leading to its stabilization (as detected by increased luciferase signal), reduced Sox2 expression, and cessation of proliferation.

Secondary screens may be performed to validate identified candidate agents. Examples of secondary screens include (1) Sox2 repression (e.g., an RT-PCR based assay); and (2) Ink4a activation. For example, the Ink4a tumor suppressor gene is repressed in Aska-SS and Yamato-SS cell lines by tri-methylation of lysine 27 on histone H3 (H3K27me3) at its promoter (in primary human fibroblasts, this repressive complex is not found at the Ink4a locus and Ink4a is expressed). Increasing the concentration of the wildtype SS18 protein results in the formation of a normal BAF complex, which promotes the removal of H3K27me3 from the Ink4a locus and an increase in expression of the Ink4a gene. Detecting an increase in activity of the Ink4a promoter, e.g. by using a reporter protein operably linked to the Ink4a promoter, or by detectably labeling the Ink4a gene and detecting increased Ink4a protein levels, can be used as a read-out to identify an agent that promotes the assembly of wild-type BAF complexes in the presence of SS18-SSX fusion protein. Molecules which favor formation of normal BAF complexes will remove the PRC2-placed repressive peak over Ink4a and result in higher levels of detectable Ink4a, which can be detected by a variety of methods.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of the present invention is embodied by the appended claims.

That which is claimed is:

1. A method for screening a candidate agent for the ability to promote the assembly of wild-type BAF complexes, said method comprising:
   contacting a cell comprising a BAF complex comprising a SS18-SSX fusion protein with a candidate agent; and
   detecting a change in a cellular parameter to identify promotion of the assembly of wild-type BAF complexes comprising tumor suppressor subunit BAF47 polypeptide in the presence of SS18-SSX fusion protein,
   wherein said cellular parameter is selected from the group consisting of the amount of BAF47 polypeptide in the cell, the activity of Ink4a promoter in the cell, the activity of Sox2 promoter in the cell, and combinations thereof,
   wherein the assembly of wild-type BAF complexes is promoted when the amount of BAF47 polypeptide is increased, the activity of Ink4a promoter is increased, and/or the activity of the Sox2 promoter is decreased when compared to in a cell not contacted with the candidate agent.

2. The method according to claim 1, wherein the amount of BAF47 polypeptide is detected with an agent that is specific for the BAF47 polypeptide.

3. The method according to claim 1, wherein the cell expresses a detectably labeled BAF47 polypeptide, wherein the detecting comprises detecting the detectable label of the BAF47 polypeptide.

4. The method according to claim 1, wherein the amount of BAF47 polypeptide is detected by the incorporation of BAF47 into the complex.

5. A method for screening a candidate agent for the ability to promote the assembly of wild-type BAF complexes, said method comprising:
   contacting said candidate agent with a BAF complex comprising a SS18-SSX fusion protein is bound to a detection bead in the presence of a detectably labeled BAF47,
   wherein an increase in proximity of the BAF47 to the detection bead indicates that the candidate agent has the ability to promote the assembly of wild-type BAF complexes.

6. The method according to claim 5, wherein the detection bead is a scintillation proximity assay (SPA) bead and the detectable label is a radioisotope.

7. The method according to claim 5, wherein the BAF complex is tagged with a first moiety and the BAF47 is tagged with a second moiety, wherein the detecting comprises detecting a signal produced by the proximity of the first moiety with the second moiety.

8. The method according to claim 5, wherein the BAF complex is tagged with a first moiety and the SS18-SSX fusion protein is tagged with a second moiety, wherein the detecting comprises detecting the loss of a signal produced by the proximity of the first moiety with the second moiety.

9. A method for screening a candidate agent for the ability to promote the assembly of wild-type BAF complexes, said method comprising:
   contacting said candidate agent with SS18-SSX fusion protein and wild-type SS18, wherein an agent that binds SS18-SSX fusion protein and not wild type SS18 will promote the assembly of wild-type BAF complexes in the presence of SS18-SSX fusion protein.

10. A method of promoting the assembly of wild-type BAF complexes in a cell, said method comprising: contacting a cell comprising a mutant BAF complex comprising a SS18-SSX fusion polypeptide with an effective amount of agent to displace the SS18-SSX fusion polypeptide from the complex and promote the assembly of wild-type BAF complexes comprising SS18 polypeptide, BRG and BAF47 polypeptide; wherein the agent is a wild type SS18 polypeptide or an active fragment thereof.

11. The method according to claim 10, wherein the agent is an active fragment of a wild type SS18 polypeptide.

12. A method of promoting the assembly of wild-type BAF complexes in a cell, said method comprising: contacting a cell comprising a mutant BAF complex comprising a SS18-SSX fusion polypeptide with an effective amount of agent to displace the SS18-SSX fusion polypeptide from the complex and promote the assembly of wild-type BAF complexes comprising SS18 polypeptide, BRG and BAF47 polypeptide; wherein the agent is a nucleic acid that encodes a wild-type SS 18 polypeptide or an active fragment thereof, wherein expression of said nucleic acid results in increases in intracellular SS18 or an active fragment thereof.

13. The method according to claim 12, wherein agent is the nucleic acid encoding the active fragment of a wild type SS18 polypeptide.

14. A method for treating human synovial sarcoma (SS) in an individual expressing SS18-SSX fusion protein, said method comprising administering to said individual an effective amount of wild type SS18 polypeptide or an active fragment thereof, wherein said synovial sarcoma is treated.

15. The method according to claim 14, further comprising administering chemotherapy or radiotherapy to the individual.

16. A method for treating human synovial sarcoma (SS) in an individual expressing SS18-SSX fusion protein, said method comprising administering to said individual an effective amount of a nucleic acid that encodes a wild-type SS18 polypeptide or an active fragment thereof, wherein expression of said nucleic acid results in increases in intracellular SS18 or an active fragment thereof, wherein said synovial sarcoma is treated.

17. The method according to claim 16, further comprising administering chemotherapy or radiotherapy to the individual.

* * * * *